US012576055B2

(12) United States Patent
Hazen et al.

(10) Patent No.: US 12,576,055 B2
(45) **Date of Patent: \*Mar. 17, 2026**

(54) DISEASE DETECTION AND TREATMENT BASED ON TRIMETHYL-LYSINE LEVELS

(71) Applicant: The Cleveland Clinic Foundation, Cleveland, OH (US)

(72) Inventors: Stanley L. Hazen, Pepper Pike, OH (US); Zeneng Wang, Shaker Heights, OH (US); Xinmin S. Li, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1327 days.

This patent is subject to a terminal disclaimer.

(21) Appl. No.: 16/965,629

(22) PCT Filed: Feb. 1, 2019

(86) PCT No.: PCT/US2019/016361
§ 371 (c)(1),
(2) Date: Jul. 29, 2020

(87) PCT Pub. No.: WO2019/152847
PCT Pub. Date: Aug. 8, 2019

(65) Prior Publication Data
US 2021/0038550 A1 Feb. 11, 2021

Related U.S. Application Data

(60) Provisional application No. 62/624,969, filed on Feb. 1, 2018.

(51) Int. Cl.
| | |
|---|---|
| *A61K 31/198* | (2006.01) |
| *A61K 31/133* | (2006.01) |
| *A61K 31/4164* | (2006.01) |
| *A61K 31/675* | (2006.01) |
| *A61P 9/04* | (2006.01) |
| *A61P 13/12* | (2006.01) |
| *G01N 21/33* | (2006.01) |
| *G01N 24/08* | (2006.01) |
| *A61K 45/06* | (2006.01) |

(52) U.S. Cl.
CPC .......... *A61K 31/198* (2013.01); *A61K 31/133* (2013.01); *A61K 31/4164* (2013.01); *A61K 31/675* (2013.01); *A61P 9/04* (2018.01); *A61P 13/12* (2018.01); *G01N 21/33* (2013.01); *G01N 24/08* (2013.01); *A61K 45/06* (2013.01); *G01N 2800/34* (2013.01)

(58) Field of Classification Search
None
See application file for complete search history.

(56) References Cited

U.S. PATENT DOCUMENTS

| | | | |
|---|---|---|---|
| 9,168,233 | B2 | 10/2015 | Hazen et al. |
| 9,694,020 | B2 * | 7/2017 | Hazen ................. G01N 33/492 |
| 2010/0285517 | A1 | 11/2010 | Hazen et al. |
| 2012/0088259 | A1 | 4/2012 | Pinet et al. |
| 2012/0157397 | A1 | 6/2012 | Hazen et al. |
| 2016/0074440 | A1 | 3/2016 | Brugere et al. |
| 2016/0089386 | A1 | 3/2016 | Hazen |
| 2017/0152222 | A1 | 6/2017 | Garcia-Garcia et al. |
| 2018/0000754 | A1 | 1/2018 | Hazen et al. |

FOREIGN PATENT DOCUMENTS

WO      WO 2018/236899      12/2018

OTHER PUBLICATIONS

International Search Report and Written Opinion for PCT/US19/16361. Mailed Apr. 23, 2019. 15 pages.
Afshinnia et al., Impaired beta-Oxidation and Altered Complex Lipid Fatty Acid Partitioning with Advancing CKD. J Am Soc Nephrol. Jan. 2018;29(1):295-306.
Albert et al., Myocardial lipidomics. Developments in myocardial nuclear lipidomics. Front Biosci. Jan. 1, 2007;12:2750-60.
Aldous et al., Comparison of high sensitivity and contemporary troponin assays for the early detection of acute myocardial infarction in the emergency department. Ann Clin Biochem. May 2011;48(Pt 3):241-8.
Austin et al., Introduction to the Analysis of Survival Data in the Presence of Competing Risks. Circulation. Feb. 9, 2016;133(6):601-9.
Beger et al., Metabolomics enables precision medicine: "A White Paper, Community Perspective". Metabolomics. 2016;12(10):149. 15 pages.
Body et al., One Shot to Rule Out: Does the Limit of Detection of a High-Sensitivity Troponin Assay Hit the Mark? Clin Chem. Jan. 2017;63(1):21-23.
Brennan et al., Prognostic value of myeloperoxidase in patients with chest pain. N Engl J Med. Oct. 23, 2003;349(17):1595-604.
Chapman et al., Association of High-Sensitivity Cardiac Troponin I Concentration With Cardiac Outcomes in Patients With Suspected Acute Coronary Syndrome. JAMA. Nov. 21, 2017;318(19):1913-1924.

(Continued)

*Primary Examiner* — Sean McGarry
(74) *Attorney, Agent, or Firm* — Casimir Jones, S.C.; Jason R. Bond

(57) ABSTRACT

The present invention relates to systems, kits, and methods for identifying subjects with increased levels of N6-trimethyl-lysine (TML) or the combination of TML and trimethylamine-n-oxide (TMAO), as well as methods of determining risk of disease (e.g., kidney disease or heart failure) based on such levels. In certain embodiments, subjects with elevated TML, or TML and TMAO are treated with a therapeutic (e.g., one that inhibits the TMA/FMO3/TMAO pathway).

3 Claims, 23 Drawing Sheets

(56)                    References Cited

OTHER PUBLICATIONS

Chapman et al., Comparison of the Efficacy and Safety of Early Rule-Out Pathways for Acute Myocardial Infarction. Circulation. Apr. 25, 2017;135(17):1586-1596.

Chen et al., A new method of quaternizing aminies and its use in amino acid and peptide chemistry. Can J Chem. 1976;54:3310-3311.

Chen et al., A specific CD36-dependent signaling pathway is required for platelet activation by oxidized low-density lipoprotein. Circ Res. Jun. 20, 2008;102(12):1512-9.

Craciun et al., Microbial conversion of choline to trimethylamine requires a glycyl radical enzyme. Proc Natl Acad Sci U S A. Dec. 26, 2012;109(52):21307-12.

Davis et al., Excess dietary lysine increases skeletal muscle and plasma trimethyllysine in rats. J Nutr. Jun. 1993;123(6):1109-16.

Delong et al., Comparing the areas under two or more correlated receiver operating characteristic curves: a nonparametric approach. Biometrics. Sep. 1988;44(3):837-45.

Dunn et al., Carnitine biosynthesis by the perfused rat liver from exogenous protein-bound trimethyllysine. Metabolism of methylated lysine derivatives arising from the degradation of 6-N-[methyl-3H]lysine-labeled glycoproteins. J Biol Chem. Dec. 10, 1981;256(23):12437-44.

Dunn et al., Carnitine biosynthesis from gamma-butyrobetaine and from exogenous protein-bound 6-N-trimethyl-L-lysine by the perfused guinea pig liver. Effect of ascorbate deficiency on the in situ activity of gamma-butyrobetaine hydroxylase. J Biol Chem. Sep. 10, 1984;259(17):10764-70.

Eagle et al., Identifying patients at high risk of a cardiovascular event in the near future: current status and future directions: report of a national heart, lung, and blood institute working group. Circulation. Mar. 30, 2010;121(12):1447-54.

Fischer et al., A moderate excess of dietary lysine lowers plasma and tissue carnitine concentrations in pigs. Br J Nutr. Jan. 2009;101(2):190-6.

Giannitsis et al., Analytical validation of a high-sensitivity cardiac troponin T assay. Clin Chem. Feb. 2010;56(2):254-61.

Greer et al., Members of the H3K4 trimethylation complex regulate lifespan in a germline-dependent manner in C. elegans. Nature. Jul. 15, 2010;466(7304):383-7.

Gregory et al., Transmission of atherosclerosis susceptibility with gut microbial transplantation. J Biol Chem. Feb. 27, 2015;290(9):5647-60.

Gross. The evolution of lipidomics through space and time. Biochim Biophys Acta Mol Cell Biol Lipids. Aug. 2017;1862(8):731-739.

Handy et al., Epigenetic modifications: basic mechanisms and role in cardiovascular disease. Circulation. May 17, 2011;123(19):2145-56.

Hollander et al., State-of-the-Art Evaluation of Emergency Department Patients Presenting With Potential Acute Coronary Syndromes. Circulation. Aug. 16, 2016;134(7):547-64.

Hoppel et al., N6-Trimethyl-lysine metabolism. 3-Hydroxy-N6-trimethyl-lysine and carnitine biosynthesis. Biochem J. May 15, 1980;188(2):509-19.

Hulse et al., Carnitine biosynthesis. beta-Hydroxylation of trimethyllysine by an alpha-ketoglutarate-dependent mitochondrial dioxygenase. J Biol Chem. Mar. 10, 1978;253(5):1654-9.

Huszar. Tissue-specific biosynthesis of epsilon-N-monomethyllysine and epsilon-N-trimethyllysine in skeletal and cardiac muscle myosin: a model for the cell-free study of post-translational amino acid modifications in proteins. J Mol Biol. May 25, 1975;94(3):311-26.

Kind et al., Identification of small molecules using accurate mass MS/MS search. Mass Spectrom Rev. Jul. 2018;37(4):513-532.

Klingenberg et al., Improved risk stratification of patients with acute coronary syndromes using a combination of hsTnT, NT-proBNP and hsCRP with the Grace score. Eur Heart J Acute Cardiovasc Care. Mar. 2018;7(2):129-138.

Koeth et al., gamma-Butyrobetaine is a proatherogenic intermediate in gut microbial metabolism of L-carnitine to TMAO. Cell Metab. Nov. 4, 2014;20(5):799-812.

Koeth et al., Intestinal microbiota metabolism of L-carnitine, a nutrient in red meat, promotes atherosclerosis. Nat Med. May 2013;19(5):576-85.

Korley et al., Preparing the United States for high-sensitivity cardiac troponin assays. J Am Coll Cardiol. Apr. 30, 2013;61(17):1753-8.

Kouzarides. Chromatin modifications and their function. Cell. Feb. 23, 2007;128(4):693-705.

Labadie et al., Hepatic synthesis of carnitine from protein-bound trimethyl-lysine. Lysosomal digestion of methyl-lysine-labelled asialo-fetuin. Biochem J. Oct. 15, 1976;160(1):85-95.

Leening et al., Net reclassification improvement: computation, interpretation, and controversies: a literature review and clinician's guide. Ann Intern Med. Jan. 21, 2014;160(2):122-31.

Levey et al., A new equation to estimate glomerular filtration rate. Ann Intern Med. May 5, 2009;150(9):604-12.

Li et al., Gut microbiota-dependent trimethylamine N-oxide in acute coronary syndromes: a prognostic marker for incident cardiovascular events beyond traditional risk factors. Eur Heart J. Mar. 14, 2017;38(11):814-824.

Li et al., Untargeted metabolomics identifies trimethyllysine, a TMAO-producing nutrient precursor, as a predictor of incident cardiovascular disease risk. JCI Insight 2018;3(6):e99096(6). 18 pages.

Loland et al., The association between progression of atherosclerosis and the methylated amino acids asymmetric dimethylarginine and trimethyllysine. PLoS One. May 29, 2013;8(5):e64774. 9 pages.

McErlean et al., Comparison of troponin T versus creatine kinase-MB in suspected acute coronary syndromes. Am J Cardiol. Feb. 15, 2000;85(4):421-6.

Morse et al., Sites of biological methylation of proteins in cultured chick muscle cells. Biochemistry. Sep. 23, 1975;14(19):4316-25.

Muller-Bardorff et al., Improved troponin T Elisa specific for cardiac troponin T isoform: assay development and analytical and clinical validation. Clin Chem. Mar. 1997;43(3):458-66.

Nikpay et al., A comprehensive 1,000 Genomes-based genome-wide association meta-analysis of coronary artery disease. Nat Genet. Oct. 2015;47(10):1121-1130.

Peacock et al., Efficacy of High-Sensitivity Troponin T in Identifying Very-Low-Risk Patients With Possible Acute Coronary Syndrome. JAMA Cardiol. Feb. 1, 2018;3(2):104-111.

Pencina et al., Evaluating the added predictive ability of a new marker: from area under the ROC curve to reclassification and beyond. Stat Med. Jan. 30, 2008;27(2):157-72; discussion 207-12.

Pencina et al., Extensions of net reclassification improvement calculations to measure usefulness of new biomarkers. Stat Med. Jan. 15, 2011;30(1):11-21.

Pluskal et al., MZmine 2: modular framework for processing, visualizing, and analyzing mass spectrometry-based molecular profile data. BMC Bioinformatics. Jul. 23, 2010;11:395.

Porras-Yakushi et al., A novel SET domain methyltransferase modifies ribosomal protein Rpl23ab in yeast. J Biol Chem. Oct. 14, 2005;280(41):34590-8.

Purcell et al., Plink: a tool set for whole-genome association and population-based linkage analyses. Am J Hum Genet. Sep. 2007;81(3):559-75.

Qi et al., Circulating trimethylamine N-oxide and the risk of cardiovascular diseases: a systematic review and meta-analysis of 11 prospective cohort studies. J Cell Mol Med. Jan. 2018;22(1):185-194.

Rakoff-Nahoum et al., Recognition of commensal microflora by toll-like receptors is required for intestinal homeostasis. Cell. Jul. 23, 2004;118(2):229-41.

Rhein et al., Human METTL20 methylates lysine residues adjacent to the recognition loop of the electron transfer flavoprotein in mitochondria. J Biol Chem. Aug. 29, 2014;289(35):24640-51.

Roffi et al., 2015 ESC Guidelines for the management of acute coronary syndromes in patients presenting without persistent ST-segment elevation: Task Force for the Management of Acute Coronary Syndromes in Patients Presenting without Persistent ST-Segment Elevation of the European Society of Cardiology (ESC). Eur Heart J. Jan. 14, 2016;37(3):267-315.

(56)          References Cited

OTHER PUBLICATIONS

Romano et al., Intestinal microbiota composition modulates choline bioavailability from diet and accumulation of the proatherogenic metabolite trimethylamine-N-oxide. mBio. Mar. 17, 2015;6(2):e02481. 8 pages.

Schiattarella et al., Gut microbe-generated metabolite trimethylamine-N-oxide as cardiovascular risk biomarker: a systematic review and dose-response meta-analysis. Eur Heart J. Oct. 14, 2017;38(39):2948-2956.

Scoumanne et al., Protein methylation: a new mechanism of p53 tumor suppressor regulation. Histol Histopathol. Sep. 2008;23(9):1143-9.

Seldin et al., Trimethylamine N-Oxide Promotes Vascular Inflammation Through Signaling of Mitogen-Activated Protein Kinase and Nuclear Factor-Kb. J Am Heart Assoc. Feb. 22, 2016;5(2):e002767. 12 pages.

Senthong et al., Trimethylamine N-Oxide and Mortality Risk in Patients With Peripheral Artery Disease. J Am Heart Assoc. Oct. 19, 2016;5(10):e004237. 14 pages.

Servillo et al., Where does N(ε)-trimethyllysine for the carnitine biosynthesis in mammals come from? PLoS One. Jan. 13, 2014;9(1):e84589. 7 pages.

Shi et al., Histone demethylation mediated by the nuclear amine oxidase homolog LSD1. Cell. Dec. 29, 2004;119(7):941-53.

Skagen et al., The Carnitine-butyrobetaine-trimethylamine-N-oxide pathway and its association with cardiovascular mortality in patients with carotid atherosclerosis. Atherosclerosis. Apr. 2016;247:64-9.

Stallcup. Role of protein methylation in chromatin remodeling and transcriptional regulation. Oncogene. May 28, 2001;20(24):3014-20.

Strand et al., Serum Carnitine Metabolites and Incident Type 2 Diabetes Mellitus in Patients With Suspected Stable Angina Pectoris. J Clin Endocrinol Metab. Mar. 1, 2018;103(3):1033-1041.

Suzuki et al., Trimethylamine N-oxide and Risk Stratification after Acute Myocardial Infarction. Clin Chem. Jan. 2017;63(1):420-428.

Tang et al., Intestinal microbial metabolism of phosphatidylcholine and cardiovascular risk. N Engl J Med. Apr. 25, 2013;368(17):1575-84.

Tang et al., Increased Trimethylamine N-Oxide Portends High Mortality Risk Independent of Glycemic Control in Patients with Type 2 Diabetes Mellitus. Clin Chem. Jan. 2017;63(1):297-306.

Thelin et al., Early rule-out of acute coronary syndrome using undetectable levels of high sensitivity troponin T. Eur Heart J Acute Cardiovasc Care. Oct. 2015;4(5):403-9.

Tsugawa et al., Hydrogen Rearrangement Rules: Computational MS/MS Fragmentation and Structure Elucidation Using MS-Finder Software. Anal Chem. Aug. 16, 2016;88(16):7946-58.

Tsugawa et al., MS-DIAL: data-independent MS/MS deconvolution for comprehensive metabolome analysis. Nat Methods. Jun. 2015;12(6):523-6.

Tsukada et al., Histone demethylation by a family of JmjC domain-containing proteins. Nature. Feb. 16, 2006;439(7078):811-6.

Ussher et al., The Emerging Role of Metabolomics in the Diagnosis and Prognosis of Cardiovascular Disease. J Am Coll Cardiol. Dec. 27, 2016;68(25):2850-2870.

Van De Werf et al., Management of acute myocardial infarction in patients presenting with ST-segment elevation. The Task Force on the Management of Acute Myocardial Infarction of the European Society of Cardiology. Eur Heart J. Jan. 2003;24(1):28-66.

Vaz et al., Carnitine biosynthesis in mammals. Biochem J. Feb. 1, 2002;361(Pt 3):417-29.

Wang et al., Gut flora metabolism of phosphatidylcholine promotes cardiovascular disease. Nature. Apr. 7, 2011;472(7341):57-63.

Wang et al., Measurement of trimethylamine-N-oxide by stable isotope dilution liquid chromatography tandem mass spectrometry. Anal Biochem. Jun. 15, 2014;455:35-40.

Wang et al., Non-lethal Inhibition of Gut Microbial Trimethylamine Production for the Treatment of Atherosclerosis. Cell. Dec. 17, 2015;163(7):1585-95.

Wang et al., Prognostic value of choline and betaine depends on intestinal microbiota-generated metabolite trimethylamine-N-oxide. Eur Heart J. Apr. 2014;35(14):904-10.

Wang et al., Protein carbamylation links inflammation, smoking, uremia and atherogenesis. Nat Med. Oct. 2007;13(10):1176-84.

Wang et al., Sharing and community curation of mass spectrometry data with Global Natural Products Social Molecular Networking. Nat Biotechnol. Aug. 9, 2016;34(8):828-837.

Wohlgemuth et al., Splash, a hashed identifier for mass spectra. Nat Biotechnol. Nov. 8, 2016;34(11):1099-1101.

Yang et al., Lipidomics: Techniques, Applications, and Outcomes Related to Biomedical Sciences. Trends Biochem Sci. Nov. 2016;41(11):954-969.

Zhang et al., Lysine methylation: beyond histones. Acta Biochim Biophys Sin (Shanghai). Jan. 2012;44(1):14-27.

Zhelev et al., Diagnostic accuracy of single baseline measurement of Elecsys Troponin T high-sensitive assay for diagnosis of acute myocardial infarction in emergency department: systematic review and meta-analysis. BMJ. Jan. 20, 2015;350:h15. 14 pages.

Zhu et al., Carnitine metabolism to trimethylamine by an unusual Rieske-type oxygenase from human microbiota. Proc Natl Acad Sci U S A. Mar. 18, 2014;111(11):4268-73.

Zhu et al., Gut Microbial Metabolite TMAO Enhances Platelet Hyperreactivity and Thrombosis Risk. Cell. Mar. 24, 2016;165(1):111-124.

* cited by examiner

A Synthetic d9-TML

$C_9D_9H_{12}N_2O_2$
$M^+(m/z)=198.2168$

B Synthetic d9-TML

DISEASE DETECTION AND TREATMENT BASED ON TRIMETHYL-LYSINE LEVELS

The present application claims priority to U.S. Provisional application Ser. No. 62/624,969, filed Feb. 1, 2018, which is herein incorporated by reference in its entirety.

STATEMENT REGARDING FEDERAL FUNDING

This invention was made with government support under grant number HL103866 awarded by the National Institutes of Health. The government has certain rights in the invention.

FIELD OF THE INVENTION

The present invention relates to systems, kits, and methods for identifying subjects with increased levels of N6-trimethyl-lysine (TML) or the combination of TML and trimethylamine-n-oxide (TMAO), as well as methods of determining risk of disease (e.g., kidney disease or heart failure) based on such levels. In certain embodiments, subjects with elevated TML, or TML and TMAO are treated with a therapeutic (e.g., one that inhibits the TMA/FMO3/TMAO pathway).

BACKGROUND

Kidneys of the human body function to remove excess fluids as well as some ions. The functional unit of the kidney is the nephron. A nephron consists of a filtering unit of tiny blood vessels called a glomerulus attached to a tubule. When blood enters the glomerulus, it is filtered and the remaining fluid then passes along the tubule. In the tubule, chemicals and water are either added to or removed from this filtered fluid according to the body's needs, and the final product is urine, which is excreted.

In patients with chronic kidney disease, kidney function is severely compromised. Chronic kidney disease (CKD), also known as chronic renal disease, is a progressive loss in renal function over a period of months or years. The most severe stage of CKD is End Stage Renal Disease (ESRD), which occurs when the kidneys cease to function. The two main causes of CKD are diabetes and high blood pressure, which are responsible for up to two-thirds of the cases. Heart disease is the leading cause of death for all people having CKD. Excessive fluid can accumulate in patients suffering from ESRD. The mortality rate of ESRD patients who receive traditional hemodialysis therapy is 24% per year with an even higher mortality rate among diabetic patients. Fluid accumulates in ESRD patients because the kidneys can no longer effectively remove water and other fluids from the body. The fluid accumulates first in the blood and then accumulates throughout the body, resulting in swelling of the extremities and other tissues as edema. This accumulation of fluid causes increased stress on the heart, in turn causing significant increases in blood pressure or hypertension, which can lead to heart failure.

Although the population of patients afflicted with CKD grows each year, there is no cure. Current treatments for CKD seek to slow the progression of the disease. However, as the disease progresses, renal function decreases, and, eventually, renal replacement therapy is employed to compensate for lost kidney function. Renal replacement therapy entails either transplantation of a new kidney or dialysis.

Methods to treat kidney disease require the processing of blood to extract waste components such as urea and ions. The traditional treatment for kidney disease involves dialysis. Dialysis emulates kidney function by removing waste components and excess fluid from a patient's blood. This is accomplished by allowing the body fluids, usually the blood, to come into the close proximity with the dialysate, which is a fluid that serves to cleanse the blood and actively remove the waste components and excess water. During this process, the blood and dialysate are separated by a dialysis membrane, which is permeable to water, small molecules (such as urea), and ions but not permeable to the cells. Each dialysis session lasts a few hours and may be repeated as often as three times a week.

Traditional processes, such as dialysis, require extracorporeal processing of body fluids. Once the blood is purified, it is then returned to the patient. Although effective at removing waste components from blood, dialysis treatments are administered intermittently and, therefore, do not emulate the continuous function of a natural kidney. Once the dialysis session is completed, the fluid begins to accumulate again in the tissues of the patient. The benefits of dialysis notwithstanding, statistics indicate that three out of five dialysis patients die within five years of commencing treatment. Studies have shown that increasing the frequency and duration of dialysis sessions can improve the survivability of dialysis patients. Increasing the frequency and duration of dialysis sessions more closely resembles the continuous kidney function sought to be emulated. However, the extracorporeal processing of the body fluids increases the discomfort, inconvenience and the costs associated with treatment. There is also an additional risk of infection, which mandates that the procedures be carried out under the supervision of trained medical personnel.

SUMMARY OF THE INVENTION

The present invention relates to systems, kits, and methods for identifying subjects with increased levels of N6-trimethyl-lysine (TML) or the combination of TML and trimethylamine-n-oxide (TMAO), as well as methods of determining risk of disease (e.g., kidney disease or heart failure) based on such levels. In certain embodiments, subjects with elevated TML, or TML and TMAO are treated with a therapeutic (e.g., one that inhibits the TMA/FMO3/TMAO pathway).

In some embodiments, provided herein are methods of performing an activity based on the level of N6-trimethyl-lysine (TML) in a sample from a subject comprising: a) determining the level (e.g., concentration) of TML in a sample (e.g., blood, serum, plasma, or urine) from a subject; and b) performing at least one of the following activities: i) identifying increased TML levels in the sample compared to a control, and treating the subject with: A) a first agent or first procedure that inhibits the TMA/FMO3/TMAO pathway, and/or B) a second agent or second procedure used to treat diabetes, non-alcoholic steatohepatitis (NASH), cardiovascular disease, chronic kidney disease, or heart failure; and/or C) an antibiotic or antimicrobial that reduces trimethylamine (TMA) production in the gut; and/or D) by providing or prescribing a diet with reduced levels of camitine, choline, and/or lecithin containing compounds (e.g., a vegetarian or vegan diet); ii) generating and/or transmitting a report (e.g., electronic and/or paper report) that indicates the TML levels are elevated in the sample compared to a control level (e.g., report indicates medium or high risk of disease), and that the subject is in need of the first agent, the second agent, the first procedure, and/or the second procedure; iii) generating and/or transmitting a report (e.g., electronic and/or paper report) that indicates the TML levels are elevated in the sample compared to a control level, and that the subject has or is at risk of diabetes, NASH, cardiovascular disease, chronic kidney disease, and/or heart failure; and iv) characterizing the subject as having diabetes, NASH, cardiovascular disease, chronic kidney disease, and/or heart failure, based on finding elevated levels of the TML in the sample compared to a control level.

In some embodiments, provided herein are methods of treatment comprising: a) identifying a subject as having increased levels of N6-trimethyl-lysine (TML) compared to a control level, and b) treating the subject with at least one of the following: i) a first agent or first procedure that inhibits the TMA/FMO3/TMAO pathway; ii) a second agent or second procedure used to treat diabetes, NASH, cardiovascular disease, chronic kidney disease, or heart failure; and iii) an antibiotic or antimicrobial that reduces trimethylamine (TMA) production in the gut.

In further embodiments, the identifying comprises viewing results of a TML and/or TML and TMAO assays (e.g., on paper or on a computer screen) performed on a sample from the subject which show elevated TML and/or TML and TMAO levels. In certain embodiments, the identifying comprises viewing results of a TML or TMAO assay performed on a sample or exhaled breath from said subject which show elevated TML and/or TMAO levels. In certain embodiments, the level of TML is above 0.4 µM (or above 0.5 or 0.6 µM) and the level of TMAO is above 2.5 µM (or above 3.0 or 3.5 µM), and the subject is identified as increased or high risk for a disease selected from diabetes, NASH cardiovascular disease, chronic kidney disease, and heart failure.

In certain embodiments, provided herein are systems and kits comprising: a) a report (e.g., electronic or paper) for a subject with NASH, cardiovascular disease, chronic kidney disease, heart failure, and/or diabetes, wherein the report indicates that the patient has elevated levels of N6-trimethyl-lysine; and b) at least one of the following: i) a first agent that inhibits the TMA/FMO3/TMAO pathway; ii) a second agent used to treat chronic kidney disease, diabetes, or heart failure; and iii) an antibiotic or antimicrobial that reduces trimethylamine (TMA) production in the gut.

In some embodiments, provided herein are methods of performing an activity based on the level of both N6-trimethyl-lysine (TML) and trimethylamine N-oxide (TMAO) in a sample from a subject comprising: a) determining the level of TML and TMAO in the same sample, or separate samples, from a subject; b) determining the approximate risk of disease for the subject based on both the TML level and the TMAO level, wherein the disease is selected from the group consisting of: cardiovascular disease (e.g., atherosclerotic CVD), major adverse cardiac event (MACE), diabetes, chronic kidney disease, NASH, and heart failure, and c) performing at least one of the following: i) identifying the subject as at increased risk of the disease, and treating the subject with: A) a first agent or first procedure that inhibits the TMA/FMO3/TMAO pathway, and/or B) a second agent or second procedure used to treat cardiovascular disease, chronic kidney disease, NASH, diabetes, or heart failure; and/or C) an antibiotic or antimicrobial that reduces trimethylamine (TMA) production in the gut; and/or D) by providing or prescribing a diet with reduced levels of carnitine, choline, and/or lecithin containing compounds (e.g., a vegetarian or vegan diet); ii) generating and/or transmitting a report that indicates the subject is at increased risk of the disease, and that the subject is in need of the first agent, the second agent, the first procedure, the second procedure, and/or the antibiotic or antimicrobial; iii) generating and/or transmitting a report that indicates the subject is at low, medium or high risk of the disease; and iv) characterizing the subject as having cardiovascular disease, chronic kidney disease, diabetes, NASH, and/or heart failure, based on finding the subject is at high risk of the disease. In certain embodiments, the approximate risk of disease is selected from the group consisting of: low risk, medium risk, and high risk. In further embodiments, the increased risk of disease is medium or high risk of the disease. In further embodiments, the determining the approximate risk is performed with general reference to Table 9, Table 11, Table 12, Table 18, Table 19, and Table 20.

In additional embodiments, provided herein are systems or kits comprising: a) a report for a subject with chronic kidney disease, diabetes, NASH, cardiovascular disease, and/or heart failure, wherein the report indicates that the patient has elevated levels of N6-trimethyl-lysine (TML) compared to a control, and elevated levels of TMAO compared to a control; and b) at least one of the following: i) a first agent that inhibits the TMA/FMO3/TMAO pathway; ii) a second agent used to treat chronic cardiovascular disease, kidney disease, diabetes, diabetes, NASH, cardiovascular disease, or heart failure; and iii) an antibiotic or antimicrobial that reduces trimethylamine (TMA) production in the gut.

In some embodiments, provided herein are methods of treatment comprising: a) identifying a subject as having an increases risk of disease based on an analysis of both the N6-trimethyl-lysine (TML) level and trimethylamine-n-oxide (TMAO) level from one or more samples from the subject, and b) treating the subject with at least one of the following: i) a first agent or first procedure that inhibits the TMA/FMO3/TMAO pathway; ii) a second agent or second procedure used to treat cardiovascular disease, diabetes, NASH, cardiovascular disease, chronic kidney disease, diabetes, or heart failure; and iii) an antibiotic or antimicrobial that reduces trimethylamine (TMA) production in the gut. In certain embodiments, the identifying comprises receiving a report that the subject has increased TML and TMAO levels compared to controls (and, for example, elevated or non-elevated troponin T levels).

In certain embodiments, the subject has chronic kidney disease and/or heart failure. In certain embodiments, the subject is a human. In particular embodiments, the sample is selected from the group consisting of: a plasma sample, a serum sample, and a urine sample. In other embodiments, the determining comprises detecting the TML with an analytical device selected from: a mass spectrometer, NMR spectrometer, and a UV/Vis spectrometer. In further embodiments, the determining comprises contacting the sample with an anti-TML antibody (e.g., detectably labeled anti-TML antibody).

In certain embodiments, the identifying comprises receiving a report that the subject has increased TML levels compared to a control. In further embodiments, the subject has chronic kidney disease. In other embodiments, the subject is a human. In particular embodiments, the subject has heart failure.

In some embodiments, the provided herein are methods of detecting N6-trimethyl-lysine (TML) in a sample comprising: a) obtaining a sample, wherein the sample is from a human subject with diabetes, NASH, cardiovascular disease, chronic kidney disease, and/or heart failure; and b) treating the sample under conditions such that the concentration of TML present in the sample is determined. In further embodiments, the concentration of the TML in the sample is determined by mass spectrometry. In further embodiments, the sample is a plasma or serum sample.

In certain embodiments, the first agent or first procedure that inhibits the TMA/FMO3/TMAO pathway is selected from the group consisting of i) 3,3-dimethyl-1-butanol (DMB) or a DMB derivative or related compound (e.g., as shown in Formula IV); ii) acetylsalicylic acid with or without an enteric coating; iii) an acetylsalicylic acid derivative with or without an enteric coating; iv) a flavin monooxygenase 3 (FMO3) inhibitor; v) a gut TMA lyase inhibitor; vi) fecal microbiota transplantation; vii) delivery of acetylsalicylic acid or derivative thereof directly to the colon or cecum of the subject; viii) a probiotic or prebiotic that reduces TMA production in the gut; ix) an antiplatelet agent; x) a TMA and/or TMAO sequestering agent; xi) a moiety from Table 1 (e.g., a halomethyl or morpholine compound); xii) a compound comprising at least one of N,N-dimethylethanolamine (DMEA), N-methylethanolamine (MEA), ethanolamine (EA), trimethylsilyl ethanol, P-choline, and P,P,P-trimethyl ethanolphosphine, xiii) 3-(2,2,2-trimethylhydraziniumyl) propionate (mildronate, also known as THP, MET-88, Meldonium or Quarterine); and xiv) a compound of any of Formulas I-III (as described in U.S. Pat. Pub. 2018/0000754, which is herein incorporated by reference in its entirety, particularly for Formulas I-III), such as the compounds in Table 13 or a compound in Formula V.

In certain embodiments, the second agent or second procedure used to treat chronic kidney disease, or heart failure is selected from the group consisting of an ACE inhibitor, an angiotensin II receptor blocker (ARB), insulin, a statin, a lipid lowering drug, a blood-pressure medication, an amylinomimetic drug, an alpha-glucosidase inhibitor, a biguanide, a dopamine agonist, a DPP-4 inhibitor, a glucagon-like peptide, a meglitinide, a sodium glucose transporter (SGLT) 2 inhibitor, a sulfonylureas, Pioglitazone, cenicriviroc, Elafibranor, Ocaliva (obeticholic acid), Selonsertib, and/or a thiazolidinedione. In particular embodiments, the antibiotic is at least one antibiotic selected from the group consisting of: metronidazole, ciprofloxacin, neomycin, amoxicillin, and a broad spectrum antibiotic; and wherein the subject does not have an active infection. In further embodiments, the second agent or second procedure is used to treat chronic kidney disease. In other embodiments, the second agent or second procedure is used to treat heart failure.

In particular embodiments, the FMO3 inhibitor comprises Tenofovir or Methimazole. In some embodiments, the antibiotic is a broad spectrum antibiotic. In further embodiments, the antibiotic is one antibiotic or a combination of antibiotics selected from the group consisting of metronidazole, ciprofloxacin, and neomycin, amoxicillin. In particular embodiments, the antiplatelet agent is selected from the group consisting of: abciximab, dipyridamole/ASA, anagrelide, cilostazol, clopidogrel, dipyridamole, eptifabatide, prasugrel, ticagrelor, ticlopidine, tirofiban, and vorapaxar. In further embodiments, the enteric coating provides for release of a majority of the acetylsalicylic acid or the acetylsalicylic acid derivative in the colon or cecum of the subject. In some embodiments, the TMA and/or TMAO sequestering agent comprises activated charcoal or copper chlorophyllin (e.g., activated charcoal at 750 mg 2×/day for 10 days, or copper chlorophyllin at 60 mg 3×/day after meals for 3 weeks).

In certain embodiments, provided herein are methods of detecting N6-trimethyl-lysine (TML) in a sample (e.g., serum or plasma sample) comprising: a) obtaining sample (e.g., a plasma or serum sample), wherein the sample is from a human subject; b) introducing at least a portion of the sample into an analytical device under conditions such that the concentration of TML present in the sample is determined (e.g., wherein said analytical device comprises: i) an NMR spectrometer, a UV/Vis spectrometer, or a mass spectrometer, and ii) equipment to provide physical separation of said TMANO prior to determining said concentration); and c) at least one of the following: i) graphically displaying said subject's risk of having a disease as higher than normal if said level of TML in said plasma or serum sample is higher than a first minimum value, wherein said minimum value is at least 0.4 µM, wherein said disease is selected from the group consisting of heart failure, chronic kidney disease, NASH, cardiovascular disease, or diabetes; and/or ii) graphically displaying said subject's risk of having a disease as higher than normal based on said level of TML in said plasma or serum sample being higher than a first minimum value, wherein said minimum value is at least 0.4 µM, wherein said disease is selected from the group consisting of heart failure, chronic kidney disease, NASH, cardiovascular disease, or diabetes.

In some embodiments, the first minimum value is at least 0.5 µM, or at least 0.6 µM, or at least 0.7 µM, or at least at least 0.8 µM. In certain embodiments, the higher than normal risk is an intermediate risk. In other embodiments, the higher than normal risk is a high risk. In some embodiments, the methods further comprise determining the level of trimethylamine N-oxide (TMAO) in a sample from a subject, and graphically displaying the subject's risk as higher than normal if the TMAO level is higher than a second minimum value, wherein the second minimum value is at least 2.2 µM. In particular embodiments, the second minimum value is at least 2.5 µM or at least 3.0 µM or at least 3.5 µM or at least 4.0 µM or at least 4.5 µM. In some embodiments, the subject has, or is suspected of having, heart failure, chronic kidney disease, NASH, cardiovascular disease, and/or diabetes. In further embodiments, the subject has a non-elevated level of troponin T. In other embodiments, the method further comprises graphically displaying the non-elevated level of troponin T.

US 12,576,055 B2

7

Figure 2:
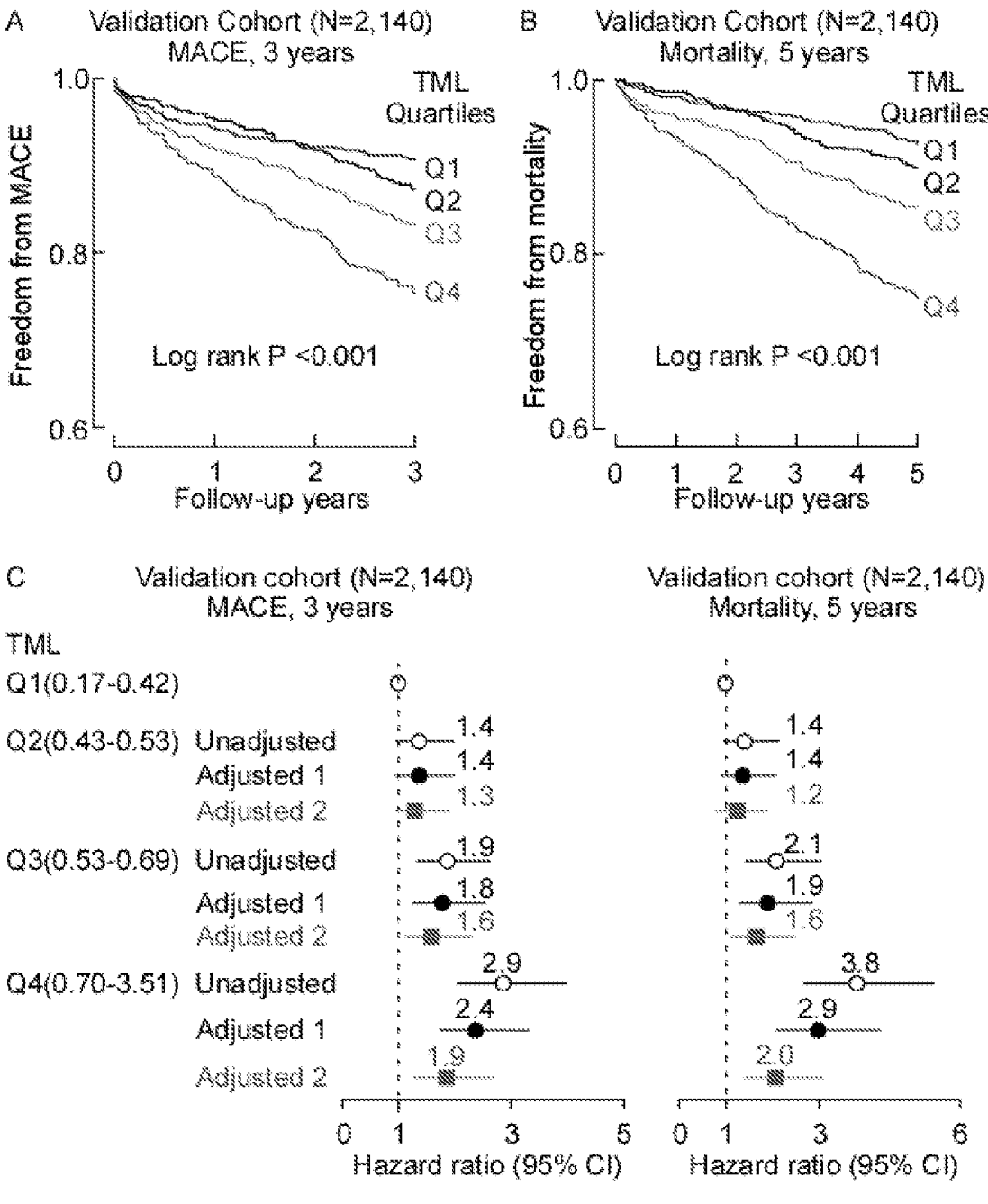

FIG. 2. Stable isotope dilution LC/MS/MS analyses verify systemic levels of TML are associated with incident CVD risks independent of TMAO. Kaplan-Meier estimates and 3 year risks (Hazard Ratio (95% Confidence Intervals)) for (A) major adverse cardiac events (MACE, including myocardial infarction, stroke or death); and (B) all-cause mortality (5 years) ranked by TML quartiles in the Validation Cohort (N=2,140). (C) Forest plots indicate the HR (95% CI) for incident (3 year) risk for MACE and all-cause mortality (5 years) according to TML quartiles. Hazard Ratio (unadjusted, open circles), and multivariable Cox model 1 adjusted (filled black circles; adjusted for age, sex, high density lipoprotein (HDL), low density lipoprotein (LDL), smoking, diabetes mellitus, hypertension, C-reactive protein level), or model 2 adjusted (filled red squares, adjusted for model 1 plus TMAO). The 5-95% confidence interval is indicated by line length. The analyses were performed using R 3.4.1.

Figure 3:
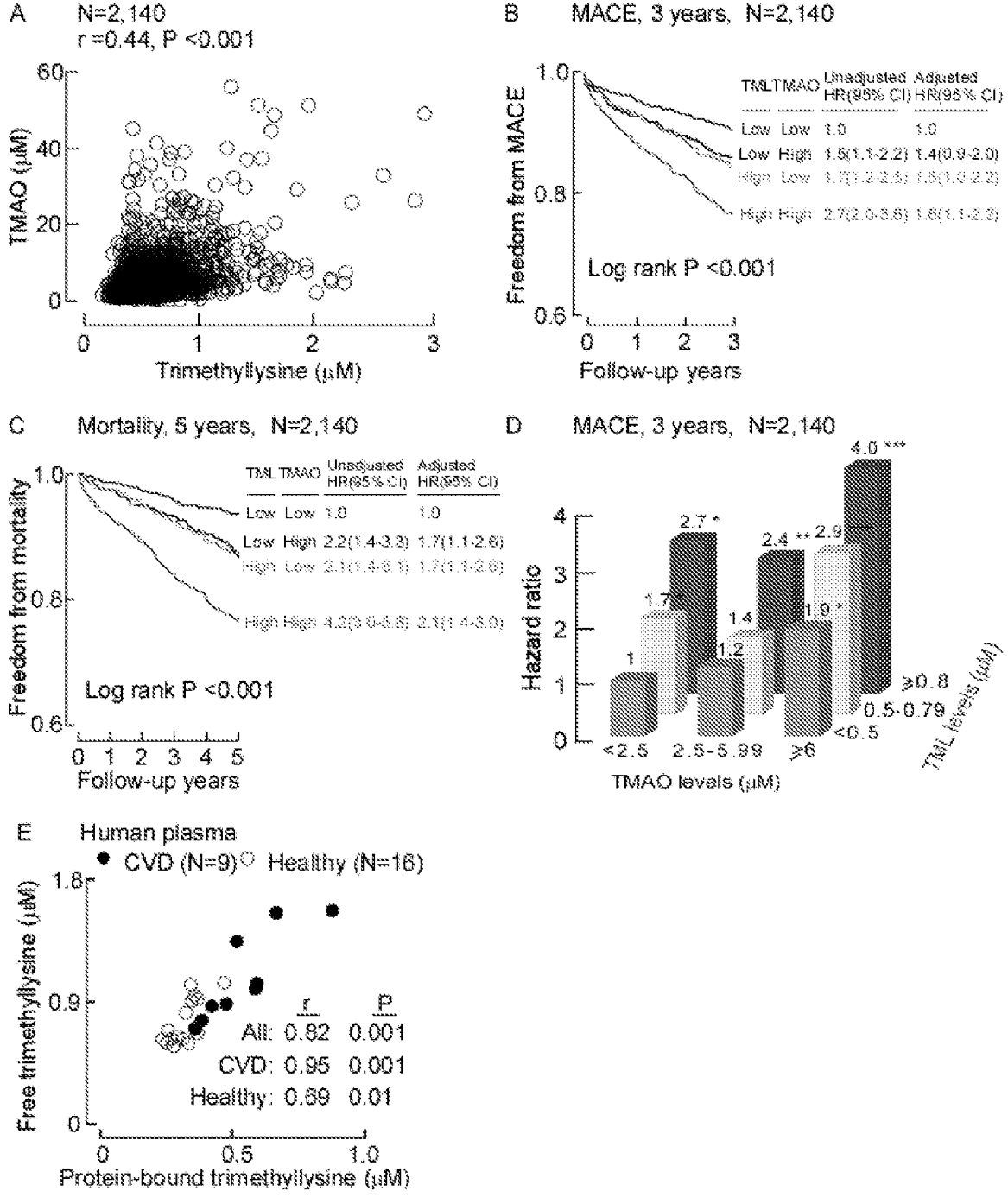

FIG. 3. Relationship between plasma TML and both CVD risks and TMAO. (A) Correlation between plasma levels of TML and TMAO in the Validation Cohort (N=2,140); (B) Kaplan-Meier plot illustrating the relationship between plasma TML and risk of incident (3-year) MACE; and (C) incident (5-year) mortality risks according to TML and TMAO levels where each marker is categorized above vs below the median level in the Validation Cohort (N=2,140). Also shown are hazard ratio (95% confidence interval) (HR (95% CI)) for the indicated TML and TMAO grouping using either an unadjusted model, or following adjustments for traditional cardiovascular risk factors (age, sex, HDL, LDL, smoking, diabetes mellitus, hypertension), high sensitivity C-reactive protein level, estimated glomerular filtration rate (eGFR), history of CAD and medications. Median plasma concentration of TML (0.53 μM) and TMAO (3.69 μM) within the cohort was used to stratify subjects as 'high' (≥median) or 'low' (<median) values; (D) Plot of Hazard Ratio for incident 3-year MACE risk stratified by indicated low, intermediate and high levels of TMAO (cutoff values 2.5 and 6 μM) and TML (cutoff values of 0.5 and 0.8 μM). *P<0.05, P<0.01, *P<0.001 relative to low/low TMAO/TML group; (E) Comparison of plasma levels of TML in free form versus protein-bound TML levels in random samples from both healthy subjects and subjects with cardiovascular disease, as indicated. The analyses were performed using R 3.4.1.

Figure 4:
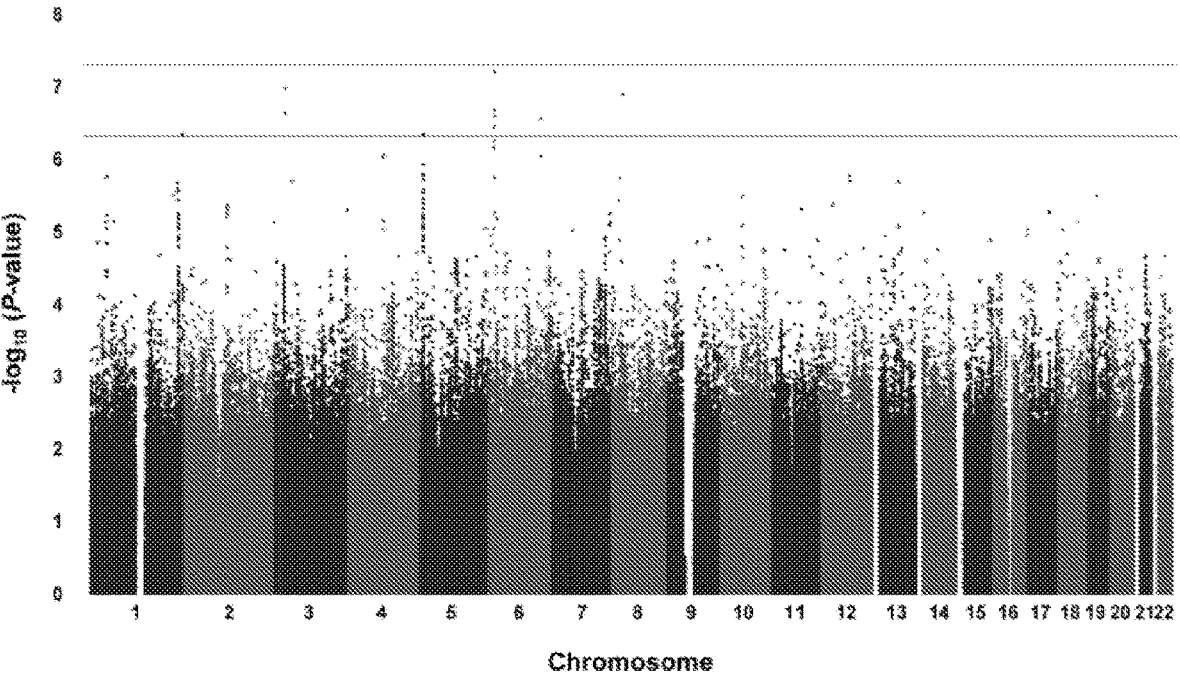

FIG. 4. Results of a GWAS for plasma TML levels in the GeneBank cohort. The Manhattan plot for plasma TML levels (N=1297 subjects) shows six suggestively associated loci on chromosomes 1q44, 3p24.1, 5p15.33, 6p24.1, 6q23.3, and 8p21.2. The genome-wide thresholds for significant (P=5.0×10⁻⁸) and suggestive (P=5.0×10⁻⁷) association are indicated by the horizontal red and blue lines, respectively. P-values were obtained using linear regression with natural log transformed values and adjustment for age and sex.

Figure 5:
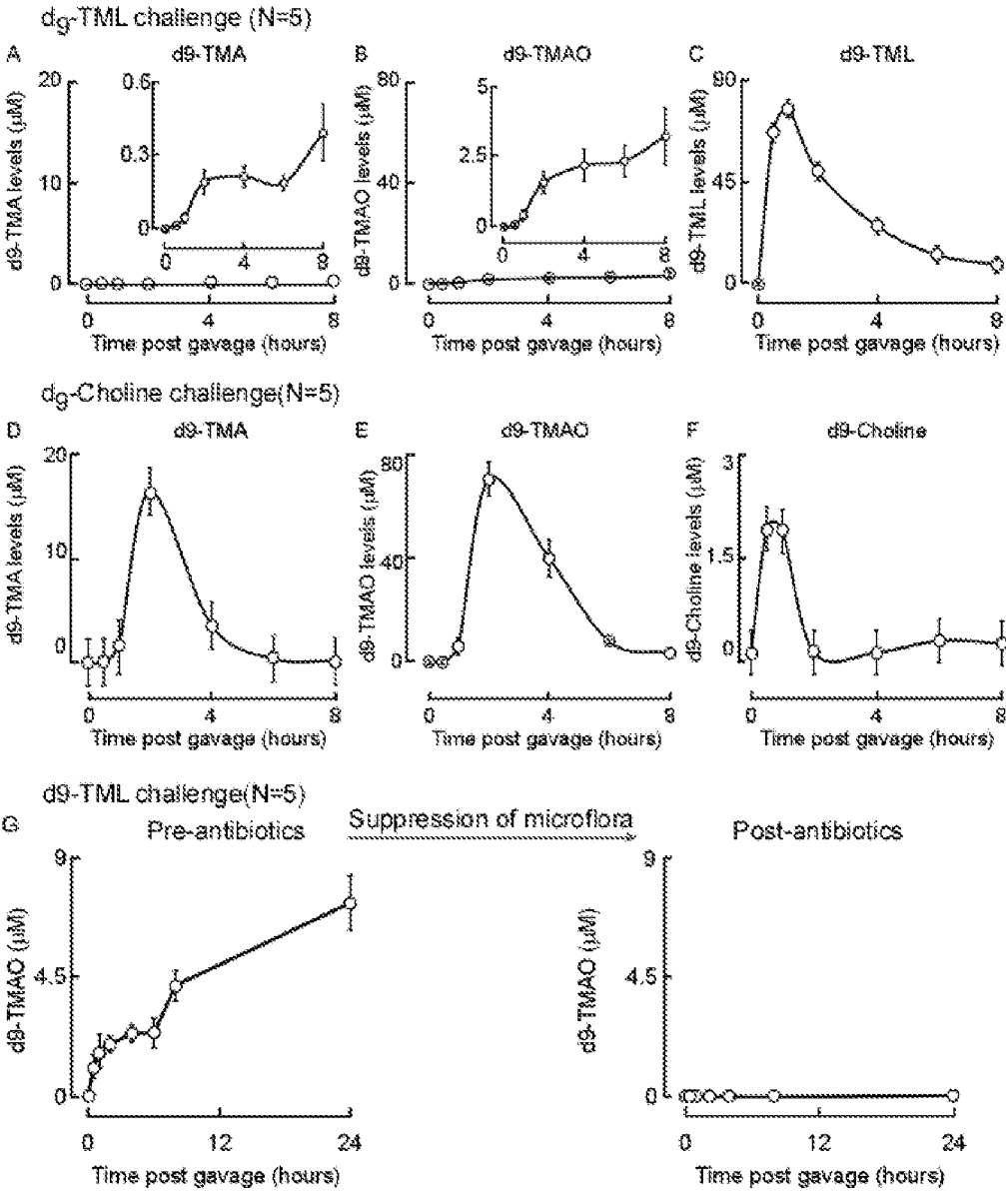

FIG. 5. d9-TML and d9-choline oral isotope tracer studies. Synthetic d9-TML or d9-choline was administered by gastric gavage to the indicated numbers of C57BL/6J mice and serial plasma levels of the indicated isotope labeled compounds were quantified by LC/MS/MS, as described under Methods in Example 1. (A, B, C) Plasma levels of d9-trimethylamine (d9-TMA), d9-TMAO and d9-TML are shown at the indicated times following oral challenge with time of d9-TML gavage designated as T=0. (D, E, F) Plasma d9-TMA, d9-TMAO or d9-choline at the indicated times following oral d9-choline challenge. (G) Plasma concentrations of d9-TMAO were also quantified by LC/MS/MS in C57BL/6J female mice at the indicated times following challenge with d9-TML via gastric gavage, either before or following 3 week administration of a cocktail of broad spectrum poorly absorbed antibiotics, as described under Methods in Example 1. All data are presented as means standard error.

Figure 6:
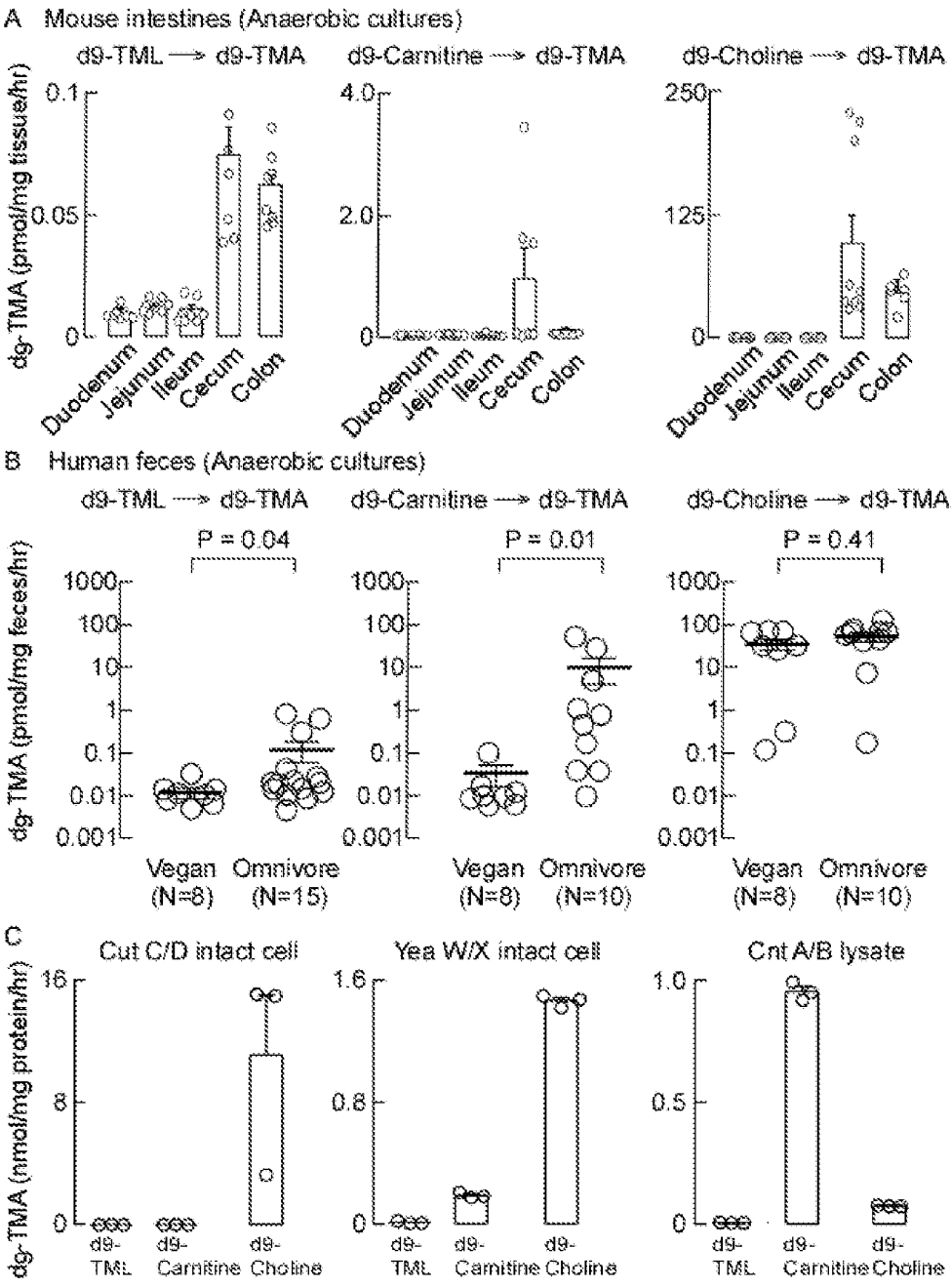

FIG. 6. Characterization of microbial TMA formation from TML versus alternative TMA-generating nutrients in mouse intestines, human fecal cultures and cloned microbial TMA lyases. (A) Intestines from conventionally reared C57BL/6J mice (N=7) were sectioned as indicated, incubated with either d9-TML, d9-carnitine or d9-choline anaerobically, and then production of d9-TMA quantified as described in Methods. (B) Human feces from vegans (N=8) and omnivores (N=10-15 as indicated) were incubated with either d9-TML, d9-carnitine or d9-choline anaerobically, and then production of d9-TMA quantified as described in Methods in Example 1. Student's t-test (2 tailed) was used to examine the difference between groups, all data are presented as means standard error. (C) Recombinant microbial TMA lyases were cloned and expressed, and then activity (production of d9-TMA) with the indicated d9-labeled substrates determined as described under Methods.

Figure 7:
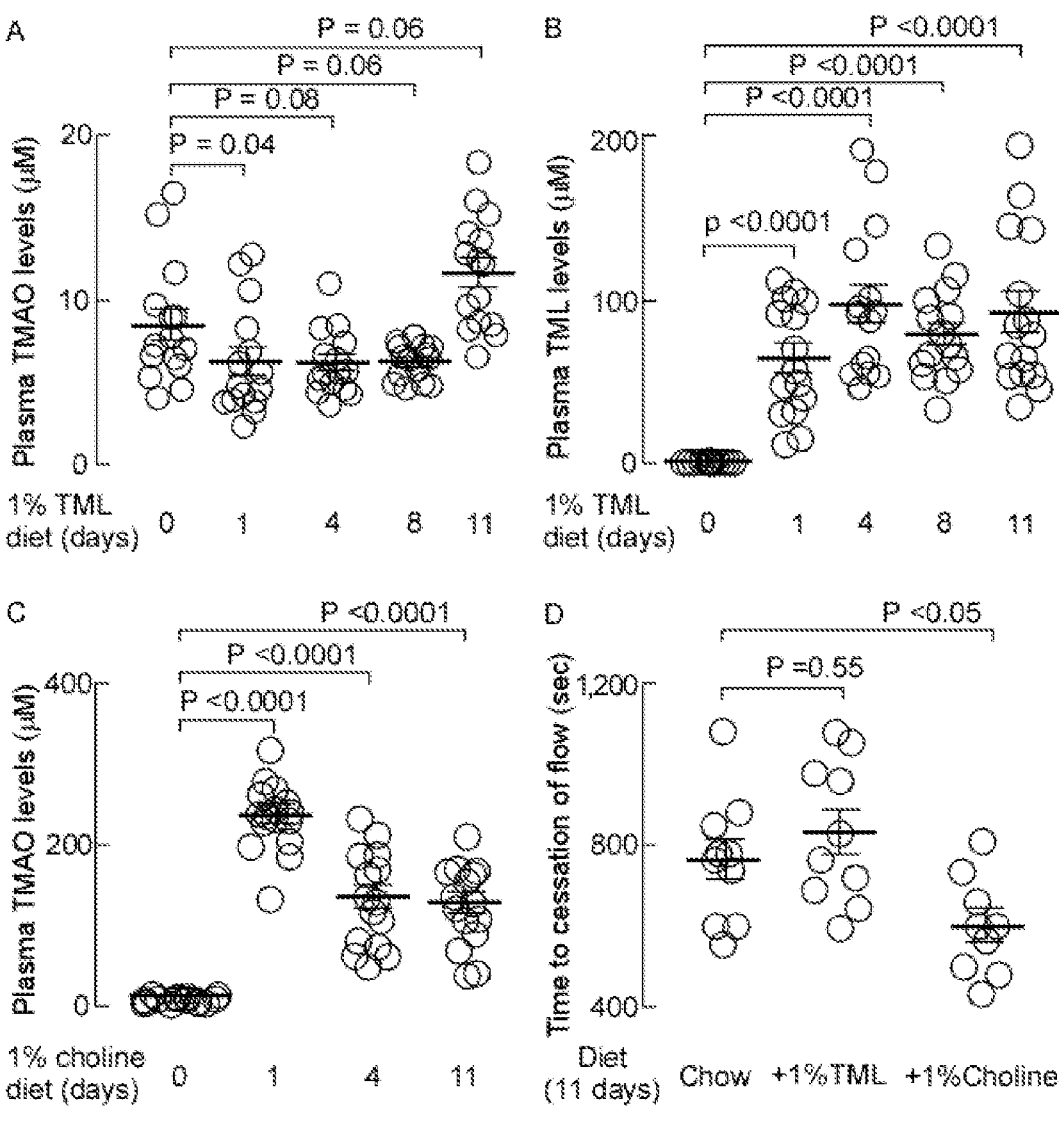

FIG. 7. Impact of TML versus choline supplemented diet on plasma levels of TML and TMAO, and in vivo thrombosis potential. Groups of mice (N=15) were placed on chemically defined diets supplemented with either 1% TML (A,B) or 1% choline (C) for 11 days as described under Methods in Example 1. At the indicated times, plasma levels of TMAO (A and C) or TML (B) were quantified by stable isotope dilution LC/MS/MS. (D) In addition, after 11 days of the indicated diet (N=10), the impact of supplemental dietary TML versus choline on both TMAO levels and in vivo thrombosis potential, as monitored using the FeCl3 carotid artery injury model, was determined as described under Methods. Plasma levels of metabolites after 11 days of the indicated diets were as follows: for 1% TML group— TMAO: 4.5±2.1 μM; TML: 37.0±15.5 μM. For 1% choline group—TMAO: 90.6±55.1 μM; TML: 0.8±0.4 μM. For chemically defined chow group—TMAO: 2.6±1.0 μM; TML: 0.9±0.4 μM. Student's t-test (2 tailed) was used to examine the difference between groups, all data are presented as means±standard error.

Figure 8:
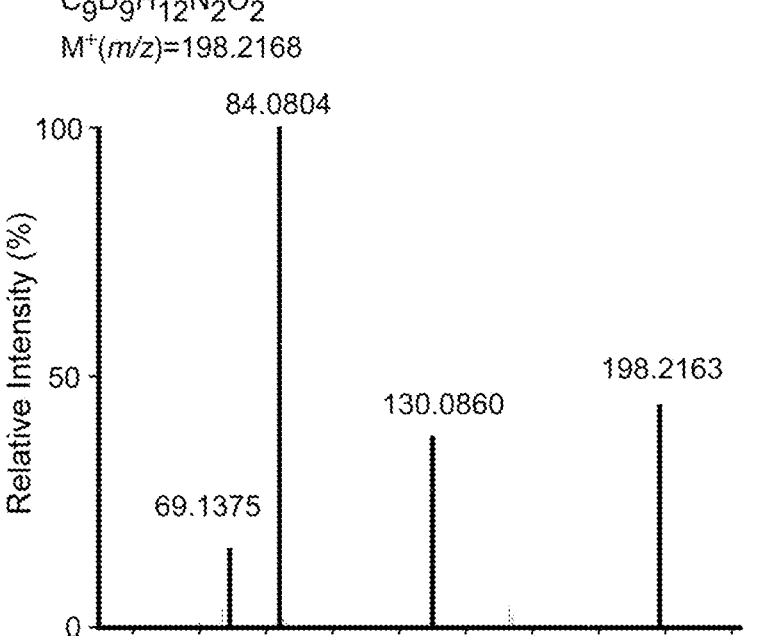
Figure 8:
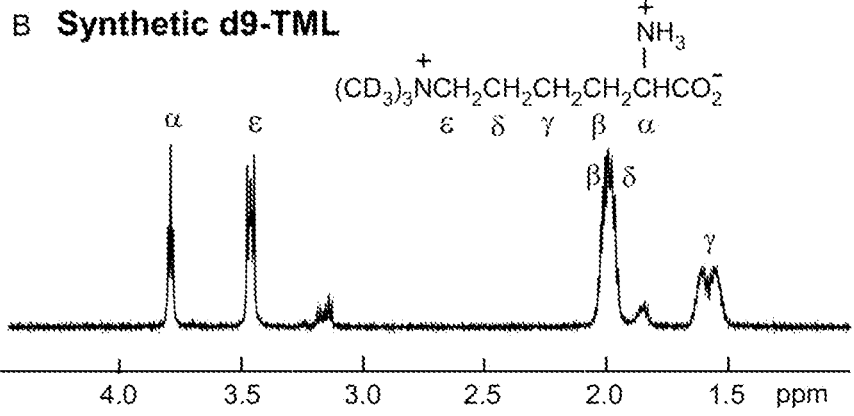

FIG. 8. Structural confirmation of synthetic d9(trimethyl)-N6-trimethyl-lysine. d9-TML was synthesized and purified as described under Methods. Its structure was confirmed by both high resolution MS and ¹H NMR. (A) MS/MS CID spectrum in positive mode of d9(trimethyl)-TML. (B) ¹H NMR spectrum of synthetically prepared d9-TML.

Figure 9:
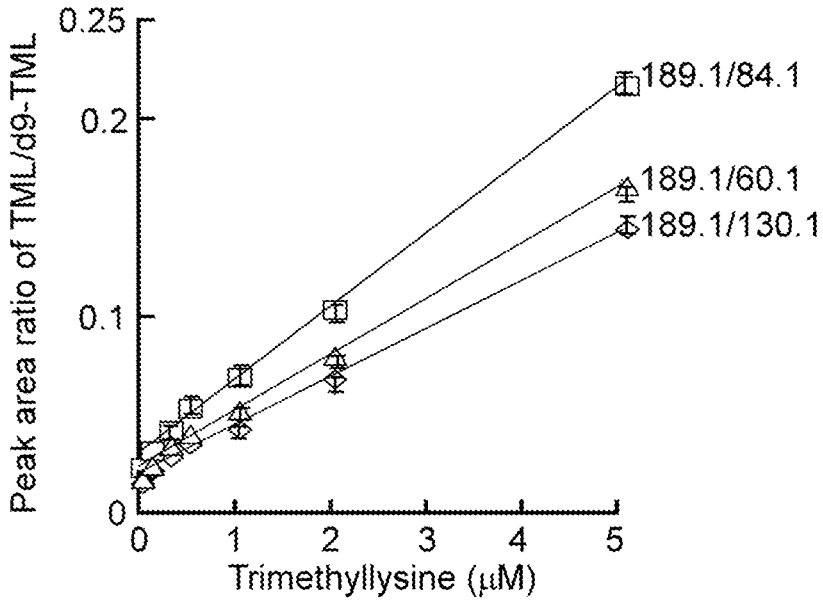

FIG. 9. Standard curves for LC/ESI/MS/MS analysis of N6-trimethyl-lysine (TML) within plasma matrix. All data are presented as means standard error (n=3). Numbers to the right of the curves indicate the parent->daughter ion transitions monitored in multiple reaction monitoring mode.

Figure 10:
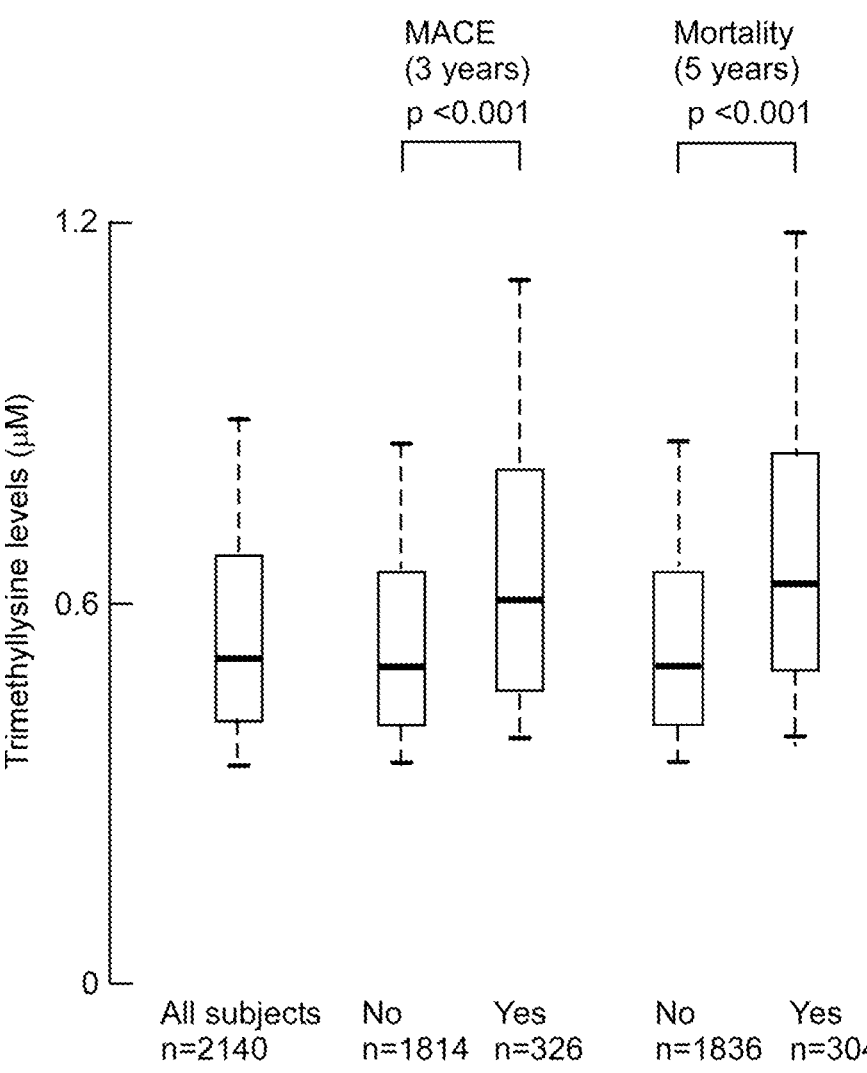

FIG. 10. Plasma TML levels in sequential stable subjects undergoing elective diagnostic cardiac evaluations. Subjects (n=2140 total) were divided into groups as indicated based on whether (Yes) or not (No) they experienced an incident major adverse cardiac event (MACE; MI, stroke or death), or died over the indicated period of follow-up. In the box-whisker plot, the upper and lower boundaries of the box represent the 25th and 75th percentiles, the median is marked by a horizontal line inside the box, and the TMAO in the cohort.

Figure 11:
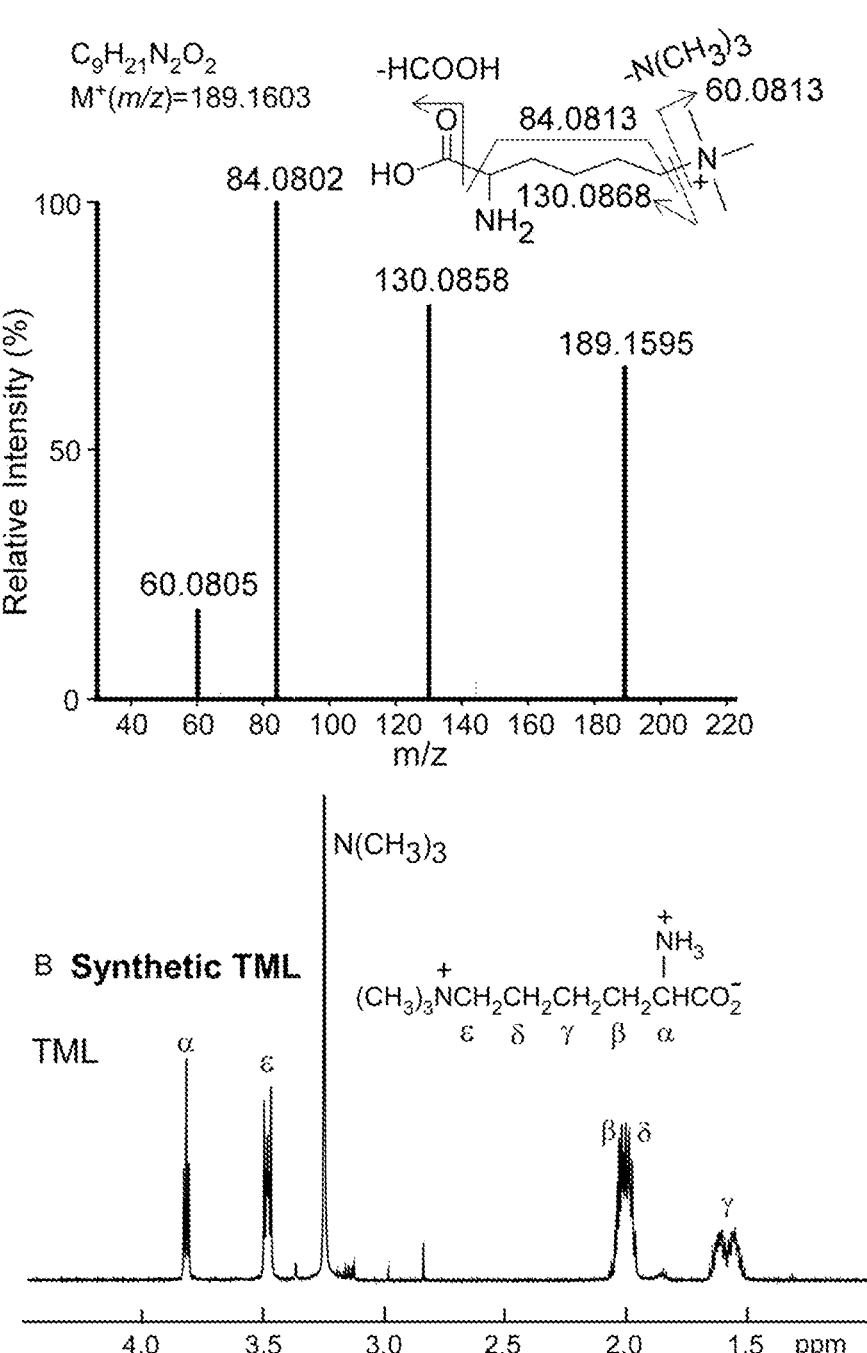

FIG. 11. Structural confirmation of synthetic N6-trimethyl-lysine. TML was synthetized and purified as described under Methods in Example 1. TML structure was confirmed by both high resolution MS and $^1$H NMR. (A) MS/MS CID spectra in positive mode of TML; (B) $^1$H NMR spectra of TML, N(CH$_3$)$_3$ at 3.25 ppm was observed.

Figure 12:
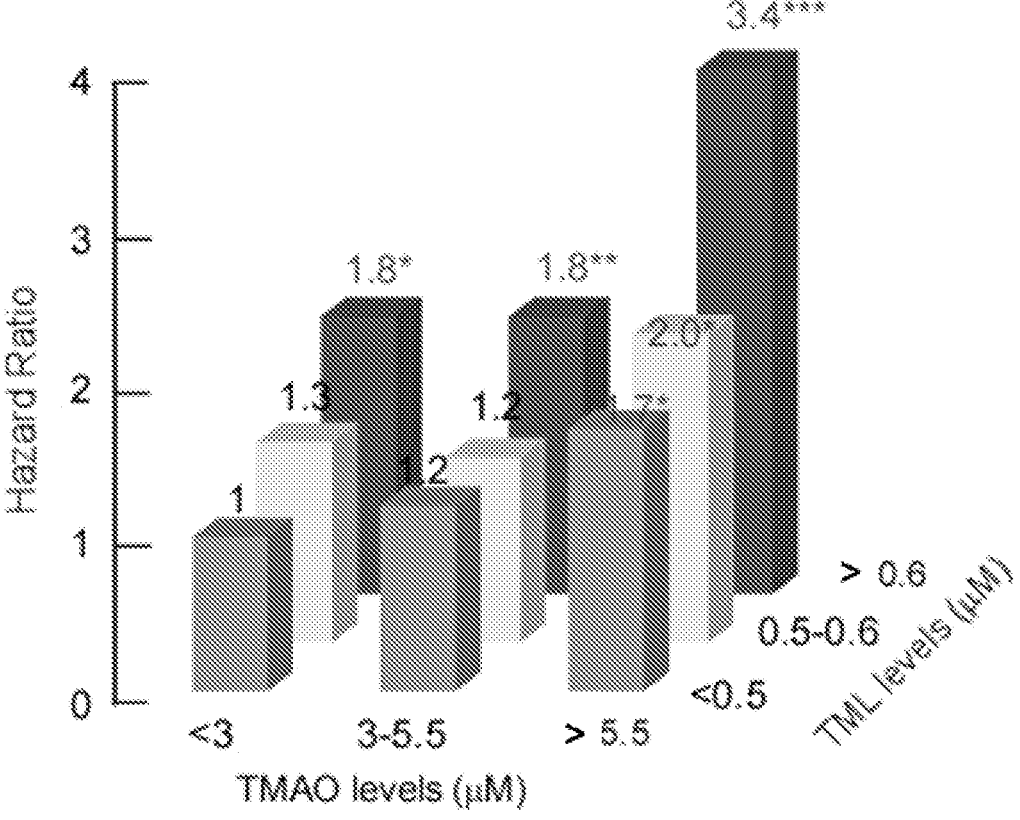

FIG. 12 shows a bivariate histogram providing a tertile analysis for the combination of TMAO and TML vs MACE.

Figure 13:
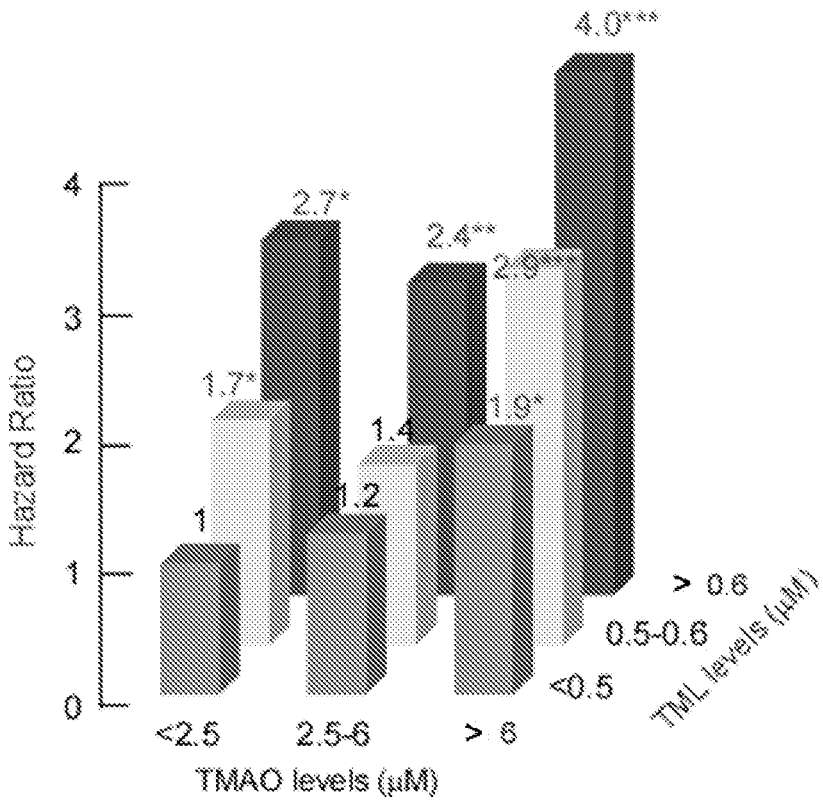

FIG. 13 shows a bivariate histogram providing a cut-off analysis for the combination of TMAO and TML vs MACE.

Figure 14:
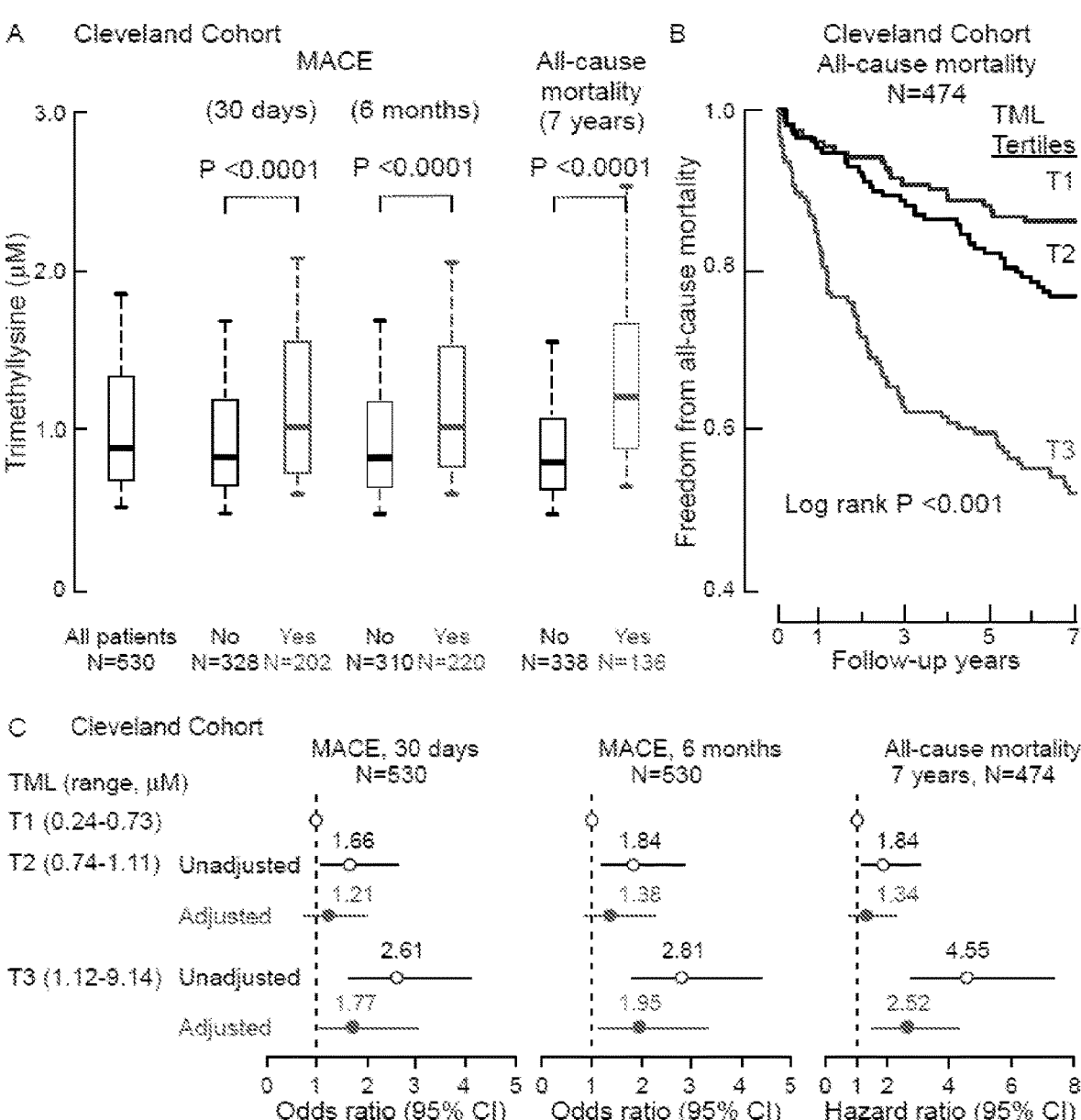

FIG. 14 shows that systemic levels of TML are associated with incident CVD risks in the entire Cleveland suspected ACS Cohort. (A) Box-Whisker plots of TML levels among patients presenting with chest pain indicating the relationship of TML with (Yes) and without (No) incident major adverse cardiac events (MACE) (MI, stroke, the need for revascularization, or all-cause mortality) and mortality over follow-up periods. (B) Kaplan-Meier plot depicting 7-year risk for all-cause mortality stratified by the tertiles of TML levels. (C) Forest plots illustrating the odds of MACE at 30 days and 6 months and the risk of all-cause mortality by 7 years according to the tertiles of TML levels. Symbols represent odds ratios or hazard ratios, and the 5-95% confidence interval is indicated by line length. Odds ratios were calculated using multivariable logistic regression modeling and hazard ratios by Cox modeling using adjustments for age, sex, high density lipoprotein cholesterol (HDL-C), low density lipoprotein cholesterol (LDL-C), smoking, history of diabetes mellitus and hypertension, and indices of renal function (eGFR).

Figure 15:
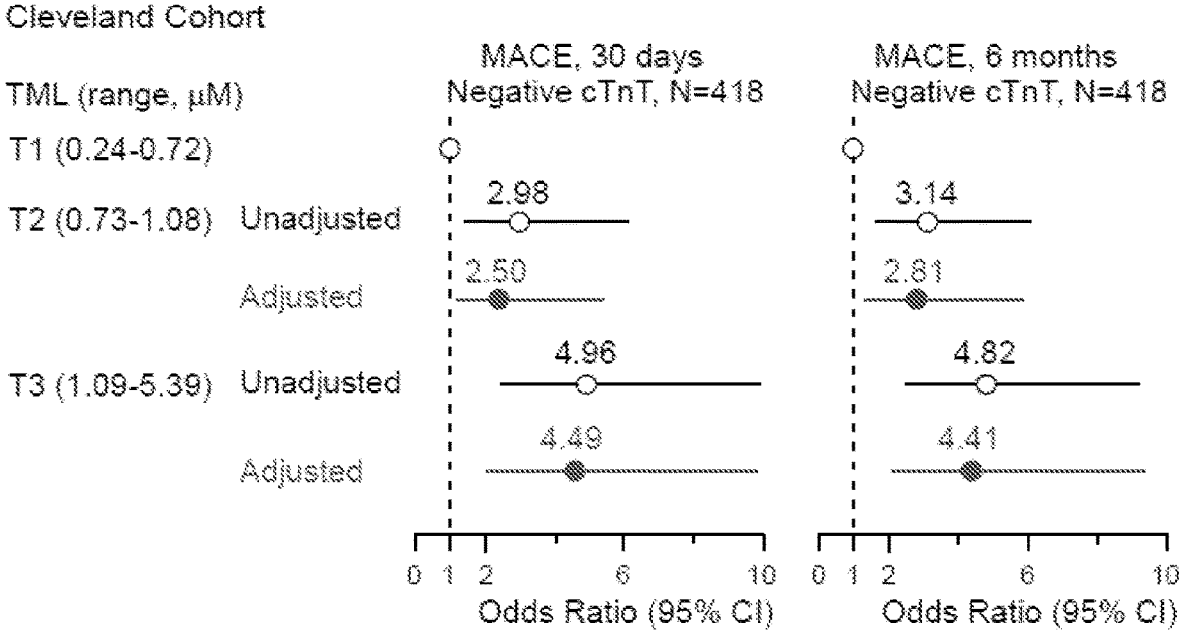

FIG. 15 shows the association of plasma TML levels with incident MACE for patients persistently negative for Troponin T. Forest plots indicating the risks of incident MACE at 30 days and 6 months according to TML levels ranked by tertiles among patients persistently negative for Troponin T test (cTnT<0.1 μg/L) in the Cleveland Cohort. Symbols represent odds ratios and the 5-95% confidence interval is indicated by line length. Odds ratios were calculated using multivariable logistic regression modeling using adjustments for age, sex, HDL-C, LDL-C, smoking, history of diabetes mellitus hypertension, and indices of renal function (eGFR).

Figure 16:
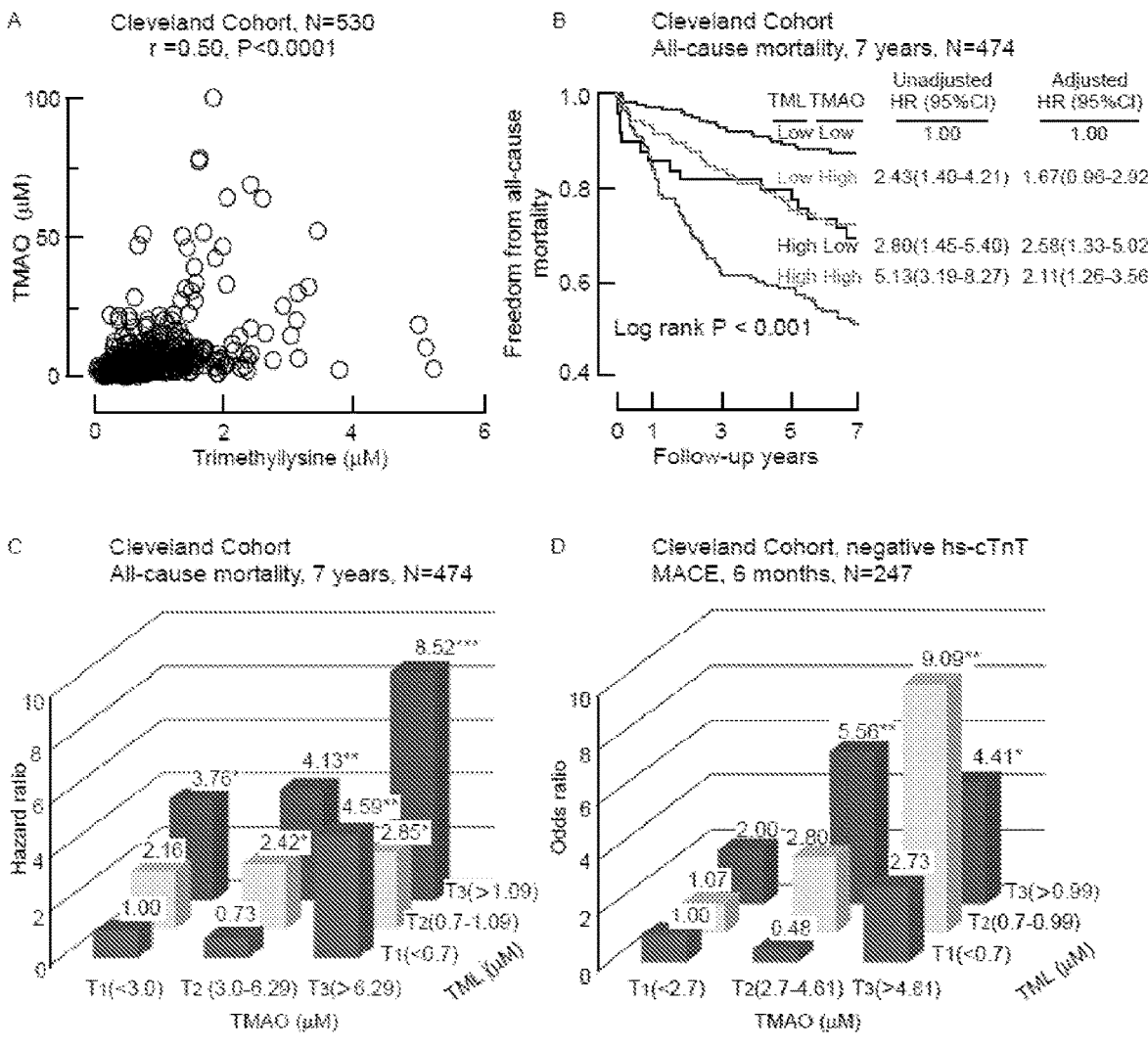

FIG. 16 shows plasma TML levels in relation to both incident CVD risks and TMAO in Cleveland cohort. (A) Correlation between plasma levels of TML and TMAO in the entire Cleveland Cohort. (B) Kaplan-Meier plot illustrating the relationship between plasma TML and risk of incident 7-year risk for mortality according to TML and TMAO levels where each marker is categorized above vs below the median level in the cohort, median plasma concentration of TML (0.89 μM) and TMAO (4.28 μM) within the cohort was used to stratify patients as 'high' (≥median) or 'low' (<median) values, also shown are hazard ratio (95% confidence interval) (HR (95% CI)) for the indicated TML and TMAO grouping using either an unadjusted model, or following adjustments for traditional cardiovascular risk factors (age, sex, HDL-C, LDL-C, smoking, diabetes mellitus, hypertension) and indices of renal function (eGFR). (C) Plot of unadjusted Hazard Ratio for incident 7-year mortality risk stratified by tertiles (low, intermediate and high) of TMAO (cutoff values 3.0 and 6.29 μM) and TML (cutoff values of 0.7 and 1.09 μM). *P<0.05, P<0.01, *P<0.001 relative to low/low TMAO/TML group. (D) Plot of unadjusted Odds Ratio for 6-month MACE stratified by the tertiles which indicated low, intermediate and high levels of TMAO (cutoff values 2.7 and 4.61 μM) and TML (cutoff values of 0.7 and 0.99 μM) among patients who were below the 99th percentile cut-off on hs-cTnT (N=247). *P<0.05, **P<0.01 relative to low/low TMAO/TML group.

Figure 17:
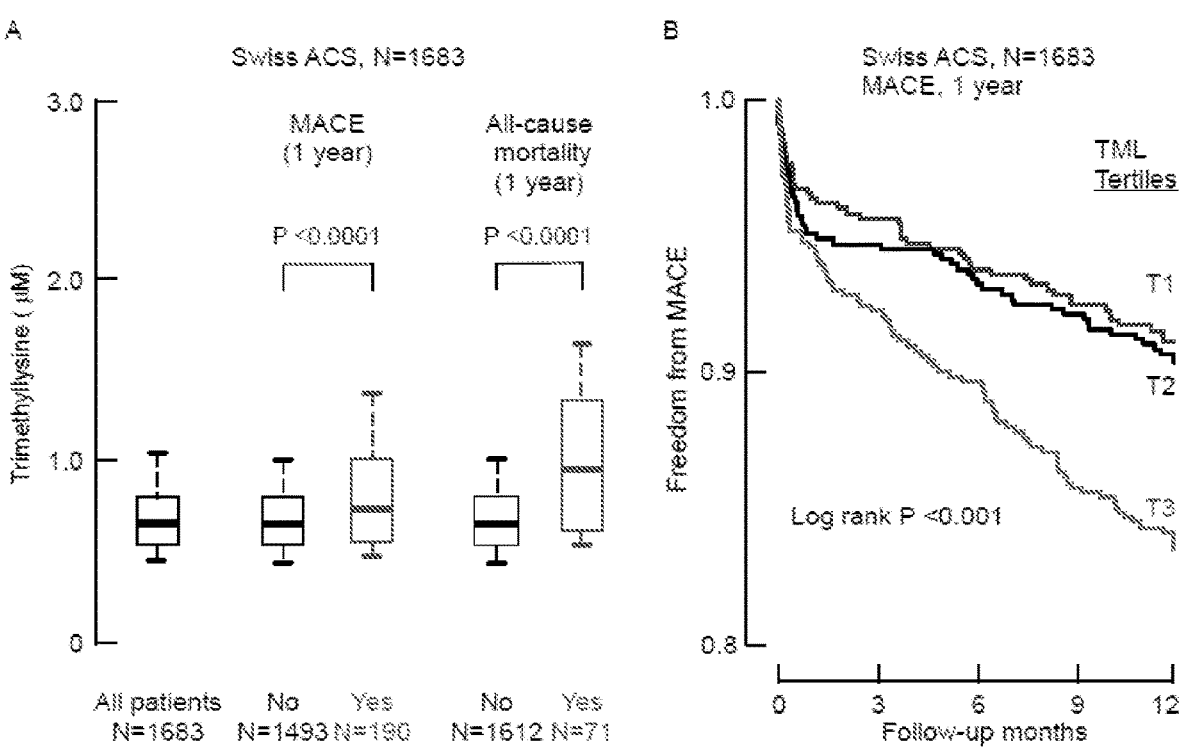
Figure 17:
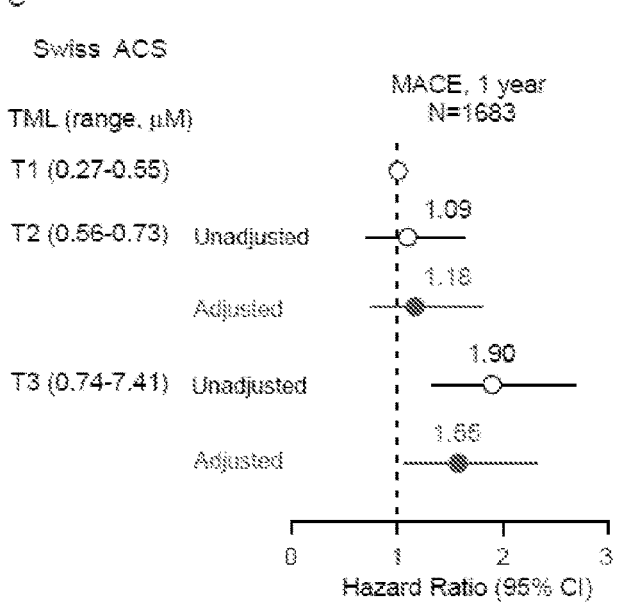
Figure 17:
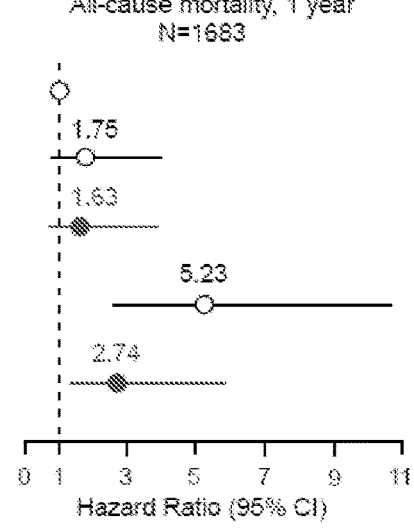

FIG. 17 shows the association of systemic levels of TML with incident CVD risks in the multicenter Swiss ACS Cohort. (A) Box-Whisker plots of TML levels among ACS patients depicting the relation of TML with (Yes) and without (No) incident MACE and mortality in 1 year. (B) Kaplan-Meier plots illustrating 1-year MACE risk stratified by the tertiles of TML levels. (C) Forest plots indicating the risks of incident MACE and mortality according to the tertiles of TML levels in one year. Symbols represent hazard ratios and the 5-95% confidence interval is indicated by line length. Hazard ratios by Cox modeling using adjustments for age, sex, HDL-C, LDL-C, smoking, history of diabetes mellitus and hypertension, and indices of renal function (eGFR).

Figure 18:
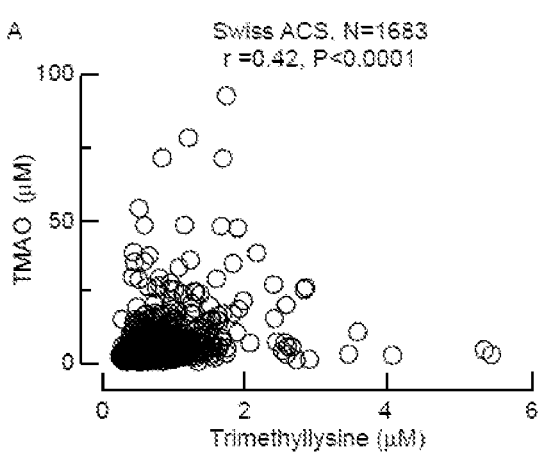
Figure 18:
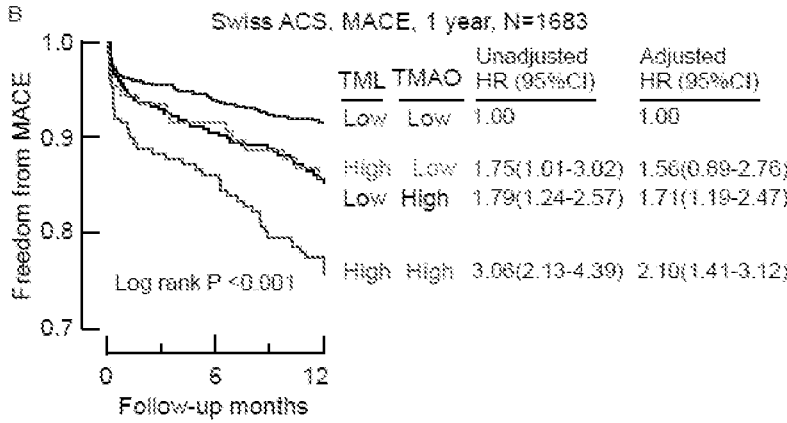
Figure 18:
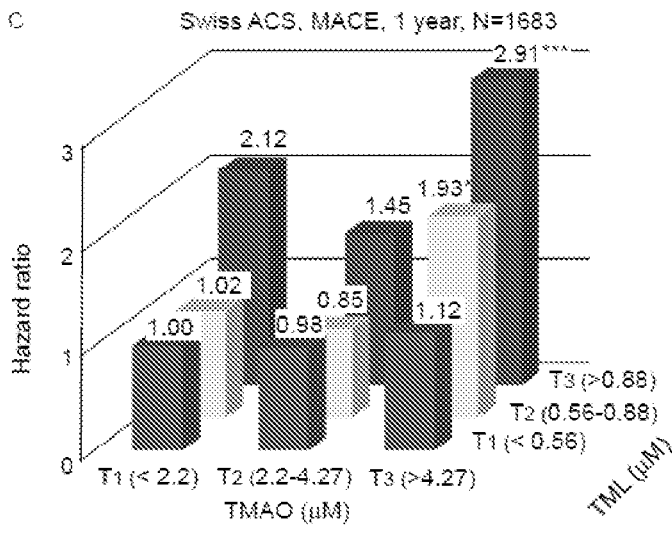

FIG. 18 shows the relationship between plasma TML and both incident CVD risks and TMAO in Swiss ACS cohort. (A) Correlation between plasma levels of TML and TMAO in the entire Swiss ACS Cohort (N=1683). (B) Kaplan-Meier estimates indicating the relationship between plasma TML and risk of incident 1 year MACE risk according to TML and TMAO levels where each marker is categorized above vs below indicated cutoff in the cohort, cutoff plasma concentration of TML (0.88 μM) and TMAO (4.27 μM) within the cohort was used to stratify patients as 'high' (≥cutoff) or 'low'(<cutoff) values, also shown are ratio (95% confidence interval) (HR (95% CI)) for the indicated TML and TMAO grouping using either an unadjusted model, or following adjustments for traditional cardiovascular risk factors (age, sex, HDL-C, LDL-C, smoking, diabetes mellitus, hypertension) and indices of renal function (eGFR). (C) Plot of Hazard Ratio for incident 1-year MACE risk stratified by indicated low, intermediate and high levels of TMAO (cutoff values 2.2 and 4.27 μM) and TML (cutoff values of 0.56 and 0.88 μM). *P<0.05, P<0.01, *P<0.001 relative to low/low TMAO/TML group.

Figure 19:
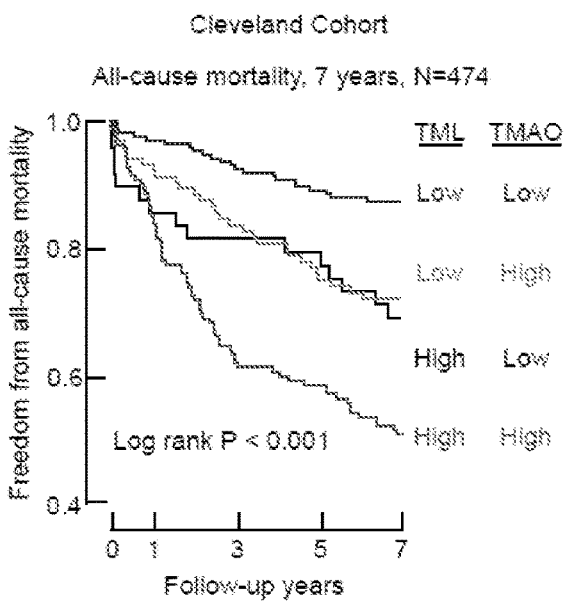
Figure 19:
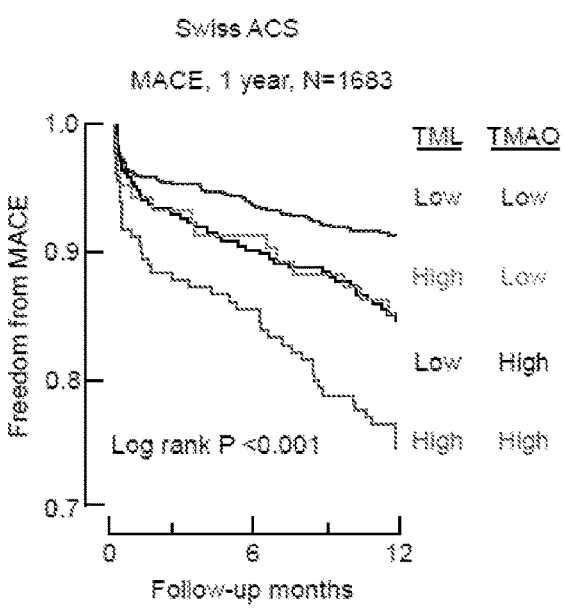

FIG. 19 shows plasma TML levels, alone and additive with TMAO, predict both near- and long-term CVD risks in patients who present with ACS in two independent cohorts: The Cleveland Cohort, and the Swiss ACS Cohort.

Figure 20:
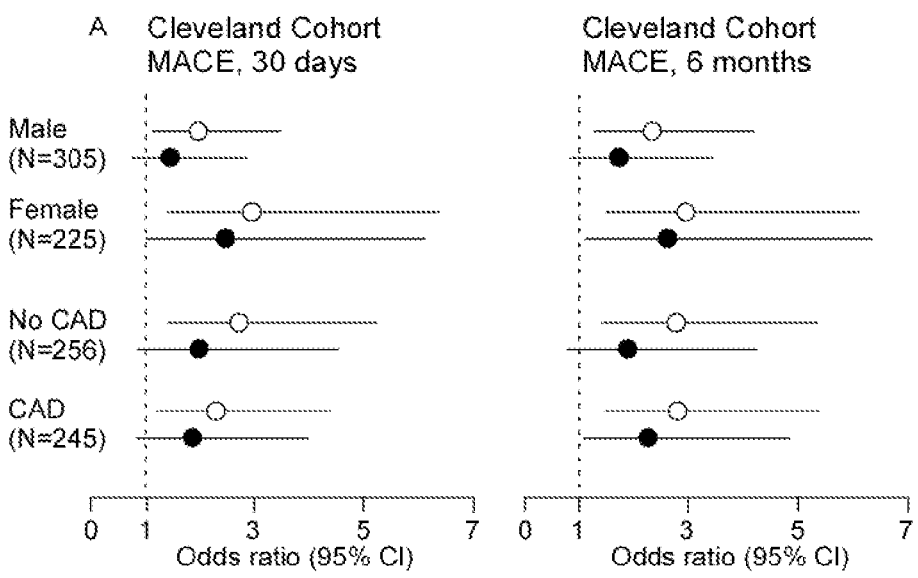
Figure 20:
Figure 20:
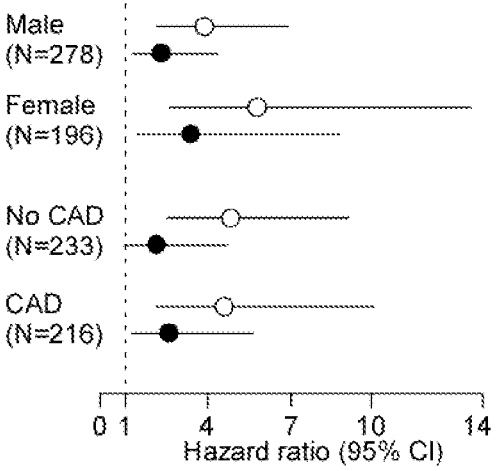

FIG. 20 shows sub-cohort analyses of TML and 30-day, 6-month MACE and 7-year all-cause mortality in sex specific cohort and the presence or absence of CAD cohort in Cleveland Cohort. (A) Forest plot of the odds ratio of major adverse cardiac events (30 days and 6 months) and tertile 3 (vs tertile 1) of TML both unadjusted (open circles) and after adjusting for age, sex, high density lipoprotein cholesterol (HDL-C), low density lipoprotein cholesterol (LDL-C), smoking, history of diabetes mellitus, and hypertension, and indices of renal function (eGFR) (closed circles). (B) Forest plots of the odds ratio of 7-year all-cause mortality and tertile 3 (vs tertile 1) of TML both unadjusted (open circles) and after adjusting for age, sex, high density lipoprotein cholesterol (HDL-C), low density lipoprotein cholesterol (LDL-C), smoking, history of diabetes mellitus, and hypertension, and indices of renal function (eGFR) (closed circles).

Figure 21:
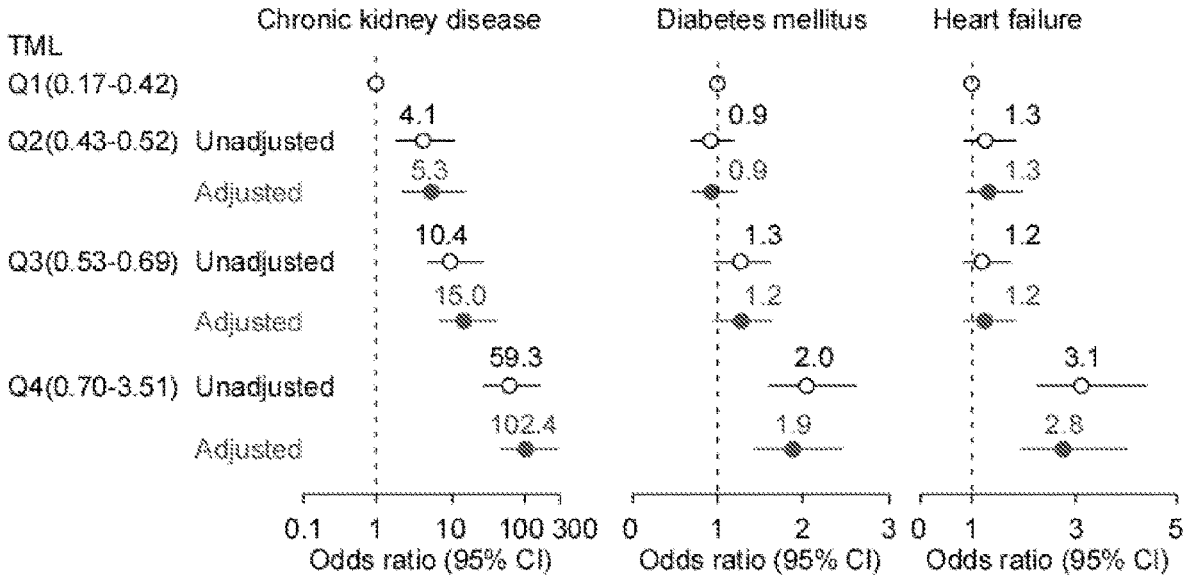

FIG. 21 shows that elevated trimethyllysine (TML) was associated with increased chronic kidney disease (CKD), diabetes mellitus and heart failure in the Stable Angiographic Cohort (N=2,140). FIG. 21 shows forest plots illustrating the odds of CKD (left panel), diabetes mellitus (central panel) and heart failure (right panel) according to the quartiles of TML levels. CKD defined as eGFR <60 mL/min per 1.73 m2 (CKD stage 3 or beyond). Symbols represent odds ratios (OR) (unadjusted OR, open black circles; adjusted OR, filled circles), and the 5-95% confidence interval is indicated by line length. Odds ratios were calculated using multivariable logistic regression modeling using adjustments for age, sex, high density lipoprotein cholesterol (HDL-C), low density lipoprotein cholesterol (LDL-C), smoking, hypertension, diabetes mellitus and C-reactive protein level.

Figure 22:
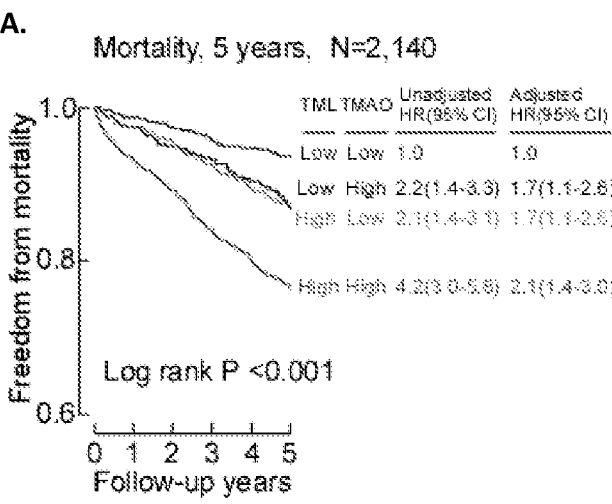
Figure 22:
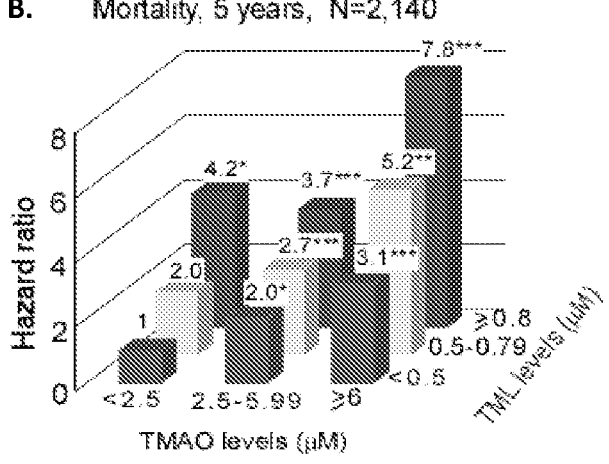

FIG. 22 shows TML provides independent and additive prognostic value in combination with TMAO for prediction of incident MACE and all-cause mortality risks. (A) incident (5-year) mortality risks according to TML and TMAO levels where each marker is categorized above vs below the median level in the Validation Cohort (N=2,140). Also shown are hazard ratio (95% confidence interval) (HR (95% CI)) for the indicated TML and TMAO grouping using either an unadjusted model, or following adjustments for traditional cardiovascular risk factors (age, sex, HDL-C, LDL-C, smoking, diabetes mellitus, hypertension), high sensitivity C-reactive protein level, estimated glomerular filtration rate (eGFR), history of CAD and medications. Median plasma concentration of TML (0.53 µM) and TMAO (3.69 µM) within the cohort was used to stratify subjects as 'high' (≥median) or 'low' (<median) values; (B) Plots of Hazard Ratio for 5-year mortality risks stratified by indicated low, intermediate and high levels of TMAO (cutoff values 2.5 and 6 µM) and TML (cutoff values of 0.5 and 0.8 µM). *P<0.05, P<0.01, *P<0.001 relative to low/low TMAO/TML group.

Figure 23:
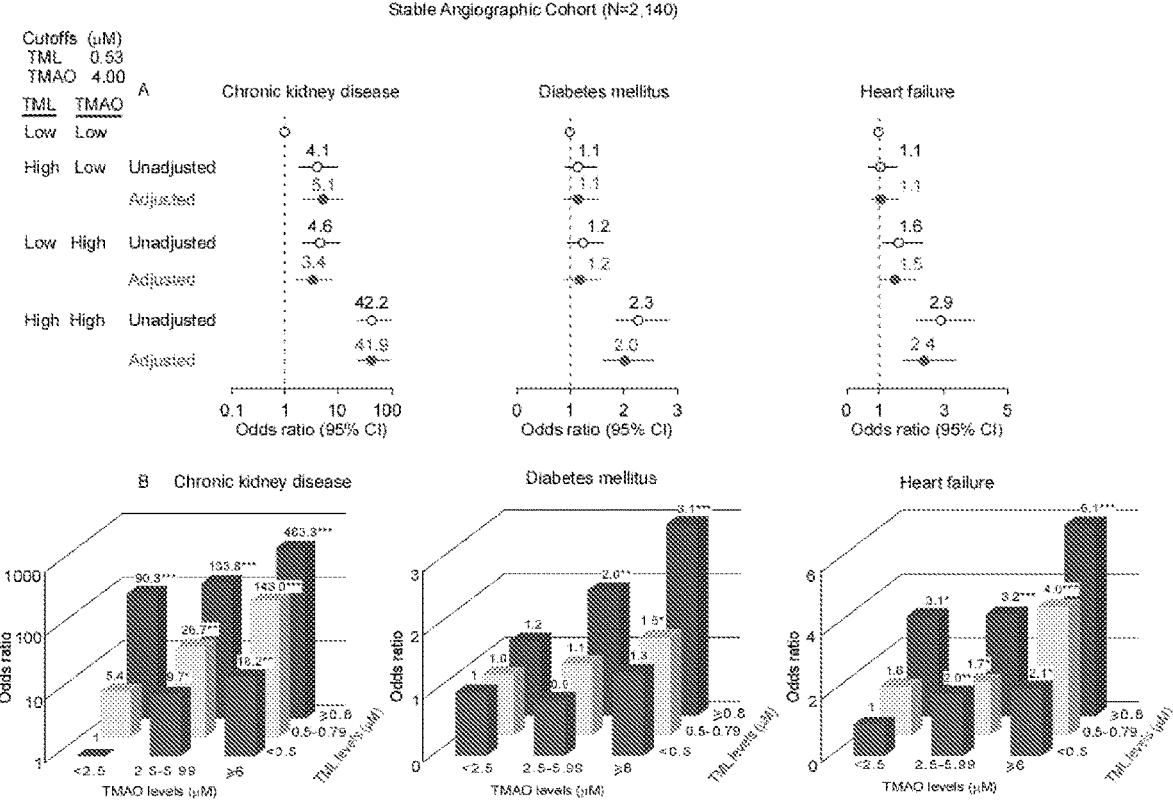

FIG. 23 shows plasma TML in relation to both TMAO and the odds of CKD, diabetes and heart failure in the Stable Angiographic Cohort (N=2,140). (A) Plots of unadjusted Odds Ratio for CKD (left panel), diabetes mellitus (central panel) and heart failure (right panel) according to TML and TMAO levels where each marker is categorized above vs below the median level in the cohort, median plasma concentration of TML (0.53 µM) and TMAO (4.00 µM) within the cohort was used to stratify patients as 'high' (≥median) or 'low' (<median) values, also shown are odds ratio (95% confidence interval) (OR (95% CI)) for the indicated TML and TMAO grouping using either an unadjusted model (OR, open back circles), or following adjustments for traditional cardiovascular risk factors (age, sex, HDL-C, LDL-C, smoking, diabetes mellitus, hypertension) and C-reactive protein level (OR, filled red circles). (B) Plots of unadjusted Odds Ratio for CKD (left panel), diabetes mellitus (central panel) and heart failure (right panel) stratified by indicated low, intermediate and high levels of TMAO (cutoff values 2.5 and 6.0 µM) and TML (cutoff values of 0.5 and 0.8 µM). *P<0.05, P<0.01, *P<0.001 relative to low/low TMAO/TML group.

DEFINITIONS

As used herein, the terms "cardiovascular disease" (CVD) or "cardiovascular disorder" are terms used to classify numerous conditions affecting the heart, heart valves, and vasculature (e.g., veins and arteries) of the body and encompasses diseases and conditions including, but not limited to arteriosclerosis, atherosclerosis, myocardial infarction, acute coronary syndrome, angina, congestive heart failure, aortic aneurysm, aortic dissection, iliac or femoral aneurysm, pulmonary embolism, primary hypertension, atrial fibrillation, stroke, transient ischemic attack, systolic dysfunction, diastolic dysfunction, myocarditis, atrial tachycardia, ventricular fibrillation, endocarditis, arteriopathy, vasculitis, atherosclerotic plaque, vulnerable plaque, acute coronary syndrome, acute ischemic attack, sudden cardiac death, peripheral vascular disease, coronary artery disease (CAD), peripheral artery disease (PAD), and cerebrovascular disease.

As used herein, the term "atherosclerotic cardiovascular disease" or "disorder" refers to a subset of cardiovascular disease that include atherosclerosis as a component or precursor to the particular type of cardiovascular disease and includes, without limitation, CAD, PAD, cerebrovascular disease. Atherosclerosis is a chronic inflammatory response that occurs in the walls of arterial blood vessels. It involves the formation of atheromatous plaques that can lead to narrowing ("stenosis") of the artery, and can eventually lead to partial or complete closure of the arterial opening and/or plaque ruptures. Thus atherosclerotic diseases or disorders include the consequences of atheromatous plaque formation and rupture including, without limitation, stenosis or narrowing of arteries, heart failure, aneurysm formation including aortic aneurysm, aortic dissection, and ischemic events such as myocardial infarction and stroke The terms "individual," "host," "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. In some embodiments, the subject is specifically a human subject.

As used herein "heart failure" refers to when the heart is unable to pump sufficiently to maintain blood flow to meet the body's needs. Signs and symptoms of heart failure commonly include shortness of breath, excessive tiredness, and leg swelling. The shortness of breath is usually worse with exercise, while lying down, and may wake the person at night. A limited ability to exercise is also a common feature. Common causes of heart failure include coronary artery disease including a previous or current myocardial infarction (heart attack), high blood pressure, atrial fibrillation, valvular heart disease, excess alcohol use, infection, and cardiomyopathy of an unknown cause.

DETAILED DESCRIPTION OF THE INVENTION

The present invention relates to systems, kits, and methods for identifying subjects with increased levels of N6-trimethyl-lysine (TML) or the combination of TML and trimethylamine-n-oxide (TMAO), as well as methods of determining risk of disease (e.g., kidney disease or heart failure) based on such levels. In certain embodiments, subjects with elevated TML or TML and TMAO are treated with a therapeutic (e.g., one that inhibits the TMA/FMO3/TMAO pathway). It is noted that N6-trimethyl-lysine (TML), is also known as (S)-2-amino-6-(trimethylammonio)Hexanoate; (S)-2-amino-6-(trimethylammonio) Hexanoic acid; delta-Trimethyllysine; epsilon-N-Trimethyl-L-lysine;epsilon-Trimethyl-L-lysine; N(6),N(6),N(6)-Trimethyl-L-lysine;epsilon-N-Trimethyl-R-lysine;epsilon-Trimethyl-R-lysine; N(6),N(6),N(6)-Trimethyl-R-lysine; epsilon-N-Trimethyl-lysine; epsilon-Trimethyl-lysine; N(6),N(6),N(6)-Trimethyl-lysine; (S)-5-amino-5-Carboxy-N,N,N-trimethyl-1-pentanaminium; Trimethyllysine; 6-N-Trimethyl-L-lysine; 6-N-Trimethyl-R-lysine; 6-N-Trimethyl-lysine; epsilon-N-Trimethyl-lysine; TRIMETHYLLYSINE; Trimethyllysine hydroxide, inner salt, (S)-isomer; Trimethyllysine, (+−)-isomer; Trimethyllysine hydroxide, inner salt, (+−)-isomer; Trimethylly-sine chloride, (S)-isomer; and Trimethyllysine chloride, (R)-isomer.

In some embodiments, provided herein are methods for treatment and/or prevention of disease (e.g., kidney disease, diabetes, heart failure, NASH, and/or cardiovascular disease) in patients identified as having elevated levels of TML, or both TMAO and TML, using compounds and or procedures that inhibit the TMA/FMO3/TMAO pathway. In certain embodiments, such compounds and procedures are selected from the group consisting of i) 3,3-dimethyl-1-butanol (DMB) or a DMB derivative or related compound (e.g., as shown in Formula IV); ii) acetylsalicylic acid with or without an enteric coating; iii) an acetylsalicylic acid derivative with or without an enteric coating; iv) a flavin monooxygenase 3 (FMO3) inhibitor; v) a gut TMA lyase inhibitor; vi) fecal microbiota transplantation; vii) delivery of acetylsalicylic acid or derivative thereof directly to the colon or cecum of the subject; viii) a probiotic or prebiotic that reduces TMA production in the gut; ix) an antiplatelet agent; x) a TMA and/or TMAO sequestering agent; xi) a moiety from Table 1; xii) a compound comprising at least one of: N,N-dimethylethanolamine (DMEA), N-methyl-ethanolamine (MEA), ethanolamine (EA), trimethylsilyl ethanol, P-choline, and P,P,P-trimethyl ethanolphosphine; xiii) 3-(2,2,2-trimethylhydraziniumyl) propionate (also known as mildronate, THP, MET-88, Meldonium or Quar-terine); and xiv) a compound of Formulas I-III (as described in U.S. Pat. Pub. 2018/0000754, which is herein incorporated by reference in its entirety, particularly for Formulas I-III).

I. DMB Derivatives and Formula IV

In certain embodiments, the therapeutic used to treat the subject is DMB, related compound, or a compound of Formula IV. Formula IV is as follows:

$$W_3C - \underset{\underset{CH_3}{|}}{\overset{\overset{CH_3}{|}}{Y}} - [CH_2]_n - \overset{XR}{\underset{ZR,}{|}}$$

wherein n is an integer, or n is 0, indicating that $CH_2$ is not present;

wherein Y is C, N, Si, P, S, Ge, Sn, Pb, P, As, Sb, or Bi;

wherein each W is independently selected from: H, Cl, F, Br, or I (e.g., $W_3C=CH_3$, $CH_2Cl$, $CH_2Fl$, $CH_2Br$, $CH_2I$, $CF_3$, $CCl_3$, $CBr_3$, $CI_3$, or $CHCl_2$);

wherein X is O or S and the corresponding bond is either present or absent or double, wherein R is absent, H, an alkyl group, alkenyl group, alkynyl group, phenyl group, amide, alkylamide, or a benzyl group;

wherein Z is C, $CH_2$, CH, NH, O or S, wherein XR is alternatively, H, an ester, thioester, or thio-nester; glycerol, or one of the following three formulas:

$$O - \overset{\overset{O}{\|}}{\underset{\underset{OR'}{|}}{P}} - OR', \quad O - \overset{\overset{O}{\|}}{\underset{\underset{O}{|}}{P}} - O \diagdown\diagup\diagdown OR', \quad or$$

$$[CH_2]_n - \overset{\overset{X'}{\|}}{C} - X'R';$$

wherein R' is H, an alkyl group, alkenyl group, alkynyl group, phenyl group, or a benzyl group; and wherein X' is O, or S. In certain embodiments, R is amide or alkylamide, and Z is an O, and Z as a double bond O—a carboxylic acid). In some embodiments, the two methyl groups extending from Y are linked by an alkyl or ether to form a 4-6 member ring.

In certain embodiments, the composition comprises dim-ethylbutanol or a compound shown in FIGS. 20-23 of U.S. application Ser. No. 13/915,299, which is herein incorporated by reference in its entirety. In some embodiments, the composition comprises a compound of Formula IV (or N,N-dimethylethanolamine (DMEA), N-methyletha-nolamine (MEA), ethanolamine (EA), trimethylsilyl etha-nol, and P,P,P-trimethyl ethanolphosphine) containing food or beverage. In further embodiments, the composition com-prises food or liquid containing a compound of Formula IV (or N,N-dimethylethanolamine (DMEA), N-methyletha-nolamine (MEA), ethanolamine (EA), trimethylsilyl etha-nol, and P,P,P-trimethyl ethanolphosphine) selected from the group consisting of but not limited to: olive oil, extra virgin olive oil, grape seed oil, yeast containing food, and red wine.

In some embodiments, Formula IV has a formula selected from the group consisting of:

$$H_3C - \underset{\underset{CH_3}{|}}{\overset{\overset{CH_3}{|}}{Y}} - [CH_2]_n \diagup\diagdown XR, \qquad H_3C - \underset{\underset{CH_3}{|}}{\overset{\overset{CH_3}{|}}{Y}} - [CH_2]_n \overset{\overset{X}{\|}}{C} XR,$$

$$H_3C - \underset{\underset{CH_3}{|}}{\overset{\overset{CH_3}{|}}{Y}} - [CH_2]_n \overset{XR}{\underset{}{|}} [CH_2]_n XR, \quad and$$

$$H_3C - \underset{\underset{CH_3}{|}}{\overset{\overset{CH_3}{|}}{Y}} - [CH_2]_n - O - \overset{\overset{O}{\|}}{\underset{\underset{O}{|}}{P}} - O \diagdown\diagup\diagdown OR.$$

In other embodiments, Formula IV has a formula selected from the group consisting of:

$$H_3C - \underset{\underset{CH_3}{|}}{\overset{\overset{CH_3}{|}}{C}} \diagup\diagdown\diagup OH, \qquad H_3C - \underset{\underset{CH_3}{|}}{\overset{\overset{CH_3}{|}}{Si}} \diagup\diagdown\diagup OH,$$

2,2-dimethyl-1-butanol (DMB)     2-Trimethylsitylethanol $$H_3C - \underset{\underset{CH_3}{|}}{\overset{\overset{CH_3}{|}}{P}} \diagup\diagdown\diagup OH, \quad and \quad H_3C - \overset{\overset{S}{|}}{S} \diagup\diagdown\diagup OH.$$

P-Choline

In certain embodiments, Formula IV has a formula selected from the group consisting of:

$$H_3C - \underset{\underset{CH_3}{|}}{\overset{\overset{CH_3}{|}}{Y}} \diagup\diagdown\diagup O \overset{\overset{O}{\|}}{C} R, \qquad H_3C - \underset{\underset{CH_3}{|}}{\overset{\overset{CH_3}{|}}{Y}} - [CH_2]_n \diagup\diagdown\diagup OH,$$

-continued

In some embodiments, Formula IV has a formula selected from the group consisting of:

L-Carnitine

D-Carnitine 5,5-dimethyl-3-hydroxyhexanoic Acid

4-Trimethylsilyl-3-hydroxybutyric Acid

P-Carnitine

In further embodiments, Formula IV has a formula selected from the group consisting of:

-continued

II. Acetylsalicylic Acid Derivatives and Related Compounds

In some embodiments, the acetylsalicylic acid derivative or related compound is selected from the group consisting of: 4-Methylsalicylic acid, 5-(acetylamino)-2-hydroxybenzoic acid; Salicylic acid, sodium salt, 4-Aminosalicylic acid, 3-Methylsalicylic acid, 3-Nitrosalicylic acid, 1-Hydroxy-2-naphthoic acid, 2-Hydroxyethyl salicylate, 5-Bromosalicylic acid, 5-Methylsalicylic acid, 5-Aminosalicylic acid, 2,4-Dihydroxybenzoic acid, 2,4-Dimethoxybenzoic acid, 3-Hydroxy-2-naphthoic acid, 5-Nitrosalicylic acid, Phenyl salicylate, Ethyl salicylate, 5-Iodosalicylic acid, Methyl salicylate, 5,5'-Methylenedisalicylic acid, Pamoic acid, 2-Ethoxybenzoic acid, 2,6-Dihydroxybenzoic acid, 2,3-Dihydroxybenzoic acid, Ochratoxin A, 5-Chlorosalicylic acid, 4-Fluorosalicylic acid, Methyl 5-fluoro-2-hydroxybenzoate, 2,4,5-Trimethoxybenzoic acid, 2,5-Dihydroxybenzoic acid, Acetylsalicylsalicylic acid, Salicylsalicylic acid, 6-Methylsalicylic acid, Aluminon, 3-Aminosalicylic acid, 2,3,4-Trimethoxybenzoic acid, o-Anisic acid, Isopropyl salicylate, 3,5-Dinitrosalicylic acid, 2,3,4-Trihydroxybenzoic acid, 5-Formylsalicylic acid, 2-Hydroxy-4-nitrobenzoic acid, Lithium 3,5-diiodosalicylate, 4-Fluorosulfonyl-1-hydroxy-2-naphthoic acid, 3-Methoxysalicylic acid, Methyl 1-hydroxy-2-naphthoate, Carminic acid, Carmine (pure, alum lake of carminic acid), Carmine (high purity biol.stain, alum lake of carminic acid), 2,6-Dimethoxybenzoic acid, 2,3-Dimethoxybenzoic acid, Chrome Azurol S, Alizarin Yellow R sodium salt, 3-Chlorosalicylic acid, 2-(trifluoromethoxy) benzoic acid, Methyl 2,4-dimethoxybenzoate, Methyl 2,6-dihydroxybenzoate, Methyl 2,4-dihydroxybenzoate, Triethanolamine salicylate, 2-Ethoxynaphthoic acid, 4-Methoxysalicylic acid, 5-Methoxysalicylic acid, 2,5-Dimethoxybenzoic acid, 3,5 Dibromosalicylic acid, 6-Methoxysalicylic acid, 5-Chloro-o-anisic acid, Chromoxane Cyanine R, 3-Hydroxy-4-(2-hydroxy-4-sulfo-1-naphthylazo) naphthalene-2-carboxylic acid, indicator grade ethyl 2,3-dihydroxybenzoate, Methyl 5-iodosalicylate, methyl 5-chloro-2-hydroxybenzoate, Methyl 4-acetamido-5-chloro-2-methoxybenzoate, 2-(acetyloxy)-3-methylbenzoic acid, 2-(acetyloxy)-3-methylbenzoic acid, 1,4-Benzodioxan-5-carboxylic acid, 2-Methoxy-5-(trifluoromethyl)benzoic acid, 4-Chlorosalicylic acid, Methyl 4-methoxysalicylate, 1,3-benzodioxole-4-carboxylic acid, 5-Sulfosalicylic acid dihydrate, 5-Sulfosalicylic acid dihydrate, 5-Sulfosalicylic acid dihydrate, Mordant Yellow 10, 4-Amino-5-chloro-2-methoxybenzoic acid, Methyl 5-acetylsalicylate, 5-chloro-sulfonyl-2-hydroxybenzoic acid, methyl 2-[2-(dimethyl-amino)ethoxy]benzoate, alpha-Apo-oxytetracycline, beta-Apo-oxytetracycline, 3,5-Di-tert-butylsalicylic acid, Methyl 3,5-dibromo-2-hydroxybenzoate, 2-(3-methoxyphenoxy)benzoic acid, Methyl 3-nitrosalicylate, Methyl 5-methylsali-cylate, methyl 4-amino-2-methoxybenzoate, chroman-8-carboxylic acid, methyl 2,5-di(2,2,2-trifluoroethoxy)benzoate, 2,3 dihydrobenzo[b]furan-7-carboxylic acid, methyl 3-amino-2-hydroxybenzoate, 3-chloro-2,6-dime-thoxybenzoic acid, 3-Hydroxyphthalic anhydride, 5-Bromo-2,3-dihydrobenzo[b]furan-7-carboxylic Acid, 2,2-dimethyl-2,3-dihydro-1-benzofuran-7-carboxylic acid, 6-Fluorosalicylic acid, 2,4,6-Trihydroxybenzoic acid mono-hydrate, 3-bromo-2,6-dimethoxybenzoic acid, 3-bromo-2,6-dimethoxybenzoic acid, 3,5-dichloro-2,6-dimethoxybenzoic acid, Lavendustin A, 2-Fluoro-6-methoxybenzoic acid, 5-Bromo-2,4-dihydroxybenzoic acid monohydrate, 3-chloro-2,6-dimethoxy-5-nitrobenzoic acid, methyl 4,7-di-bromo-3-methoxy-2-naphthoate, 2-(trifluoromethoxy)tere-phthalic acid, 2-methoxy-4,6-di(trifluoromethyl)benzoic acid, 2-[2-(dimethylamino)ethoxy]benzoic acid, 2-[(5-chloro-3-pyridyl)oxy]-5-nitrobenzoic acid, 6-fluoro-4H-1,3-benzodioxine-8-carboxylic acid, 3-Methoxy-4-(methoxy-carbonyl)phenylboronic acid pinacol ester, 3-Methoxy-4-(methoxycarbonyl)phenylboronic acid, 2-(tetrahydropyran-4-yloxy)benzoic acid, pentafluorophenyl 2-(tetrahydro-2H-pyran-4-yloxy)benzoate, 3-Hydroxy-4-(methoxycarbonyl)phenylboronic acid pinacol ester, and 3-Formylsalicylic acid hydrate.

III. Antibiotics

In certain embodiments, that antibiotic includes, but is not limited to, Ampicillin; Bacampicillin; Carbenicillin Indanyl; Mezlocillin; Piperacillin; Ticarcillin; Amoxicillin-Clavu-lanic Acid; Ampicillin-Sulbactam; Benzylpenicillin; Cloxa-cillin; Dicloxacillin; Methicillin; Oxacillin; Penicillin G; Penicillin V; Piperacillin Tazobactam; Ticarcillin Clavulanic Acid; Nafcillin; Cephalosporin I Generation; Cefadroxil; Cefazolin; Cephalexin; Cephalothin; Cephapirin; Cephra-dine; Cefaclor; Cefamandol; Cefonicid; Cefotetan; Cefoxi-tin; Cefprozil; Ceftmetazole; Cefuroxime; Loracarbef; Cef-dinir; Ceftibuten; Cefoperazone; Cefixime; Cefotaxime; Cefpodoxime proxetil; Ceftazidime; Ceftizoxime; Ceftriax-one; Cefepime; Azithromycin; Clarithromycin; Clindamy-cin; Dirithromycin; Erythromycin; Lincomycin; Trolean-domycin; Cinoxacin; Ciprofloxacin; Enoxacin; Gatifloxacin; Grepafloxacin; Levofloxacin; Lomefloxacin; Moxifloxacin; Nalidixic acid; Norfloxacin; Ofloxacin; Spar-floxacin; Trovafloxacin; Oxolinic acid; Gemifloxacin; Per-floxacin; Imipenem-Cilastatin Meropenem; Aztreonam; Amikacin; Gentamicin; Kanamycin; Neomycin; Netilmicin; Streptomycin; Tobramycin; Paromomycin; Teicoplanin; Vancomycin; Demeclocycline; Doxycycline; Methacycline; Minocycline; Oxytetracycline; Tetracycline; Chlortetracy-cline; Mafenide; Silver Sulfadiazine; Sulfacetamide; Sulfa-diazine; Sulfamethoxazole; Sulfasalazine; Sulfisoxazole; Trimethoprim-Sulfamethoxazole; Sulfamethizole; Rifabu-tin; Rifampin; Rifapentine; Linezolid; Streptogramins; Qui-nopristin Dalfopristin; Bacitracin; Chloramphenicol; Fosfo-mycin; Isoniazid; Methenamine; Metronidazol; Mupirocin; Nitrofurantoin; Nitrofurazone; Novobiocin; Polymyxin; Spectinomycin; Trimethoprim; Colistin; Cycloserine; Capreomycin; Ethionamide; Pyrazinamide; Para-aminosali-cyclic acid; and Erythromycin ethylsuccinate.

18

IV. Halomethyl and Morpholine Compounds

In certain embodiments, the halomethyl and morpholines compounds are as shown in Table 1 below.

TABLE 1

Formula I is as follows:

Formula (I)

wherein R1 is selected from:

wherein Z is selected from: C, CH, CH2, or O;

wherein R2 and R3 are independently selected from C1-C4 alkyl, allyl, propargyl, or CH2 when part of an aliphatic, carbocyclic, or heterocyclic ring system;

wherein R4 is selected from: H, C1-C4 alkyl, allyl, alkyl carboxyl, alkyl carboxylate, alkyl ester, hydroxy alkyl, alkoxy alkyl, propargyl, amine, or amino alkyl;

wherein R5 is selected from: H, or C1-C4 alkyl;

wherein R6 is independently selected from hydroxyl, C1-C4 alkoxy, or oxygen when part of a ring system, and;

wherein R7 is selected from: H, C1-C4 alkyl, or is absent when the carboxylate ion exists as part of a betaine, inner salt, or Zwitterion form;

wherein Y+ is a quaternary nitrogen;

wherein X– is a pharmaceutically acceptable anion; and wherein n is 1, 2, 3 or 4, and including any acceptable salts or solvates thereof.

Formula II is as follows:

Formula (II)

wherein R$^8$ is:

Br, Cl, F, I, wherein R9 and R10 are independently selected from: C1-C4 alkyl, wherein R11 is propargyl, wherein Y+ is a quaternary nitrogen, wherein X– is a pharmaceutically acceptable anion, and wherein n is 1, 2, 3 or 4, and including any acceptable salts or solvates thereof.

Formula III is as follows:

Formula (III)

R$^{12}$ is selected from:

wherein W is CH2, or O;

wherein R13 and R14 are independently selected from: C1-C4 alkyl, or propargyl;

wherein R15 is selected from: C1-C4 alkyl, hydroxy ethyl, or propargyl;

wherein R5 is selected from: H, or C1-C4 alkyl;

wherein R6 is independently selected from: hydroxyl, C1-C4 alkoxy, or oxygen when part of a ring system;

wherein R16 is selected from: H, C1-C4 alkyl, or a negative charge when [O] exists as a carboxylate anion;

wherein Y+ is a quaternary nitrogen;

wherein X– is a pharmaceutically acceptable anion; and wherein n is 1, 2, 3 or 4, and including any acceptable salts or solvates thereof.

In some embodiments, compounds of Formulas I-III are shown in Table 13. In table 13, compounds marked by * fall under Formula (I); compounds marked by ˆ fall under Formula (II), and compounds marked by # fall under Formula (III). Salt forms may include, but are not limited to, chloride, bromide, or iodide.

TABLE 13

| ID | * or #, or ^ | Structure | Compound |
|---|---|---|---|
| 1 | *, # | | 2-(methoxycarbonyl)-N,N-dimethyl-N-(prop-2-yn-1-yl)prop-2-en-1-aminium |
| 2 | *, # | | 4-carboxy-N,N-dimethyl-N-(prop-2-yn-1-yl)butan-1-aminium |
| 3 | *, # | | N-(2-hydroxyethyl)-2,2-dimethoxy-N,N-dimethylethan-1-aminium |
| 4 | *, # | | N-(2,2-dimethoxyethyl)-N,N-dimethylprop-2-yn-1-aminium |
| 5 | *, # | | N-(2,2-dihydroxyethyl)-N,N-dimethylprop-2-yn-1-aminium |
| 6 | *, # | | N-(2,3-diethoxyethyl-N,N-dimethylprop-2-yn-1-aminium |
| 7 | *, # | | 5-carboxy-N,N-dimethyl-N-(prop-2-yn-1-yl)pentan-1-aminium |
| 8 | *, # | | 2-carboxy-N,N-dimethyl-N-(prop-2-yn-1-yl)prop-2-en-1-aminium |
| 9 | *, # | | N-(2-amino-2-oxoethyl)-N,N-dimethylprop-2-yn-1-aminium |
| 10 | *, # | | 2-carboxy-N-(2-hydroxyethyl)-N,N-dimethylprop-2-en-1-aminium |
| 11 | *, # | | 2-cyano-N-(2-hydroxyethyl)-N,N-dimethylprop-2-en-1-aminium |
| 12 | *, # | | 2-cyano-N,N-dimethyl-N-(prop-2-yn-1-yl)prop-2-en-1-aminium |
| 13 | *, # | | N-(3-methoxy-2,3-dioxopropyl)-N,N-dimethylprop-2-yn-1-aminium |

TABLE 13-continued

| ID | * or #, or ˆ | Structure | Compound |
|---|---|---|---|
| 14 | *, # | | 8-(2-cyanoallyl)-8-methyl-8-azabicyclo[3.2.1]octan-8-ium |
| 15 | *, # | | 2-aminoethyl-dimethyl-prop-2-ynyl-ammonium |
| 16 | * | | N-(2-hydroxyethyl)-N,N-dimethylbut-3-yn-1-aminium |
| 17 | * | | 4-hydroxy-1-methyl-1-(prop-2-yn-1-yl)piperidin-1-ium |
| 18 | * | | 8-methyl-8-(prop-2-yn-1-yl)-8-azabicyclo[3.2.1]octan-8-ium |
| 19 | * | | N-(carboxymethyl)-N,N-dimethylprop-2-yn-1-aminium |
| 20 | * | | N-(2-methoxy-2-oxoethyl)-N,N-dimethylprop-2-yl-1-aminium |
| 21 | * | | N-(2-hydroxyethyl)-N,N-dimethyl-2-propyn-1-aminium |
| 22 | * | | N-(2-hydroxyethyl)-N,N-dimethyl-2-butyn-1-aminium |
| 23 | * | | N,N-dimethyl-N-2-propenyl-2-propen-1-aminium |
| 24 | * | | 2-hydroxy-N,N-dimethyl-N-(oxiran-2-ylmethyl)ethan-1-aminium |
| 25 | * | | N-(2-hydroxyethyl)-N,N-dimethyl-2-propen-1-aminium |
| 26 | * | | N-(2-hydroxyethyl)-N,N-di(prop-2-yn-1-yl)prop-2-yn-1-aminium |
| 27 | * | | 2-(acryloyloxy)-N,N,N-trimethylethan-1-aminium |

TABLE 13-continued

| ID | * or #, or ^ | Structure | Compound |
|---|---|---|---|
| 28 | * | | N-(3-hydroxypropyl)-N,N-dimethylprop-2-yn-1-aminium |
| 29 | * | | N-(cyanomethyl)-2-hydroxy-N,N-dimethylethan-1-aminium |
| 30 | * | | N,N,N-tri(prop-2-en-1-yl)prop-2-en-1-aminium |
| 31 | * | | 2-(dimethyl(prop-2-yn-1-yl)ammonio)acetate |
| 32 | * | | [(E)-but-2-enyl]-(2-hydroxyethyl)-dimethyl-ammonium |
| 33 | * | | trimethyl(prop-2-ynyl)ammonium |
| 34 | * | | dimethyl-bis(prop-2-ynyl)ammonium |
| 35 | * | | allyl-(cyanomethyl)-dimethyl-ammonium |
| 36 | * | | cyanomethyl-dimethyl-prop-2-ynyl-ammonium |
| 37 | * | | allyl(trimethyl)ammonium |
| 38 | * | | methyl-tris(prop-2-ynyl)ammonium |
| 39 | * | | tetrakis(prop-2-ynyl)ammonium |
| 40 | ^ | | chloromethyl-dimethyl-prop-2-ynyl-ammonium |
| 41 | ^ | | bromomethyl-dimethyl-prop-2-ynyl-ammonium |

TABLE 13-continued

| ID | * or #, or ^ | Structure | Compound |
|---|---|---|---|
| 42 | ^ | | iodomethyl-dimethyl-prop-2-ynyl-ammonium |
| 43 | ^ | | 2-bromoethyl-dimethyl-prop-2-ynyl-ammonium |

In some embodiments, the compound used to treat a subject (e.g., with elevated TML and/or TMAO) is as shown in Formula V below, and as provided in U.S. Pat. Pub. 20170152222, which is herein incorporated by reference in its entirety.

Formula (V):

wherein
Y+ is selected from a quaternary nitrogen;
X− is any pharmaceutically acceptable salt;
n is selected from 1, 2 or 3;
R2 and R3 are independently selected from Cl-4 alkyl or bound together forming an aliphatic, aromatic or heterocyclic ring system;
R4 is selected from Cl-4 alkyl, alkenyl, alkynyl, alkoxy carbonyl, alkoxy dicarbonyl, acrylic, alkoxy, alkoxy alkyl, aryloxy alkyl, alkyl carboxylate as part of a betaine, inner salt, or Zwitterion form, halo alkyl, hydroxy alkyl, nitrile, or propargyl; and
R6 is selected from C1-4 alkyl, alkoxy, hydroxy, alkoxy alkyl, hydroxy alkyl, or epoxy; and including any acceptable salts or solvates thereof.

EXAMPLES

The following examples are for purposes of illustration only and are not intended to limit the scope of the claims.

Example 1

Untargeted Metabolomics Identifies N6-Trimethyl-Lysine, a TMAO-Producing Nutrient Precursor, is Associated with Incident Cardiovascular Disease Risk Using an untargeted metabolomics approach in initial (N=100 subjects) and replication cohorts (N=1,162), we discovered and structurally identified a plasma metabolite associated with cardiovascular disease (CVD) risks, N6-trimethyl-lysine (N6-trimethyl-lysine, TML). Stable isotope-dilution tandem-mass spectrometry analyses of an independent Validation Cohort (N=2,140) confirmed TML levels are independently associated with incident (3-year) major adverse cardiovascular event risks (Hazards Ratio (95% Confidence Interval); 2.4(1.7-3.4)) and incident (5-year) mortality risk (2.9(2.0-4.2)). Genome-wide association studies identified several suggestive loci for TML levels, but none reached genome-wide significance; and d9(trimethyl)-TML isotope tracer studies confirmed TML can serve as a nutrient precursor for gut microbiota-dependent generation of trimethylamine (TMA) and the atherogenic metabolite trimethylamine-N-oxide (TMAO). Although TML was shown to be abundant in both plant and animal-derived foods, mouse and human fecal cultures (omnivores and vegans) showed slow conversion of TML to TMA. Furthermore, unlike chronic dietary choline, TML supplementation in mice failed to elevate plasma TMAO or heighten in vivo thrombosis potential in vivo. Thus, TML is identified as a strong predictor of incident CVD risks in subjects and to serve as a dietary precursor for gut microbiota-dependent generation of TMAO; however, TML does not appear to be a major microbial source for TMAO generation in vivo.

Untargeted metabolomics analyses of biological samples hold promise as a discovery platform for the potential identification of new metabolites and pathways linked to pathophysiological processes and disease susceptibility (1-7). For example, in previous studies an untargeted mass spectrometry approach was used to discover an association between plasma levels of the metabolite trimethylamine N-oxide (TMAO) and incident risk for cardiovascular disease (CVD) (1). Subsequent studies revealed TMAO is produced via metaorganismal pathways initiated by ingestion of trimethylamine (TMA) containing dietary nutrients, including phosphatidylcholine (1), choline (1), betaine (1), carnitine (8) and gamma-butyrobetaine (9). Following ingestion, gut microbial fermentation of the TMA-containing nutrient results in TMA release, which upon delivery to the liver via the portal circulation is converted into TMAO via host enzymes (1). Further, mechanistic animal models have shown that dietary provision of TMA-containing nutrients can result in the gut microbiota-dependent generation of TMA and TMAO, and enhanced atherosclerosis and thrombosis (1, 8-11).

During the conduct of untargeted metabolomics studies, the majority of spectral features detected in biological matrices arise from metabolites of unknown structural identity (12). Consequently, unambiguous identification of the "unknowns" of interest requires multiple studies and diverse approaches including performance of multiple distinct case: control studies using different mass spectrometry and chromatographic techniques (to narrow the focus of efforts to only those unknown analytes that appear to be reproducibly associated with the phenotype of interest), as well as synthesis of both structural isomers and isotopologues of candidate molecules (for direct comparisons with the unknown analyte). Moreover, once structural elucidation is achieved, because untargeted metabolomics studies are intrinsically only semi-quantitative, replication studies using more quantitatively accurate analytical approaches are important to validate candidate biomarker associations with disease risks. Further, to move beyond association, mechanistic studies are important to explore potential causal relationships, if any, between the candidate biomarker and disease. In this Example, we describe structural and subsequent validation and mechanistic studies identifying plasma levels of the unusual free amino acid N6-trimethyl-lysine (N6-trimethyl-lysine, TML) as a strong and independent prognostic biomarker of incident cardiovascular disease (CVD) risks in subjects independent of traditional cardiovascular risk factors. We also show TML is a relatively abundant post-translational modification of proteins in both animal and plants alike, is found in a wide array of animal and vegetable matter, and can serve as a nutrient precursor for gut microbiota-dependent generation of TMA and TMAO in vivo. Finally, this Example show that despite the clear structural and metabolic link between TML and gut microbial TMA/TMAO generation, the clinical association between circulating TML levels and incident CVD risks in subjects appears to be predominantly independent of TMAO, and that dietary TML does not appear to serve as a major source for microbial TMA and TMAO generation compared to choline and carnitine in both mice and humans.

Results

Discovery and Structural Identification of N6-Trimethyl-Lysine (TML) as a Plasma Metabolite Associated with CVD Risks We performed untargeted metabolomics studies in a non-overlapping cohort of sequential consenting subjects (N=1, 162) undergoing elective diagnostic cardiac evaluation using a high resolution MS-based approach, as described in Methods. Baseline characteristics of this cohort (Discovery Cohort 2) are shown in Table 2.

TABLE 2

| Baseline characteristics of the patients in the Discovery Cohort 2 | |
| --- | --- |
| Characteristics | Angiographic cohort (N = 1,162) |
| Age (years) | 64.0 ± 10.9 |
| Sex male (%) | 63.7 |
| Diabetes mellitus (%) | 22.1 |
| History of hypertension (%) | 72.1 |
| History of hyperlipidemia (%) | 85.8 |
| Former/current smoking (%) | 65.4 |
| History of CAD (%) | 75.6 |
| HDL cholesterol (mg/dL) | 34.3(28.5-41.2) |
| LDL cholesterol (mg/dL) | 96.0(80.0-116.0) |
| C-reactive protein (mg/L) | 2.3(1.0-5.4) |
| EGFR (ml/min/1.73 m²) | 85.0(71.4-94.8) |
| Baseline medications (%) | |
| Aspirin (%) | 76.8 |
| ACE inhibitors (%) | 49.9 |
| Beta blocker (%) | 65.3 |
| Statin (%) | 61.4 |

Continuous data are presented as mean ± standard deviation or median (interquartile range), categorical variables are presented as %.

Continuous data are presented as mean±standard deviation or median (interquartile range), categorical variables are presented as %.

An association between a plasma metabolite with high mass accuracy m/z 189.1598 and incident CVD risks was observed. As compared with subjects in the lowest quartile of analyte (m/z 189.1598) levels, patients in the highest quartile (Q4) demonstrated a significant increased risk of both incident (3 years) major adverse cardiac events (MACE myocardial infarction, stroke or death) (hazards ratio (95%

CI); 2.5(1.4-4.5); P=0.001), and incident (5-years) mortality risk (HR (95% CI); 2.7(1.6-4.6); P<0.001). Following adjustments for traditional CVD risk factors and C-reactive protein levels, elevated plasma levels of the analyte (m/z 189.1598) remained a significant predictor of risks of incident (3-year) MACE (adjusted HR (95% CI); 2.4(1.4-4.2); P=0.003) and mortality (5-year; adjusted HR (95% CI), 2.2(1.3-3.9); P=0.005) (FIG. 1B).

Figure 1:
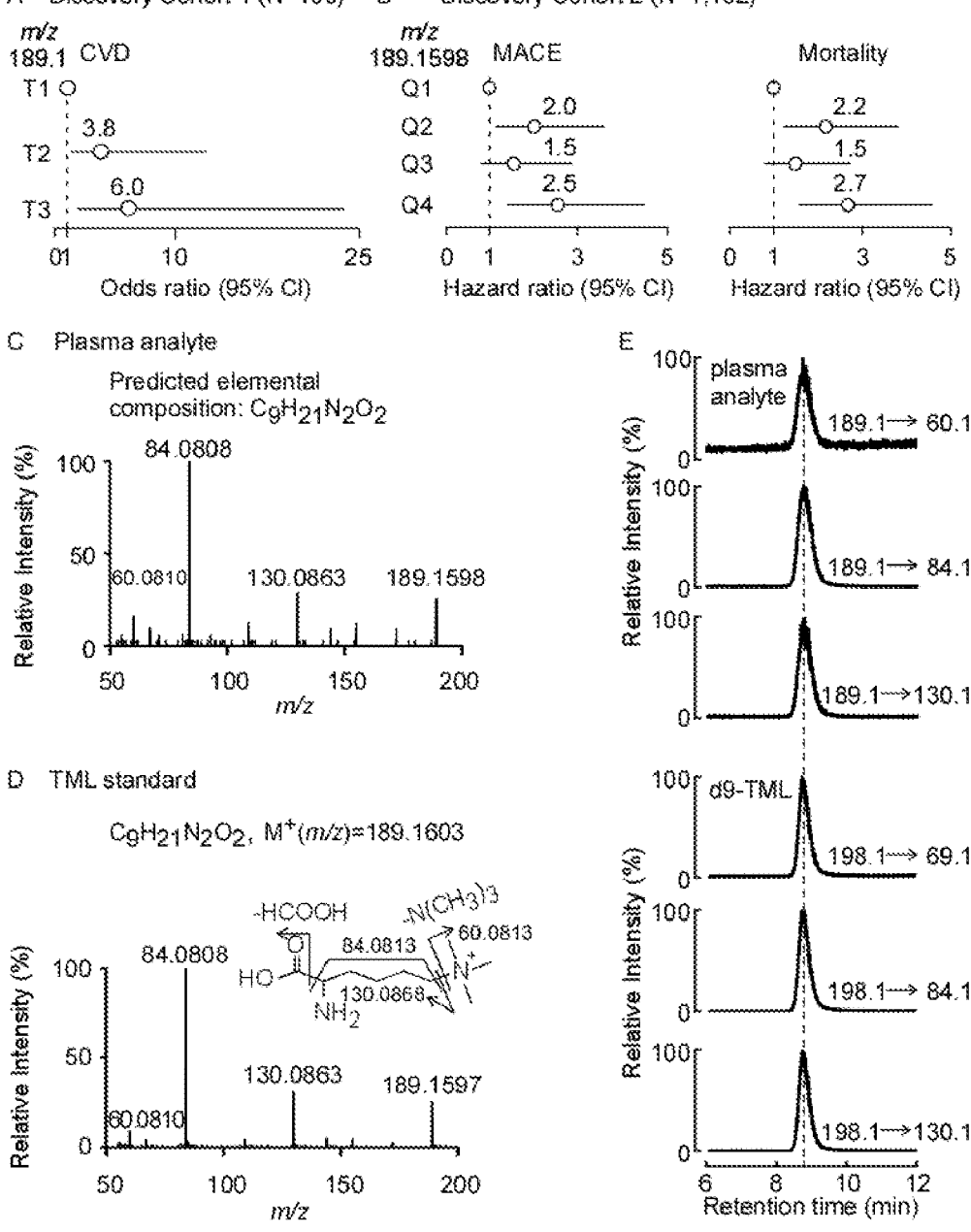
FIG. 1. Untargeted metabolomics studies discover candidate compound with m/z of 189.1598 is associated with CVD and is N6-trimethyl-lysine. (A) Forest plot indicating plasma metabolite of unknown structure with m/z of 189.1 is associated with risk for CVD according to relative peak area intensity ranked by tertiles among subjects (N=100) in the Discovery Cohort 1; (B) Forest plot indicating plasma metabolite of unknown structure with high resolution m/z of 189.1598 is associated with the risk for incident CVD and mortality risks according to relative peak intensity from untargeted mass spectrometry analyses of subjects (N=1162, Discovery Cohort 2). (MACE major adverse cardiac events, including myocardial infarction, stroke or death), the analyses were performed using R 3.4.1; (C) CID spectrum in positive ion mode of the metabolite m/z of 189.1598 in plasma; (D) CID spectra in positive mode of synthetic N6-trimethyl-lysine (TML) standard; (E) Demonstration of cochromatography of multiple unique parent→daughter ion transitions for plasma analyte m/z 189.1598 and synthetic d9-TML.

The collision-induced dissociation mass spectrum of the plasma metabolite with m/z 189.1598 revealed a molecular cation (M+) with a predicted elemental composition of $C_9H_{21}N_2O_2$ (FIG. 1C). This information, coupled with the observed high resolution fragmentation pattern (daughter ion m/z and intensities), strongly suggested the identity of the metabolite as N6-trimethyl-lysine (TML) (FIG. 1D, Table 3).

TABLE 3

| Comparison of experimental high resolution mass data from analyte m/z 189.1598 in plasma versus predicted m/z for parent and daughter ions of TML | | | | |
| --- | --- | --- | --- | --- |
| Analyte | Elemental composition | Theoretical m/z | Measured m/z | Delta (ppm) |
| TML | $C_9H_{21}N_2O_2$ | 189.1603 | 189.1598 | 2.64 |
| Daughter 1 | $C_3H_{10}N$ | 60.0813 | 60.0810 | 4.99 |
| Daughter 2 | $C_5H_{10}N$ | 84.0813 | 84.0808 | 5.95 |
| Daughter 3 | $C_6H_{12}NO_2$ | 130.0868 | 130.0863 | 3.84 |

Thus, in subsequent studies we compared analyte m/z 189.1598 with an authentic synthetic TML standard, and observed identical $MS^n$ and retention time characteristics using multiple different column matrices and chromatography conditions, as described under Methods. These data unambiguously confirmed the identity of analyte m/z 189.1598 as TML. We therefore synthesized d9(trimethyl) TML for use as internal standard (FIG. 8 and Table 8), and developed a stable isotope-dilution liquid chromatography with on-line tandem mass spectrometry (LC/MS/MS) based method for quantitative analyses of TML that was used in all subsequent investigations.

TABLE 8

| High resolution mass spectrometry analysis of synthetic d9-TML | | | | |
| --- | --- | --- | --- | --- |
| Analyte | Elemental Composition | Theoretical m/z | Measured m/z | Delta (ppm) |
| d9-TML | $C_9D_9H_{12}N_2O_2$ | 198.2168 | 198.2163 | 2.52 |
| Daughter 1 | $C_3D_9HN$ | 69.1378 | 69.1375 | 4.34 |
| Daughter 2 | $C_5H_{10}N$ | 84.0813 | 84.0804 | 10.70 |
| Daughter 3 | $C_6H_{12}NO_2$ | 130.0868 | 130.0860 | 6.15 |

The full scan CID mass spectrum of synthetic d9-TML was analyzed on an LC Triple TOF as described under Methods. The experimentally measured m/z of both parent and daughter ions are shown, along with the theoretical m/z and calculated difference (in ppm).

The method employs three different unique and characteristic parent→daughter ion transitions for monitoring TML and its heavy isotope labeled internal standard, and thus both quantitatively measured and further confirmed the identity of the analyte as TML (FIG. 1E; FIG. 9). It should also be noted that MS/MS spectra later deposited in Mass-Bank of North America from GNPS (13) and SPLASH (i.e., splash10-001i-5900000000-3e873bca7eaaf8953194) (14), identified as TML, also matched the unknown.

Clinical Validation Studies Confirm Systemic TML Levels Predict Incident MACE Risks Independent of CVD Risk Factors We next examined whether the association between plasma levels of TML and CVD risk was confirmed using the quantitative stable isotope dilution LC/MS/MS assay in an independent group of subjects (Validation Cohort). Samples from sequential stable consented patients (N=2, 140) undergoing elective diagnostic coronary angiography and for whom adjudicated long-term adverse outcomes data were available were examined. Baseline demographic, clinical and laboratory characteristics of the subjects in the Validation Cohort are shown in Table 4.

TABLE 4

Baseline characteristics of the patients in the Validation Cohort

|  | Angiographic cohort (N = 2,140) |
| --- | --- |
| Characteristics | |
| Age (years) | 62.9 ± 11.1 |
| Sex male (%) | 65.2 |
| Diabetes mellitus (%) | 40.8 |
| History of hypertension (%) | 72.7 |
| History of hyperlipidemia (%) | 85.2 |
| Former/current smoking (%) | 65.4 |
| History of CAD (%) | 74.5 |
| HDL cholesterol (mg/dL) | 33.9(28.2-40.6) |
| LDL cholesterol (mg/dL) | 96.0(79.0-116.0) |
| C-reactive protein (mg/L) | 2.6(1.1-6.3) |
| EGFR (ml/min/1.73 m$^2$) | 86.7(72.3-96.4) |
| TMAO (µM) | 3.7(2.5-6.2) |
| TML | 0.53(0.43-0.70) |
| Baseline medications (%) | |
| Aspirin (%) | 75.1 |
| ACE inhibitors (%) | 50.1 |
| Beta blocker (%) | 63.2 |
| Statin (%) | 60.7 |

Continuous data are presented as mean standard deviation or median (interquartile range), categorical variables are presented as %.

In general, the subjects were middle-aged (62.9±11.1 years), 65% male, had relatively preserved renal function, and in majority had either a high burden of CVD risk factors or CAD. Initial examination of the distribution of TML levels within the cohort (range 0.17-3.51 µM) showed a significantly higher TML level (P<0.001) among those who experienced a major adverse cardiovascular event (MACE=myocardial infarction, stroke or death) over the ensuing 3-year period following enrollment (FIG. 10). Similarly, higher TML levels were also observed among those who died over a 5-year follow-up period (P<0.001) (FIG. 10). Kaplan-Meier survival analyses revealed a dose-dependent relationship between higher TML levels and incident risk for MACE (3 years) and mortality (5 years) (log rank P<0.001 for each) (FIG. 2A, B). Moreover, compared to subjects in the lowest quartile (Q1) of TML levels, subjects in the highest quartile (Q4) demonstrated a significant increased risk of incident MACE (HR (95% CI); 2.9(2.0-4.0), P<0.001), or death (HR (95% CI); 3.8(2.7-5.5), P<0.001) (FIG. 2C). Elevated TML (Q4) levels remained an independent predictor of incident MACE (3 years) and mortality (5 years) risks even after adjustments for traditional cardiac risk factors and C-reactive protein levels (Adjusted model 1, FIG. 2C).

Examination of Potential Processes Impacting TML and CVD Risks.

Because the structure of TML contains a TMA moiety, we next sought to investigate whether there was a relationship between TML and TMAO levels, as well as whether the prognostic association between TML and CVD risks was dependent on TMAO. TMAO was therefore quantified in the same subjects using established stable isotope dilution LC/MS/MS methods in the entire cohort (15). Of note, Spearman correlation analyses revealed a highly significant association between plasma TML and TMAO levels (r=0.44, P<0.001, N=2,140) (FIG. 3A). Moreover, as previously observed in multiple cohorts (16-18), TMAO levels within the present cohort were associated with all monitored incident adverse CVD events including MACE (3 years) (HR (95% CI), 2.5(1.8-3.5); P<0.001) and mortality (5 years) risks (HR (95% CI), 4.0(2.7-5.8); P<0.001). When TMAO levels were included in the Cox regression models, elevated levels of both TMAO and TML remained significant predictors of incident (3-year) MACE and incident (5-year) mortality risks after multivariate adjustments including CAD status, traditional CVD risk factors, indices of renal function, and medications (FIG. 3B,C). The strength of the prognostic value of TML observed in the presence of TMAO is different from that observed with other TMA-containing compounds like choline, carnitine or betaine, since in past studies, the prognostic value of these TMA and TMAO precursors (choline, carnitine or betaine) are completely abolished following inclusion of TMAO into statistical models (8,19). The data observed (FIG. 2C, and FIG. 3B,C) thus suggests that some of the prognostic signal associated with TML and incident CVD event risks appears to be independent of TMAO levels.

To further examine and illustrate both the independence of TML and TMAO and their potential additive prognostic value, we stratified the entire cohort into low, intermediate and high groups of both TML (cutoffs 0.5, 0.8 µM) and TMAO (cutoffs 2.5, 6,0 µM) levels (FIG. 3D, Table 9).

TABLE 9

TMAO and TML provide independent additive clinical prognostic value for prediction of MACE risks

| | | TMAO (µM) | | |
| --- | --- | --- | --- | --- |
| | Range | <2.5 µM (low) | 2.5-5.99 µM (intermediate) | ≥6 µM (high) |
| TML (µM) | <0.5 µM (low) | 2.8%/yr 1.0 | 3.5%/yr 1.2(0.8-2.0) P = 0.40 | 5.2%/yr 1.9(1.1-3.4) P = 0.03 |
| | 0.5-0.79 µM (intermediate) | 4.7%/yr 1.7(1.01-2.9) P = 0.047 | 3.9%/yr 1.4(0.9-2.2) P = 0.18 | 7.7%/yr 2.9(1.8-4.5) P < 0.001 |
| | ≥0.8 µM (high) | 7.2%/yr 2.7(1.1-7.1) P = 0.04 | 6.4%/yr 2.4(1.4-4.2) P = 0.002 | 10.0%/yr 4.0(2.6-6.2) P < 0.001 |

The entire cohort (N=2,140) was stratified into low, intermediate and high level subgroups of TML and TMAO using the cutoffs indicated. Within each cell, the annual absolute incident event rate for MI, stroke or death (MACE) is shown at the top. The middle line depicts the calculated Hazard Ratio (95% Confidence Interval) for risk of incident MACE relative to subjects with low levels of both TML and TMAO as reference group. And the bottom line provides the p value for comparison relative to subjects with low levels of both TML and TMAO as reference group.

Notably, compared to subjects with low levels of both TML and TMAO (reference group), who experienced an absolute annual MACE rate of 2.8%/yr, subjects with both high TML and TMAO levels experienced a remarkable 10%/yr annual event rate, which represents a 4.0-fold increased risk of incident MACE (HR, 4.0, 95% CI, 2.6-6.2; P<0.001) (FIG. 3D, Table 9). Further, the independence of TML and TMAO clinical prognostic value is further illustrated by noting that even amongst subjects with low TMAO levels, increasing levels of TML are associated with significant increase in MACE risk (2.7 fold risk when TML is high;

sought to test whether we could identify genetic determinants of plasma TML levels using an unbiased genome-wide association study (GWAS) approach. Of the 2,140 subjects with TML levels, 1,297 also had data for 9,012,028 imputed autosomal single-nucleotide polymorphisms (SNPs). As shown by the Manhattan plot (FIG. 4), no locus exceeded the genome-wide significant P-value of $5.0 \times 10^{-8}$, but several SNPs (mostly with MAFs $\leq 5\%$) on chromosomes 1, 3, 5, 6, and 8 exhibited suggestive evidence of association (P<5.0× $10^{-7}$) (Table 5).

TABLE 5

Lead SNPs at Loci Identified for Plasma TML Levels in the GeneBank Cohort

| SNP | Chromosome | [a]Position | [b]Alleles | [c]EAF | [d]Beta ± SE | [d]P-value |
|---|---|---|---|---|---|---|
| rs34568450 | 1q44 | 244,489,956 | G/A | 0.10 | 0.114 ± 0.023 | $4.8 \times 10^{-7}$ |
| rs75233056 | 3p24.1 | 28,192,633 | A/T | 0.06 | 0.158 ± 0.030 | $1.1 \times 10^{-7}$ |
| rs11133993 | 5p15.33 | 3,568,737 | A/G | 0.28 | 0.077 ± 0.015 | $4.7 \times 10^{-7}$ |
| rs78078192 | 6p24.1 | 13,320,526 | G/A | 0.02 | 0.252 ± 0.048 | $2.2 \times 10^{-7}$ |
| rs150604736 | 6q23.3 | 137,385,027 | A/G | 0.01 | 0.287 ± 0.056 | $3.0 \times 10^{-7}$ |
| rs562044044 | 8p21.2 | 26,462,015 | G/T | 0.01 | 0.301 ± 0.057 | $1.3 \times 10^{-7}$ |

[a]Base pair positions are given according to NCBI build 37 (hg19) of the reference human genome sequence,
[b]SNP alleles are shown as effect allele/other allele,
[c]EAF indicates effect allele frequency,
[d]Betas ± SE refer to the effect allele, and P-values were obtained by linear regression using natural log transformed values, assuming an additive genetic model, and with adjustment for age and sex.

P=0.04); and similarly, among subjects with a low TML level, increasing TMAO levels dose dependently is associated with increased MACE risk (e.g. 1.9 fold risk when TMAO is concurrently high; P=0.03) (FIG. 3D, Table 9). Thus, unlike other TMAO nutrient precursors like choline, carnitine or betaine (8,19), TML provides independent and additive prognostic value in combination with TMAO for prediction of incident MACE risks.

Given the above results, we next proceeded to explore the potential origins of the association between TML and incident CVD risks. TML can be generated in both free and protein bound form via lysine methylation. Methylation of free lysine to form TML is an initial step in the biosynthetic pathway for carnitine (i.e. lysine→TML→γ-butyrobetaine→carnitine) (20, 21). Within the same subjects examined for TML levels (N=2,140) we therefore also performed stable isotope dilution LC/MS/MS analyses of each of the metabolites in the carnitine biosynthetic pathway using established methods (1, 8, 9, 15). Of note, each metabolite demonstrated a significant correlation with plasma TML levels (Spearman correlation coefficients of TML with lysine (r=0.16, P<0.001); γ-butyrobetaine (r=0.43, P<0.001); and carnitine (r=0.28, P<0.001)). Protein-bound TML is also generated as a common post-translational modification of protein lysine residues, particularly histones during chromatin remodeling and transcriptional regulation (22, 23); however, the presence and distribution of protein-bound TML in secreted proteins within plasma has been largely unexplored. We therefore examined the relationship between plasma free TML levels versus protein-bound TML in plasma proteins recovered (Methods) from a random set of subjects (N=25). Remarkably, the content of total protein-bound TML in plasma proteins was highly correlated with free TML amongst all subjects (Spearman correlation r=0.82, P<0.001), as well as among both healthy controls (r=0.69, P<0.01; N=16), and subjects with CVD (r=0.95, P<0.001; N=9) (FIG. 3E).

The factors that contribute to variations in plasma TML levels amongst subjects are largely unexplored. We therefore We also specifically looked at 400 kb regions surrounding the genes encoding 27 known lysine methyltransferases (24), but none of these candidate loci yielded evidence of association with TML levels either. We next used the results from the CARDIoGRAM Consortium (25) to determine whether any of the six suggestively associated regions/loci for plasma TML levels were associated with risk of CVD. Data were available for five of these loci, but none of these were associated with risk of CVD in CARDIoGRAM (Table 6).

TABLE 6

Association of suggestive loci for plasma TML levels with risk of CVD

| SNP | EA (Frequency) | OR (95% CI) | P-value |
|---|---|---|---|
| rs34568450 | A (0.85) | 0.98 (0.95-1.01) | 0.13 |
| rs75233056 | T (0.93) | 0.98 (0.94-1.03) | 0.42 |
| rs11133993 | G (0.73) | 1.01 (0.99-1.03) | 0.34 |
| rs78078192 | A (0.97) | 1.00 (0.94-1.05) | 0.88 |
| rs150604736 | G (0.98) | 0.96 (0.88-1.05) | 0.38 |

Odds Ratio (OR) and 95% Confidence Intervals (CI) refer to the effect allele and were obtained from the results of the CARDIoGRAM Consortium Since both plant and animal cells alike use histone protein methylation to regulate gene expression, we wondered whether TML (free plus protein bound) could be a potentially unrecognized yet abundant nutrient precursor for TMAO generation from plant and animal derived foods. To examine the relative levels and distribution of TML versus other major TMAO nutrient precursors in common foods, we quantified total (free+esterified or protein-bound) levels of TML, choline and carnitine in a variety of animal and plant derived foods (Table 7).

US 12,576,055 B2

35

TABLE 7

Total N6-trimethyl-lysine, carnitine and
choline contents in some common foods

| Foods | N6-trimethyl-lysine (mg/100 g) | Carnitine (mg/100 g) | Choline (mg/100 g) |
|---|---|---|---|
| Vegetable | | | |
| White onion | 0.40 | 0.03 | 6.04 |
| Cucumber | 0.74 | 0.02 | 6.42 |
| Tomato | 0.81 | 0.14 | 7.99 |
| Carrot | 0.65 | 0.07 | 11.96 |
| Dairy and Egg | | | |
| Cheese | 4.31 | 0.63 | 16.44 |
| Whole milk | 0.72 | 0.85 | 8.0 |
| Butter | 0.34 | 0.35 | 12.49 |
| Whole Egg | 13.68 | 0.89 | 253.0 |
| Sea food | | | |
| Tuna | 5.56 | 1.28 | 19.29 |
| Salmon | 4.84 | 0.60 | 65.81 |
| Shrimp | 12.25 | 1.25 | 27.35 |
| Meat | | | |
| Chicken | 0.97 | 1.20 | 22.34 |
| Turkey | 5.82 | 4.66 | 49.60 |
| Pork | 4.31 | 2.27 | 39.95 |
| Veal | 6.05 | 18.06 | 38.61 |
| Lamb | 2.36 | 21.98 | 40.29 |
| Deer | 4.10 | 22.16 | 33.63 |
| Goat | 8.63 | 20.59 | 48.08 |
| Beef | 6.12 | 38.42 | 60.97 |
| Beef liver | 3.66 | 0.52 | 271.6 |

The data shown is for total (free plus esterified or protein-bound) TML, choline or carnitine contents in some common foods.

The data shown is for total (free plus esterified or protein-bound) TML, choline or carnitine contents in some common foods.

Surprisingly, TML was found in virtually all food sources, though in general, at a greater level in animal versus plant derived products. Thus, when compared to total choline or total carnitine content in foods, TML was present at surprisingly abundant levels (Table 7).

Dietary TML can Generate TMA and TMAO Via Gut Microbiota

Given the presence of TML in so many food sources, we next examined whether dietary TML could serve as a substrate for microbiota dependent generation of TMA and TMAO. We initially performed oral (gastric gavage) challenges in mice using either synthetic d9(trimethyl)-TML (see Additional Methods for synthesis and characterization) or d9(trimethyl)-choline, and monitored serial plasma samples over time for quantification of isotope labeled parent compound and d9-TMA and d9-TMAO levels. Following oral d9-TML gavage of conventionally reared C57BL/6J mice, plasma levels of both d9-TMA and d9-TMAO rose only minimally following a lag phase, despite a rapid (within 1 hour) increased in d9-TML level following ingestion (FIG. 5A,B,C). By comparison, identically challenged C57BL/6J mice with the same (molar) amount of oral d9-choline demonstrated markedly (30-50 fold) higher peak levels of d9-TMA and d9-TMAO, and substantially lower plasma level of isotope labeled precursor (d9-choline) (FIG. 5D,E,F). These results directly demonstrate that oral TML can serve as a precursor for TMA and TMAO generation. Of note, however, compared with comparable oral challenge of choline, TML was a much poorer precursor for TMA and TMAO formation in vivo.

To determine whether gut microbes are involved in dietary TML-dependent generation of TMAO, parallel studies were performed in mice before versus following 3-weeks exposure to a cocktail of oral poorly absorbed broad-spectrum antibiotics previously shown to markedly suppress gut microbiota (1, 26). Notably, despite initial generation of TMAO before antibiotics (FIG. 5G), no detectable plasma d9-TMAO was observed following d9-TML oral gavage in mice treated with the oral antibiotics (FIG. 5G). Further, the pretreatment with oral antibiotics had no impact on plasma d9-TML levels following oral gavage (P=0.87). Collectively, these results are consistent with gut microbial involvement in TMA and TMAO generation from dietary TML, albeit at a level substantially lower than observed with dietary choline.

Characterization of Mouse and Human Gut Bacteria—Dependent Generation of TMA from TML Initial studies examining cecal contents recovered from conventionally reared mice revealed d9-TMA generation from d9-TML under anaerobic (but not aerobic) culture conditions, as described under Methods. We therefore examined the anatomical distribution of gut microbiota capable of producing d9-TMA from d9-TML in intestine contents recovered from segments harvested from conventionally raised mice and cultured in an anaerobic chamber. To permit direct comparisons, we also performed side-by-side anaerobic cultures using comparable amounts of two alternative TMA-producing nutrient precursors, d9-carnitine and d9-choline (FIG. 6A). Interestingly, microbes recovered from both cecal and colonic segments generated d9-TMA from d9-TML under anaerobic culture, and significantly lower but detectable levels of d9-TMA were also formed from d9-TML incubated with small bowel microbes. By comparison, only cecal and colonic microbiota converted d9-carnitine or d9-choline into d9-TMA. Notably, the synthetic capacity of cecal microbiota to generate d9-TMA from d9-carnitine was 10-fold higher than that observed with d9-TML, and 1000-fold higher from a comparable exposure to d9-choline. These data thus reveal a nutrient TMA-generating potential from murine gut commensals of TML<carnitine <<choline (FIG. 6A).

We next sought to examine known culturable human commensals to identify specific microbial species capable of using TML as substrate to generate TMA. We began with studies employing a panel of 68 culturable human commensals, representing a large fraction of the diversity observed in the human gut, including the seven most abundant bacterial phyla and 28 different genera. This library was previously used to identify species capable of converting choline into TMA (i.e. through choline TMA lyase activity) (27). Eighteen individual members of the human commensal library were initially screened under anaerobic conditions as previously described for detecting choline TMA lyase activity using d9-choline as substrate, but this time adding d9-TML to media, as described under Methods. Despite the ability of several strains to convert d9-choline→d9-TMA under these conditions, none of these species significantly promoted conversion of d9-TML→d9-TMA. We next examined whether a pool containing all 68 species (grown individually and mixed in similar proportions prior to the assay) could promote the conversion of d9-TML→d9-TMA, speculating that perhaps the observed activity in cultured cecal/colonic contents, and in vivo (mouse isotope tracer studies), might occur via sequential metabolic transformations promoted by more than one microbe. Unfortunately, however, virtually no detectable d9-TML→d9-TMA transformation was observed with pooled microbes in prolonged (4 days) incubation (assay limit of detection, ~1 nM). These results suggest that conversion of TML to TMA is a relatively rare trait, possibly restricted to a specific taxonomic group not represented in our screen, or possibly inactive under the screening conditions.

Given that d9-TML is clearly converted into d9-TMA in a gut microbiota dependent fashion in vivo in mice (FIG. 5), and in anaerobic cultures of either mouse cecal or colonic contents (FIG. 6A), we next decided to examine human polymicrobial fecal anaerobic cultures for their capacity to convert d9-TML→d9-TMA. Human feces from both healthy volunteer omnivores (N=10 or more) and vegans (N=8) were examined for d9-TMA generation from equivalent amounts of d9-TML versus the alternative TMA precursor nutrients, d9-camitine and d9-choline, under anaerobic culture conditions. Notably, feces from omnivores and vegans alike promoted the transformation of d9-TML→d9-TMA, with omnivores having significantly greater activity than vegans (P<0.04; FIG. 6B). However, the overall level of TMA generation from TML was relatively low, with d9-camitine→d9-TMA transformation showing a comparable degree of d9-TMA formed in vegans. Remarkably, over a 100-fold greater production of d9-TMA was produced from d9-carnitine incubated with polymicrobial fecal cultures from omnivores (FIG. 6B). Even more notable was the observation that d9-choline→d9-TMA conversion within anaerobic cultures from human feces recovered from vegan and omnivore alike were both approximately 3 orders of magnitude greater than the levels of d9-TMA produced from d9-TML (FIG. 6B). These studies thus revealed a nutrient TMA-generating potential from human fecal commensals of TML<carnitine<<choline, similar to results observed with mice cecal and colonic microbiota.

In a series of studies aimed at examining gut microbial participants in TMA/TMAO generation, we examined whether recombinant forms of known microbial enzymes capable of generating TMA with alternative substrates could instead use TML as substrate to produce TMA. We thus examined transformed *E. coli* expressing either the genes cutC/D, yeaX/W, or cntA/B, microbial TMA generating enzyme systems previously reported for their capacity to use choline, or camitine related substrates (28-30). With *E. coli* transformed individually with each recombinant enzyme system, and despite observing enzymatic activity (TMA generation) with previously reported substrates for generating TMA from the given microbial TMA lyases, none of the known recombinant microbial TMA generating enzyme systems examined supported d9-TML conversion into d9-TMA (FIG. 6C).

Impact of Chronic Dietary TML Versus Choline Supplementation on Systemic TMAO Levels and In Vivo Thrombosis Potential In previous studies it was shown that chronic provision of a dietary nutrient can lead to enhanced gut microbial community capacity to form TMA and raise systemic TMAO levels (8). Since TML→TMA conversion in human fecal polymicrobial cultures derived from omnivores was significantly greater than that observed from vegans (FIG. 6B), we hypothesized chronic dietary exposure may enhance gut microbiota dependent conversion of TML→TMA. We therefore sought to investigate the impact of chronic dietary TML supplementation on plasma TMAO levels and in vivo thrombosis potential in mice. Since a large amount of TML is not readily commercially available, before proceeding, we synthesized and chemically characterized sufficient quantities of TML for the proposed in vivo studies (FIG. 11, Table 10).

TABLE 10

| High resolution mass spectrometry analysis of comparison of measured synthetic TML | | | | |
|---|---|---|---|---|
| Analyte | Elemental composition | Theoretical m/z | Measured m/z | Delta (ppm) |
| TML | $C_9H_{21}N_2O_2$ | 189.1603 | 189.1595 | 4.23 |
| Daughter 1 | $C_3H_{10}N$ | 60.0813 | 60.0805 | 13.30 |
| Daughter 2 | $C_5H_{10}N$ | 84.0813 | 84.0802 | 13.08 |
| Daughter 3 | $C_6H_{12}NO_2$ | 130.0868 | 130.0858 | 7.69 |

The full scan CID mass spectrum of synthetic TML was analyzed on an LC Triple TOF as described under Methods. The experimentally measured m/z of both parent and daughter ions are shown, along with the theoretical m/z and calculated difference (in ppm).

In addition, for direct comparison, parallel mouse studies were performed using chronic supplementary (1%) dietary choline. Provision of supplemental dietary TML (1%) to mice for up to 11 days resulted in a highly significant near 100-fold increase in plasma TML levels (P<0.0001) but no significant increase in systemic TMAO levels (FIG. 7A, B). By comparison, provision of the comparable amount of supplemental dietary choline (1%) significantly (~20-fold) raised plasma TMAO levels (P<0.0001, FIG. 7C). We further tested if elevated plasma TML in mice fostered enhanced thrombosis potential in vivo using a FeCl3 induced carotid artery injury model. The impact of a comparable amount of choline supplementation on in vivo thrombosis potential was similarly examined for comparisons. As shown in FIG. 7D, chronic dietary TML failed to significantly change thrombus formation rate, or time to cessation of blood flow, in the carotid artery injury in vivo thrombosis model (FIG. 7D). In contrast, however, as previously observed with choline supplementation (11), significant TMAO elevations were accompanied by enhanced in vivo thrombosis potential, as monitored via reduction in time to cessation of blood flow of the carotid artery following FeCl3 induced injury (FIG. 7D).

In this Example, we utilized untargeted metabolomics to discover systemic levels of the unusual free amino acid, TML, are strikingly associated with incidence of CVD risks independent of multiple cardiometabolic risk factors, prevalent CVD and medication use. Our studies also reveal that TML, a TMA-containing compound, is surprisingly abundant in both plant and animal foods alike, and that gut microbiota have evolved enzymatic machinery to metabolize TML. None-the-less, our studies show that in gut commensals from both mice and humans, the utilization of TML as nutrient precursor for TMA and TMAO formation is a relatively modest microbial activity compared to microbiota-dependent conversion of choline, and to lesser extent, carnitine (especially in omnivores). Further, gut microbial transformation of TML into TMA occurs via enzyme(s) distinct from known microbial choline or carnitine TMA lyases, such as cutC/D, cntA/B or yeaW/X.

Despite the observed association between TML and incident CVD risks, the underlying mechanism(s) accounting for the strong association remain unclear. One obvious mechanism that was extensively explored was the potential capacity of TML to form TMA and the atherogenic and pro-thrombotic metabolite TMAO. However, multiple lines of evidence suggest that mechanisms alternative to TMAO account for the observed association between TML and incident CVD risks. First, in clinical studies, adjustment for TMAO in COX models failed to significantly attenuate the clinical prognostic value of TML and incident CVD risks. This behavior contrasts with that observed with other TMA nutrient precursors like choline, betaine or carnitine, which lose their clinical prognostic value for incident CVD risks when TMAO levels are included in multilogistic regression models (8, 19). Further, despite observing gut microbiota dependent generation of TMA and TMAO from TML, plasma levels of TMAO were not affected by dietary TML. Thus, in contrast to choline supplementation, which raises TMAO levels and increases in vivo thrombosis potential (11), chronic TML supplementation both failed to raise TMAO levels and did not enhance in vivo thrombosis potential as monitored using a carotid artery injury model. Lastly, to try and identify factors which may be linked to systemic TML levels and CVD risk, we performed a GWAS study in ~1,300 subjects. While several suggestive loci were identified, none reached genome-wide significance or yielded evidence of association with risk of CVD.

An intriguing finding in the present study is the remarkably tight correlation observed between protein-bound TML and free TML levels. These results raise the prospects that free TML levels may reflect the level of protein-bound TML in the vascular compartment. It is intriguing to note that lysine methylation plays a critical role in the histone code and the overall regulation of chromatin remodeling and transcriptional gene control. While lysine methylation was originally proposed to be an irreversible post-translational modification on proteins, it has recently been recognized that protein lysine residue methylation (at least for histones) can be reversible, with multiple demethylases discovered (31-33). With discovery of protein-bound TML presence in plasma and its remarkably high correlation with free TML, the role of protein lysine methylation in both the secreted proteome and proteins within the vascular wall and other organs is of interest. Moreover, whether the protein bound TML detected in the vascular compartment is a reversible post translational modification, like in histones, is similarly of interest.

It is remarkable that the present studies identify another TMA-containing metabolite, TML, with links to both TMA and TMAO generation and significant clinical prognostic value for incident adverse cardiovascular event risks. Of note, in contrast to choline or carnitine, chronic dietary TML fails to significantly change plasma TMAO levels, and in this respect, TML behaves somewhat like betaine, which similarly was identified through untargeted metabolomics as having plasma levels associated with incident MACE risks (1), and which can be a TMA nutrient precursor, albeit also at a rate about 100-fold less than choline (19). The present studies reaffirm the promise of untargeted metabolomics as a platform for discovery of candidate metabolites and pathways with links to disease processes. They substantially expand our understanding of TML and its association with CVD risks.

Materials and Methods

Clinical Study Population

Plasma samples, feces and associated clinical data were collected as part of two studies at a tertiary care center. Metabolomics studies were performed on GeneBank samples, a large (N>10,000) well-characterized and longitudinal tissue repository with associated clinical database. It was comprised of sequential participants enrolled in the study GeneBank, which consists of sequential stable subjects without evidence of acute coronary syndrome (cardiac troponin I<0.03 ng/mL) who underwent elective diagnostic coronary angiography (cardiac catheterization or coronary computed tomography) for evaluation of CAD (1, 16, 34). All subjects had extensive clinical and longitudinal outcomes data monitored, including adjudicated outcomes over the ensuing 3 to 5 years for all participants after enrollment. Major adverse cardiovascular event (MACE) was defined as death, nonfatal MI, or nonfatal cerebrovascular accident (stroke) following enrollment. Initial discovery metabolomics analyses began with an unbiased search for plasma analytes linked to CVD risk using a case: control design (50 cases and 50 controls, Discovery Cohort 1). Cases were randomly selected from GeneBank subjects who experienced a myocardial infarction, stroke or death over the ensuing 3-year period following enrollment (1). For controls, an age- and gender-matched group was randomly selected from GeneBank subjects that did not experience a CVD event. An independent non-overlapping cohort (N=1, 162, Discovery Cohort 2) for untargeted metabolomics was also derived from sequential consenting subjects enrolled in GeneBank. A third large independent non-overlapping Validation Cohort (N=2,140) was also from sequential consenting subjects enrolled in GeneBank. Fasting blood glucose, high-sensitivity C-reactive protein, and lipid profiles were measured on the Roche Cobas platform (Roche Diagnostics, Pleasanton, CA, USA).

In additional studies, healthy volunteers (N=15 omnivores and N=8 vegetarians or vegans) were consented and subjected to extensive dietary questioning and stool collection as part of a study examining gut microbiota dependent metabolism of dietary carnitine and cardiovascular disease (8). Only feces at baseline were used. Male and female volunteers were at least 18 years of age. Volunteers participating were excluded if they were pregnant, had chronic illness (including a known history of heart failure, renal failure, pulmonary disease, gastrointestinal disorders or hematologic diseases).

Initial Metabolomics Analyses

In general, the initial untargeted metabolomics approach used was similar to that described previously (1, 8). Plasma proteins were precipitated with four volumes of ice-cold methanol and small-molecule analytes within supernatants were analyzed after injection onto a phenyl column (4.6×250 mm, 5 μm Rexchrom Phenyl; Regis) at a flow rate of 0.8 ml/min using a Cohesive HPLC interfaced with a PE Sciex API 365 triple quadrupole mass spectrometer (Applied Biosystems) with Ionics HSID1, EP101, XT1 redesigned source and collision cell as upgrades in positive MS1 mode. LC gradient (LC1) starting from 10 mM ammonium formate over 0.5 min, then to 5 mM ammonium formate, 25% methanol and 0.1% formic acid over 3 min, held for 8 min, followed by 100% methanol and water washing for 3 min at a flow rate of 0.8 ml/min was used to resolve analytes. Spectra were continuously acquired after the initial 4 min. Peaks within reconstructed ion chromatograms at 1 AMU increments were integrated and both retention times and m/z of analytes were used for statistical analyses.

To chemically define the structures of the plasma analyte selected for further investigation (that is, candidate compound with m/z 189.1 in positive MS1 mode). N6-trimethyllysine in plasma was identified by HPLC-high resolution mass spectrometer with same retention time, high resolution mass and fragmented ions as standard. Plasma supernatant after methanol precipitation of protein was analyzed by injection onto a silica column (2.0×150 mm, 5 μm Luna silica; Cat#00G-4274-B0, Phenomenex, Torrance, Ca) using a 2 LC-20AD Shimadzu pump system, SIL-HTC autosampler interfaced with a TripleTOF™ 5600 mass spectrometer (AB SCIEX, Framingham, MA). Separation was performed employing a gradient starting at 100% A (10 mM ammonium acetate aqueous solution) for 2 min, then increasing linearly to 20% B (acetonitrile:methanol:acetic acid, 50:50:0.1, v/v/v) over 8 min followed by 100% B washing for 5 minutes and 100% A balancing for 5 minutes. The parameters for the ion monitoring were as follows: Spray voltage, 5.5 kV; Curtain gas, 20; GS1, 20; GS2, 15; DP, 30; CE, 30 volts, CES, 15 volts. Nitrogen (99.95% purity) was used as the only gas.

To confirm the identity of plasma analyte 189.1 as TML, the plasma analyte and synthetic d9-TML standard were examined on multiple different column matrices and chromatography conditions:

System 1: column (2.0×150 mm, 5 μm Luna silica; Cat#00G-4274-B0, Phenomenex, Torrance, CA), separated on discontinuous gradient comprised of mobile phase A (0.1% propionic acid in water) versus mobile phase B (0.1% acetic acid in methanol) starting at 100% A for 2 min, then increasing linearly to 15% B over 8 minutes followed by 100% B washing for 5 minutes and balancing for 5 minutes; the flow rate, 0.2 ml/min;

System 2: column (2.0×50 mm, 1.9 μm Titan silica; Cat#581530-U, Supelco, Bellefonte, PA), separated on discontinuous gradient comprised of mobile phase A (10 mM ammonium formate and 0.1% formic acid in water) versus mobile phase B (10 mM ammonium formate and 0.1% formic acid in acetonitrile) starting at 100% B linearly decreasing to 100% A over 4 minutes followed by washing with 100% A for 0.5 minute and balancing with 100% B for 0.5 minutes; the flow rate, 0.4 ml/min; System 3: column (2.0×150 mm, 3 μm Scherzo SM-C18; Cat#SM025, Imtakt, Portland, OR) separated on discontinuous gradient comprised of mobile phase A (0.1% formic acid in water) versus mobile phase B (0.1% formic acid in methanol)) starting at 100% A for 2 min, then increasing linearly to 15% B over 7 minutes followed by 100% B washing for 3 minutes and balancing for 3 minutes; the flow rate, 0.3 ml/min.

Untargeted Analysis of Plasma Samples Using HILIC-MS

Untargeted analysis of plasma samples was similar used to that described previously (35, 36). In brief, extraction of plasma metabolites was carried out using an acetonitrile/isopropanol/water (3:3:2, v/v/v) mixture. Aliquots were evaporated, resuspended using an acetonitrile/water (4:1, v/v) mixture, vortexed, centrifuged, and upper layer transferred to a glass vial with a microinsert. HILIC analysis was performed on a system including an Agilent 1290 Infinity LC system (Agilent Technologies) with a pump (G4220A), a column oven (G1316C), an autosampler (G4226A), and a Triple TOF 5600+(SCIEX, Framingham, MA, USA). Extracts were separated on an Acquity UPLC BEH Amide column (150×2.1 mm; 1.7 μm, Waters, Milford, MA, USA) coupled to an Acquity UPLC BEH Amide VanGuard precolumn (5×2.1 mm; 1.7 μm) (Waters). The column was maintained at 45° C. at a flow rate of 0.4 mL/min. The mobile phases consisted of (A) water with ammonium formate (10 mM) and formic acid (0.125%) and (B) 95:5 (v/v) acetonitrile-water with ammonium formate (10 mM) and formic acid (0.125%). The separation was conducted under the following gradient: 0 min 100% B; 0-2 min 100% B; 2-7.7 min 70% B; 7.7-9.5 min 40% B; 9.5-10.25 min 30% B; 10.25-12.75 min 100% B; 12.75-17.75 min 100% B. A sample volume of 1 μL was used for the injection. Sample temperature was maintained at 4° C. The QTOFMS instrument was operated in electrospray ionization in positive mode with the following parameters: curtain gas, 35; ion source gas 1, 50 psi; ion source gas 2, 50 psi; temperature, 300° C.; ion spray voltage floating, 4.5 kV; declustering potential, 100 V; acquisition speed, 2 spectra/s. For data processing MZmine 2 (37) and MultiQuant (SCIEX) software programs were used.

Quantification of TML, TMAO, TMA, Lysine, Butyrobetaine and Carnitine

Stable isotope dilution LC/MS/MS was used for quantification of TML, TMAO, TMA, lysine, γ-butyrobetaine and carnitine similar to that described previously (1, 8, 9, 15). For TML standard curves, varying levels of TML were spiked into 20 μl control plasma followed by precipitation with 80 μl methanol containing 0.8 nmol d9-TML. Supernatant was loaded for LC/MS/MS analysis. Analyses were performed using electrospray ionization in positive-ion mode with multiple reaction monitoring of parent and characteristic daughter ions and retention times specific for components monitored. The transitions monitored for TML were mass-to-charge ratio (m/z): m/z 189.1→84.1, 189.1→60.1, and 189.1→130.1. The internal standards (e.g., d9-trimethyl-TML, d9-trimethyl-TMAO) were added to plasma before protein precipitation. Various concentrations of analytes and a fixed amount of internal standards were spiked into control plasma to prepare the calibration curves for quantification of plasma analytes. Their concentrations in human and mouse plasma samples were determined by high-performance liquid chromatography with a Shimadzu 8050 triple quadrupole mass spectrometer interfaced to a Shimadzu Nexera Ultra High Performance Liquid Chromatograph (UHPLC) system.

Genotyping and Imputation

Genome-wide genotyping was carried out on 3031 GeneBank subjects of European ancestry using the Affymetrix Genome-Wide Human Array 6.0 SNP chip. After conversion of genomic coordinates to GRCh37/hg19, exclusion of SNPs with duplicates, call rates <97%, minor allele frequencies (MAFs)<1%, and without chromosome and base pair position, and exclusion of 44 subjects with genotype call rates <90%, 642,766 were available for imputation in 2972 participants. Imputation was carried out on the forward (+) strand using the University of Michigan Imputation Server (imputationserver.sph.umich.edu) and data from the 1000 Genomes Project (Phase 3, Version 5). Application of the same quality control filters described above to the 46,180, 700 imputed SNPs, with the addition of excluding SNPs with Hardy-Weinberg equilibrium P-values <0.0001 and imputation Rsq scores <0.3, resulted in 9,012,028 autosomal SNPs that were available for analysis in 1297 GeneBank subjects for whom plasma TML levels were also available.

Total TML, Carnitine and Choline Quantification in Food

Plant and animal derived products were purchased in various local supermarkets. A portion of samples was accurately weighed into a 2.0 ml polypropylene Eppendorf tube in a total of 1.5 ml water (if homogenization was needed). Tissues were homogenized using a TissueLyser II (Qiagen, Germantown, MD, USA) with a 5 mm stainless steel ball and with the adapters in cold operated at 30 Hz for 2 min, 5 to 10 times (until samples appeared homogenous). After thorough mixing, a 20 μl aliquot of homogenate was transferred to a baked glass test tube with mininert valve screw cap, TML, carnitine and choline isotope labeled internal standards were added, and 0.5 ml 6 N HCl was added. Samples were hydrolysis by incubation under argon atmosphere at 110° C. for 20 hours. Samples and standards were cooled down, 2 ml water added to the hydrolysate, and then the mixture was processed using solid-phase extraction (Discovery DSC-SCX 3 ml Tube, 500 mg, Supelco, Bellefonte, PA, USA). Activation and conditioning of the solid phase column before sample addition consisted of 2×2.5 ml of methanol followed by 2×2.5 ml aliquots of 0.2 N formic acid. The sample was then loaded and subsequently washed with 2×2.5 ml formic acid. Analytes were eluted using 70% methanol, 5% ammonium hydroxide, 0.1 M ammonium formate. The eluent was evaporated using a heated nitrogen evaporation system, and continued drying of recovered material using speed-vacuum, and then the sample was reconstituted to 100 µl with 50% aqueous methanol for stable-isotope dilution LC/MS/MS analysis. Total plasma TML content of samples followed a similar overall solid protocol except for use of d9(trimethyl)-TML as internal standard.

Metabolic Challenges in Mice

Whole blood (50 µl) was collected via the saphenous vein from C57BL/6J (Jackson #0664) female mice prior to gavage for the measurement of baseline analyte levels. Mice were administered an oral dose of stable isotope-labelled TML or choline. The gastric gavage consisted of 150 µl of either 150 mM synthetic d9-TML or 150 mM choline-N,N, N-trimethyl-d9 (d9-choline, Cambridge Isotope Lab), followed by post-gavage blood collection at the indicated times. Where indicated, gut microbiota were suppressed in mice by placement of a cocktail of poorly absorbed antibiotics in drinking water for 3 weeks prior to the d9-TML challenge, as previously described (1, 19). Quantification of the abundance of native and isotope-labeled forms of TML, TMA and TMAO in mouse plasma was performed using stable-isotope-dilution LC-MS/MS using established methods for TMA and TML (19), and using the parent daughter ion transitions for TML and its internal standard as described above. In additional studies, the role of gut microbiota in TMAO formation from dietary TML was determined in C57BL/6J mice by performance of oral (gavage) d9-TML challenge. Mice were housed in conventional cages in the absence or presence of a cocktail of broad spectrum antibiotics added to the drinking water previously shown to suppress gut microbiota (1,19).

Gut Microbial TMA Lyase Activity Assay

TMA lyase activity was monitored by quantifying d9-TMA production from d9(trimethyl) labeled potential nutrient precursors by stable isotope dilution LC/MS/MS analysis. Briefly, TMA lyase activity was typically quantified by incubating the indicated enzyme source (C57BL/6J female mouse intestine segments or human feces from healthy vegans/vegetarians and omnivores). Reactions were initiated by the addition of d9-labeled substrates (d9-TML, d9-carnitine or d9-choline) incubated under anaerobic conditions. Following 20 hours incubation at 37° C., reactions were halted, $[^{13}C_3,^{15}N]$-TMA (Sigma Chemicals, St. Louis, MO) in 0.2 N formic acid was added as an internal standard, followed by immediate extraction of TMA isotopologues into the organic layer produced following mixing with successive additions of 2 ml hexane, 1 ml butanol and 0.2 ml 1N NaOH (to deprotonate the TMA isotopologues). Mixtures were then vortexed, centrifuged, and the upper hexane layer was transferred to a 12×75 mm PTFE capped threaded glass tube, acidified with the addition of 200 µl of 0.2 N formic acid, vortexed and the organic and aqueous layers were separated by centrifugation. The now protonated TMA isotopologues were recovered in the aqueous phase for quantitation by stable isotope dilution LC/MS/MS analysis. Sample aliquots were injected onto a reverse phase C18 HPLC column (2.0×150 mm, 5 µm, Phenomenex Prodigy (Phenomenex)) eluted at a flow rate of 0.2 ml/min and resolved using a linear gradient between 0.2% formic acid in water and 0.2% formic acid in acetonitrile/methanol (95:5, v/v). HPLC column effluent was introduced into an AB Sciex 5500 QTRAP mass spectrometer using electrospray ionization in the positive-ion mode. Both d9-TMA and $[^{13}C_3,^{15}N]$TMA were monitored using multiple reaction monitoring of parent and characteristic daughter ions: m/z 69→49 for d9-TMA; and m/z 64→47 for $[^{13}C_3,^{15}N]$TMA. Reactions without microbial enzyme source (tissues, cells, cell lysates, or isolated proteins) were used as blank. Control studies for each individual d9-TMA containing substrate showed negligible (~0.25 nM) background d9-TMA production under the conditions employed.

In Vitro Screening for the Conversions of d9-N6-Trimethyl-Lysine by Human Commensals Human feces and all bacteria including individual strain and fresh combined 68 strains were grown with 100 µM d9-TML or d9-choline (as a positive control) in complex reduced medium in a Coy anaerobic chamber (5% $H_2$, 20% $CO_2$, and 75% N2, 37° C.) for 0-4 days as previously described (27). The reaction was stopped by adding 6N HCl to samples (1:100 dilution to 60 mM final), and freezing at −80° C. until d9-TMA extraction and analysis by LC-MS/MS, as described in Methods above.

In Vivo Carotid Artery Thrombosis Model

Conventional mice (female, 10 weeks old, C57BL/6J, 10 per treatment group) were placed on chemically defined diets for 11 days. Mice were assessed for in vivo thrombosis potential with the common carotid injury model by application of 10% FeCl3 for 1 min (11, 38). To test this, platelets were labeled with Rhodamine 6G (100 µl; 1 mg/ml) and injected directly into the right jugular vein. The left carotid artery was exposed and injured by placing a $FeCl_3$ soaked filter paper for one minute. Thrombus formation was observed in real time with and captured under video camera linked to an intra vital fluorescence microscope. Time to cessation of blood flow was determined by visual inspection of computer images of the thrombosis process from 30 seconds to 30 minutes by investigators blinded to mouse treatment group.

Statistical Analysis

Student's t-test (2 tailed) or Wilcoxon-rank sum test for continuous variables and $X^2$ test for categorical variables were used to examine the difference between groups. Numeric data are presented as mean SD or median (25th-75th percentile=Q1-Q3). Categorical data are presented as n (%). Hazards ratio (HR) for Death/MI/Stroke (MACE) and Death at 5-year follow-up and corresponding 95% CI were estimated using both univariable (unadjusted) and multivariable (adjusted) Cox models. Kaplan-Meier analysis with Cox proportional hazards regression was used for time-to-event analysis to determine hazard ratios (HR) and 95% confidence intervals (95% CI) for MACE, and all-cause mortality. Adjustments were made for individual traditional cardiac risk factors including but not limited to age, sex, HDL, LDL, smoking, diabetes mellitus, history of hypertension, high sensitivity C-reactive protein level. All analyses were performed using R 3.4.1 (Vienna, Austria, 2017). P-values <0.05 were considered statistically significant.

A genome-wide association study (GWAS) for plasma TML levels was carried out using linear regression analyses with natural log transformed values and adjustment for age and sex. All analyses were performed using PLINK 1.07 (39) assuming additive genetic models. The results of the Coronary Artery Disease Genome-wide Replication and Meta-Analysis (CARDIoGRAM) Consortium were used to determine whether variants identified for plasma TML levels were associated with CVD. CARDIoGRAM represents a GWAS meta-analysis of CVD comprising 60,801 cases and 123,504 controls from 48 studies, in which logistic regression was first used in each cohort to test for association with CVD using a log-additive model with adjustment for age and sex and taking into account the uncertainty of possibly imputed genotypes. Subsequently, a meta-analysis was performed separately for every SNP from each study that passed the quality control criteria using a fixed effects model with inverse variance weighting or a random effects model, depending on the presence of heterogeneity between studies (25). The results of these meta-analyses were used to determine whether loci for TML were associated with CVD.

Additional Methods

Chemical Synthesis of [d9-N,N,N-trimethyl] lysine and N6-trimethyl-lysine

[d9-N, N, N-trimethyl] lysine (d9-TML) and N6-trimethyl-lysine (TML) were prepared as described previously (Chen and Benoiton, 1976, Can J Chem. 1976; 54:3310-3311.) but with some modifications[1]. In brief, N (u) Boc-Lysine (9.85 g, 40 mmol) was dissolved into 400 ml methanol. Sodium hydroxide (5.28 g, 132 mmol) was added. Either d3-methyl iodide (for preparing d9-TML) or methyl iodide (for preparing TML) (140 mmol) was added in one portion. The reaction mixture was stirred at room temperature overnight. The reaction was followed by TLC on plastic backed Silica Gel plate in methanol with 1% v/v formic acid, developed with $I_2$ fumes. The reaction mixture was transferred onto silica gel bed (90 mm diameter) equilibrated in methanol in a coarse fritted Buchner funnel. Sodium iodide was removed by elution with 1.5 liters of methanol. The product (d9-TML or TML) was eluted from the column with 3 liters of 30% water v/v in methanol. Rotary evaporation of this methanol portion gave the crude product. Boc group of the crude product was removing by adding 100 ml concentrated HCl (1.2 moles) and incubation at 90-100° C. for one hour. Rotary evaporation of the product solution at 60° C. under 60 mBar vacuum was performed until a viscous oil was obtained. The remaining HCl was removed by adding 100 ml of water and evaporated. The crude product was dissolved in 100 ml water and titrated to pH 6 with 1 M sodium hydroxide, and was concentrated by rotary evaporation in reduced pressure. The crude product was again dissolved in absolute ethanol and was filtered to remove residual inorganic salt. Residual water was removed by rotary evaporation and any final moisture was removed azeotropically by sequential rotary evaporation after adding absolute ethanol under vacuum. The crude product was re-dissolved in a minimal amount of boiling 2-propanol, the solution was cooled to room temperature, and gave the recrystallized d9-TML or TML recovered. High resolution mass spectrometry (m/z) for d9-TML: $[M]^+$ (m/z) calculated exact mass for $^2H_9C_9H_{12}N_2O_2$, 198.2168; found, 198.2163; TML: calculated exact mass for $C_9H_{21}N_2O_2$, 189.1603; found, 189.1595. d9-TML and TML were also confirmed by high-resolution NMR (FIGS. 8 and 11).

REFERENCES

1. Wang et al., Gut flora metabolism of phosphatidylcholine promotes cardiovascular disease. Nature. 2011; 472 (7341):57-63.
2. Albert et al., Myocardial lipidomics. Developments in myocardial nuclear lipidomics. Front Biosci. 2007; 12:2750-2760.
3. Beger et al., Metabolomics enables precision medicine: "A White Paper, Community Perspective". Metabolomics. 2016; 12(10):149.

46

4. Yang and Han, Lipidomics: Techniques, Applications, and Outcomes Related to Biomedical Sciences. Trends Biochem Sci. 2016; 41(11):954-969.
5. Ussher et al., The Emerging Role of Metabolomics in the Diagnosis and Prognosis of Cardiovascular Disease. J Am Coll Cardiol. 2016; 68(25):2850-2870.
6. Gross, The evolution of lipidomics through space and time. Biochim Biophys Acta. 2017; 1862(8):731-739.
7. Afshinnia et al. Impaired beta-Oxidation and Altered Complex Lipid Fatty Acid Partitioning with Advancing CKD. J Am Soc Nephrol. 2018; 29(1):295-306.
8. Koeth et al., Intestinal microbiota metabolism of L-carnitine, a nutrient in red meat, promotes atherosclerosis. Nat Med. 2013; 19(5):576-585.
9. Koeth et al., gamma-Butyrobetaine is a proatherogenic intermediate in gut microbial metabolism of L-carnitine to TMAO. Cell Metab. 2014; 20(5):799-812.
10. Gregory et al., Transmission of atherosclerosis susceptibility with gut microbial transplantation. J Biol Chem. 2015; 290(9):5647-5660.
11. Zhu et al., Gut Microbial Metabolite TMAO Enhances Platelet Hyperreactivity and Thrombosis Risk. Cell. 2016; 165(1):111-124.
12. Kind et al. Identification of small molecules using accurate mass MS/MS search. Mass Spectrom Rev. 2017; April 24.
13. Wang et al., Sharing and community curation of mass spectrometry data with Global Natural Products Social Molecular Networking. Nat Biotechnol. 2016; 34(8):828-837.
14. Wohlgemuth et al. SPLASH, a hashed identifier for mass spectra. Nat Biotechnol. 2016; 34(11):1099-1101.
15. Wang et al., Measurement of trimethylamine-N-oxide by stable isotope dilution liquid chromatography tandem mass spectrometry. Anal Biochem. 2014; 455:35-40.
16. Tang et al. Intestinal microbial metabolism of phosphatidylcholine and cardiovascular risk. N Engl J Med. 2013; 368(17):1575-1584.
17. Senthong et al., Trimethylamine N-Oxide and Mortality Risk in Patients With Peripheral Artery Disease. J Am Heart Assoc. 2016; 5(10):e002816.
18. Tang et al., Increased Trimethylamine N-Oxide Portends High Mortality Risk Independent of Glycemic Control in Patients with Type 2 Diabetes Mellitus. Clin Chem. 2017; 63(1):297-306.
19. Wang et al., Prognostic value of choline and betaine depends on intestinal microbiota-generated metabolite trimethylamine-N-oxide. Eur Heart J. 2014; 35(14):904-910.
20. Vaz and Wanders, Carnitine biosynthesis in mammals. Biochem J. 2002; 361(Pt 3):417-429.
21. Servillo et al., Where does N(epsilon)-N6-trimethyl-lysine for the carnitine biosynthesis in mammals come from? PLoS One. 2014; 9(1):e84589.
22. Kouzarides, Chromatin modifications and their function. Cell. 2007; 128(4):693-705.
23. Stallcup, Role of protein methylation in chromatin remodeling and transcriptional regulation. Oncogene. 2001; 20(24):3014-3020.
24. Zhang et al., Lysine methylation: beyond histones. Acta Biochim Biophys Sin (Shanghai). 2012; 44(1):14-27.
25. Nikpay et al., A comprehensive 1,000 Genomes-based genome-wide association meta-analysis of coronary artery disease. Nat Genet. 2015; 47(10):1121-1130.
26. Rakoff-Nahoum et al., Recognition of commensal microflora by toll-like receptors is required for intestinal homeostasis. Cell. 2004; 118(2):229-241.

27. Romano et al., Intestinal microbiota composition modulates choline bioavailability from diet and accumulation of the proatherogenic metabolite trimethylamine-N-oxide. M Bio. 2015; 6(2):e02481.

28. Wang et al., Non-lethal Inhibition of Gut Microbial Trimethylamine Production for the Treatment of Atherosclerosis. Cell. 2015; 163(7):1585-1595.

29. Craciun and Balskus, Microbial conversion of choline to trimethylamine requires a glycyl radical enzyme. Proc Natl Acad Sci USA. 2012; 109(52):21307-21312.

30. Zhu et al., Carnitine metabolism to trimethylamine by an unusual Rieske-type oxygenase from human microbiota. Proc Natl Acad Sci USA. 2014; 111(11):4268-4273.

31. Scoumanne and Chen, Protein methylation: a new mechanism of p53 tumor suppressor regulation. Histol Histopathol. 2008; 23(9):1143-1149.

32. Shi et al., Histone demethylation mediated by the nuclear amine oxidase homolog LSD1. Cell. 2004; 119(7):941-953.

33. Tsukada et al., Histone demethylation by a family of JmjC domain-containing proteins. Nature. 2006; 439 (7078):811-816.

34. Wang et al., Protein carbamylation links inflammation, smoking, uremia and atherogenesis. Nat Med. 2007; 13(10):1176-1184.

35. Tsugawa et al., MS-DIAL: data-independent MS/MS deconvolution for comprehensive metabolome analysis. Nat Methods. 2015; 12(6):523-526.

36. Tsugawa et al., Hydrogen Rearrangement Rules: Computational MS/MS Fragmentation and Structure Elucidation Using MS-FINDER Software. Anal Chem. 2016; 88(16):7946-7958.

37. Pluskal et al., modular framework for processing, visualizing, and analyzing mass spectrometry-based molecular profile data. BMC Bioinformatics. 2010; 11:395.

38. Chen et al., A specific CD36-dependent signaling pathway is required for platelet activation by oxidized low-density lipoprotein. Circ Res. 2008; 102(12):1512-1519.

39. Purcell et al. PLINK: a tool set for whole-genome association and population-based linkage analyses. Am J Hum Genet. 2007; 81(3):559-575.

40. Loland et al, The Association between Progression of Atherosclerosis and the Methylated Amino Acids Asymmetric Dimethylarginine and N6-trimethyl-lysine, PLOS ONE, May 2013, Volume 8 (5), e64774, pgs 1-9.

Example 2

TMAO+TML Combination Risk Analysis

This Example describes further analysis of the data from Example 1 based on patient risk for the combination of TMAO and TML levels. Such analysis illustrates how TML and TMAO provide additive prognostic value.

First, a tertile analysis is provided for the combination of TMAO and TML vs the risk of major adverse cardiac event (MAC). The results are shown in FIG. 12 and Table 11 below.

TABLE 11

| Tertile analysis for combo TMAO and TML vs MACE | | | | |
|---|---|---|---|---|
| | | TMAO(µM) | | |
| Range | | <3 | 3-5.5 | >5.5 |
| TML (µM) | <0.5 | 39/442 = 8.8 1.0 | 27/262 = 10.3 1.2(0.7-1.9) | 26/175 = 14.9 1.7(1.1-2.9)* |
| | 0.5-0.6 | 16/143 = 11.2 1.3(0.7-2.3) | 16/153 = 10.5 1.2(0.7-2.1) | 17/99 = 17.2 2.0(1.1-3.5)* |
| | >0.6 | 25/169 = 14.8 1.8(1.1-2.9)* | 40/256 = 15.6 1.8(1.2-2.8)** | 120/441 = 27.2 3.4(2.4-4.9)*** |

*P < 0.05,
**P < 0.01,
***P < 0.001

Second, a cut-off analysis is provided for the combination of TMAO and TML vs the risk of MACE. The results are shown in Table 12 and FIG. 13.

TABLE 12

| Analysis for TMAO = 2.5, 6.0 and TML = 0.5, 0.8 vs MACE | | | | |
|---|---|---|---|---|
| | | TMAO(µM) | | |
| Range | | <2.5 | 2.5-6 | >6 |
| TML (µM) | <0.5 | 28/332 = 8.4 1.0 | 43/413 = 10.4 1.2(0.8-2.0) | 21/134 = 15.7 1.9(1.1-3.4)* |
| | 0.5-0.8 | 26/185 = 14.1 1.7(1.0-2.9)* | 52/449 = 11.6 1.4(0.9-2.2) | 59/255 = 23.1 2.9(1.8-4.5)*** |
| | >0.8 | 5/23 = 21.7 2.7(1.1-7.1)* | 23/120 = 19.2 2.4(1.4-4.2)** | 69/229 = 30.1 4.0(2.6-6.2)*** |

*P < 0.05,
**P < 0.01,
***P < 0.001

As shown in table 12 above, particular exemplary cut-offs can be used for low, intermediate, and high risk for TMAO (e.g., less than 2.5 µM, 2-5-6.0 µM, and above 6.0 µM) and cutoffs for low v intermediate v high risks for TML (e.g., less than 0.5 µM, 0.5-0.8 µM, and above 0.8 µM) vs MACE (3 yr risk of MI, stroke or death).

This analysis of the combined impact of TMAO and TML on disease risk (e.g., CVD, MACE, heart failure) can be used to reveal important risk provides. For example, even at the lowest TML level, increased TMAO level is associated with significant increase (~2-fold) in MACE risk. And conversely, at the lowest TMAO level, TML dose dependently shows significantly increased MACE risk (e.g., ~2.7 fold risk at highest TML level). When both TMAO and TML are high, there is 4-fold increased MACE risks compared to when both are low. Also for example, at low TML and TMAO, the absolute annual event rate in the Example 1 cohort is 8.4/3=2.8%/yr, and at high TML and high TMAO, the absolute annual event rate is 30.1/3=10.0%/yr. It is noted that a 10% annual MACE rate is a relatively high risk rate (e.g., as high risk is generally considered a 10 yr event rate of 7.5% or higher.

Example 3

Cleveland and Swiss Cohorts Risk Analysis

This Example describes how plasma levels of TML were quantified in two independent cohorts using mass spectrometry, and how its relationship with CVD risks were investigated. In a Cleveland Cohort (N=530), comprised of patients presenting to the emergency department with chest pain and suspected ACS (Acute Coronary Syndrome), TML was associated with major adverse cardiac events (MACE, myocardial infarction, stroke, need for revascularization, or all-cause mortality) over both 30-day (3rd tertile (T3), adjusted odds ratio (OR) 1.77, 95% confidence interval (CI), 1.04-3.01; P<0.05) and 6-month (T3, adjusted OR 1.95, 95% CI, 1.15-3.32; P<0.05) follow-up independent of traditional risks factors and indices of renal function. Elevated TML levels were also associated with incident long-term (7-year) all-cause mortality (T3, adjusted hazard ratio (HR) 2.52, 95% CI, 1.50-4.24; P<0.001), and MACE, even amongst patients persistently negative for cardiac troponin T at presentation (e.g. 30-day MACE, T3, adjusted OR 4.49, 95% CI, 2.06-9.79; P<0.001). TML in combination with TMAO showed additive value for near- and long-term CVD event risks, including in patients with "negative" high sensitivity Troponin T levels. In a multicenter Swiss Cohort (N=1683) comprised of adjudicated ACS patients, similar associations between TML and incident adverse cardiac risks were observed (e.g. Incident (1-year) mortality, adjusted T3 HR 2.74, 95% CI, 1.28-5.85; P<0.05. And incident (1 year) MACE, adjusted T3 HR 1.55, 95% CI, 1.04-2.31; P<0.05). Plasma TML levels, alone and additive with TMAO, predict both near- and long-term CVD risks in patients who present with ACS.

Methods

Study Populations

Two independent cohorts of patients with suspected versus adjudicated ACS were examined. Patients from both the Cleveland Cohort and the Swiss ACS Cohort gave informed consent, and study protocols were approved by respective institutional review boards. All studies were conducted according to the declaration of Helsinki.

The Cleveland Cohort (N=530) was a single-center, prospective cohort study designed to examine cardiac troponin T (cTnT) in the diagnosis of myocardial infarction, as described previously (19, 20) with samples reanalyzed with the newer (5th generation) high sensitivity cTnT assay (Roche Diagnostics). Adult patients 18 years old and above who presented with chest pain of suspected cardiac origin to the Emergency Department (ED) within 24 hours of initial onset were eligible. Blood was collected at presentation (baseline), 4, 8 and 16 hours later and plasma frozen at −70 degrees C. until analysis. Of the initial 530 patients, 112 were cardiac troponin T (cTnT)-positive (cTnT≥0.1p g/L) at initial evaluation period, and 418 patients were persistently negative for serial testing of cTnT. All events were adjudicated with medical record checks.

TABLE 14

Baseline Characteristics of Patients in the Cleveland Cohort stratified according to TML tertiles

| Characteristics | All patients (N = 530) | Tertile 1 (N = 174) <0.74 µM | Tertile 2 (N = 181) 0.74-1.11 µM | Tertile 3 (N = 175) >1.11 µM | P value |
|---|---|---|---|---|---|
| Age (yr) (mean ± sd) | 62.4 ± 13.9 | 59.2 ± 13.7 | 63.6 ± 13.1 | 64.5 ± 14.3 | <0.001 |
| Male (%) | 57.5 | 46 | 64.1 | 62.3 | 0.001 |
| C-reactive protein (mg/dL) | 0.56(0.19-1.19) | 0.57(0.16-1.13) | 0.48(0.17-1.04) | 0.61(0.24-1.37) | 0.18 |
| History of hyperlipidemia (%) | 50 | 44 | 49.1 | 56.6 | 0.063 |
| History of Diabetes (%) | 27.2 | 19.9 | 27.3 | 34.1 | 0.013 |
| History of Hypertension (%) | 65.6 | 58.2 | 65.3 | 73 | 0.016 |
| History of revascularization (%) | 33.9 | 22.8 | 35.3 | 42.9 | 0.001 |
| History of CAD (%) | 48.9 | 52.8 | 46.2 | 47.9 | 0.46 |
| History of smoking (%) | 61.1 | 55.3 | 60.7 | 67.1 | 0.089 |
| HDL-C (mg/dL) | 39(32-47) | 42(34.8-48) | 38(32-48) | 36(30-45) | 0.001 |
| LDL-C (mg/dL) | 104.5(80-133.2) | 106(80.8-132.2) | 102(77-126) | 108(81-141) | 0.25 |
| Adjudicated ACS (%) | 37.6 | 26 | 37.6 | 49.1 | <0.001 |
| TMAO (µM) | 4.28(2.55-7.91) | 2.9(1.89-4.61) | 3.98(2.53-6.87) | 7.14(4.38-13.54) | <0.001 |
| Baseline hs-TnT (µg/L) | 0.018(0.009-0.045) | 0.014(0.007-0.032) | 0.017(0.009-0.036) | 0.029(0.011-0.067) | 0.002 |
| TML (µM) | 0.89(0.68-1.33) | 0.6(0.49-0.68) | 0.89(0.81-1) | 1.58(1.35-2.03) | <0.001 |
| eGFR (mL/min/1.73 m$^2$) | 75.8(54.7-91.2) | 85.3(69.6-101.3) | 76.3(61.5-89.7) | 59.4(34.6-81.2) | <0.001 |
| Baseline medications (%) | | | | | |
| Aspirin (%) | 36.5 | 30.4 | 38.4 | 40.5 | 0.14 |
| ACE inhibitors (%) | 25.4 | 21.5 | 20.7 | 33.7 | 0.01 |
| Statin (%) | 13 | 10.1 | 11 | 17.8 | 0.08 |
| Beta blockers (%) | 23.1 | 18.4 | 23.8 | 27 | 0.18 |

Continuous data are presented as mean ± standard deviation or median (interquartile range), categorical variables are presented as %. One-way ANOVA or Kruskal-Wallis test were used for numeric data comparison. Chi-square test was used for categorical data.

The Swiss ACS Cohort (N=1683) was a multi-center (Bern, Zurich, Geneva and Lausanne), prospective study, performed as part of the Special Program University Medicine (SPUM-ACS) study (ClinicalTrials.gov number: NCT01000701). It involved consecutive and prospective recruitment of subjects presenting with adjudicated ACS, as previously described. (10, 21).

Quantification of Plasma Trimethyllysine and TMAO

Stable isotope dilution LC/MS/MS was used to quantify circulating TML and TMAO in positive ion multiple reaction monitoring mode using characteristic parent to daughter ion transitions for endogenous analytes and isotope labeled internal standards, as previously described (6, 7, herein incorporated by reference in their entireties). Briefly, stable

TABLE 15

Baseline Characteristics of Patients in Swiss ACS Cohort stratified according to TML tertiles

| Characteristics | All patients (N = 1683) | Tertile 1 (N = 556) <0.56 μM | Tertile 2 (N = 567) 0.56-0.73 μM | Tertile 3 (N = 560) >0.73 μM | P value |
|---|---|---|---|---|---|
| Age (yr) (mean ± sd) | 63.9 ± 12.4 | 61.5 ± 11.6 | 62.4 ± 12.3 | 68 ± 12.4 | <0.001 |
| Male (%) | 77.8 | 65.3 | 83.4 | 84.5 | <0.001 |
| C-reactive protein (mg/dL) | 2.8(1.1-8) | 2.5(1.08-6.03) | 2.4(1.08-6.93) | 3.6(1.4-12.5) | <0.001 |
| History of hyperlipidemia (%) | 62.6 | 62.9 | 59.6 | 65.4 | 0.14 |
| History of Diabetes (%) | 17.5 | 13.8 | 15.3 | 23.2 | <0.001 |
| History of Hypertension (%) | 59.3 | 52.7 | 56.3 | 68.9 | <0.001 |
| History of revascularization (%) | 17.4 | 14.7 | 15.2 | 22.3 | 0.001 |
| History of CAD (%) | 36.8 | 37.2 | 37.6 | 35.6 | 0.77 |
| History of smoking (%) | 67.8 | 69.1 | 69.3 | 65 | 0.22 |
| HDL-C (mg/dL) | 1.1(0.9-1.4) | 1.2(1-1.4) | 1.1(0.9-1.4) | 1.1(0.9-1.3) | <0.001 |
| LDL-C (mg/dL) | 3.1(2.3-3.8) | 3.2(2.4-4) | 3.1(2.5-3.9) | 2.8(2.1-3.5) | <0.001 |
| TMAO (μM) | 2.87(1.94-4.85) | 2.29(1.59-3.26) | 2.6(1.9-3.94) | 4.35(2.82-7.17) | <0.001 |
| Hs-TnT (μg/L) | 0.2(0.06-0.71) | 0.18(0.05-0.54) | 0.2(0.06-0.7) | 0.24(0.06-0.93) | 0.005 |
| TML (μM) | 0.64(0.52-0.81) | 0.48(0.42-0.52) | 0.64(0.6-0.69) | 0.9(0.81-1.09) | <0.001 |
| eGFR (mL/min/1.73 m$^2$) | 100.2(74.2-126.9) | 112.7(90.3-137.9) | 103.8(83.7-129.1) | 77.4(54.5-105.9) | <0.001 |
| Baseline medications (%) | | | | | |
| Aspirin (%) | 33.3 | 26.8 | 30.9 | 42.4 | <0.001 |
| ACE inhibitors (%) | 18.3 | 16.1 | 14.8 | 24 | <0.001 |
| Statin (%) | 31.4 | 28.4 | 30 | 35.8 | 0.02 |
| Beta blockers (%) | 26.3 | 21.4 | 23.9 | 33.8 | <0.001 |

Continuous data are presented as mean ± standard deviation or median (interquartile range), categorical variables are presented as %. One-way ANOVA or Kruskal-Wallis test were used for numeric data comparison. Chi-square test was used for categorical data.

Medications

For the Cleveland suspected ACS Cohort, patients were treated during their ED 24-hour hospital stay and after discharge according to standard of care by their treating physicians. For the Swiss ACS Cohort, the protocol for medications during hospital stay and follow-up comprised administration of aspirin and an additional platelet inhibitor (prasugrel or ticagrelor) for 1 year after the ACS unless an indication for oral anticoagulation was present. Treating physicians were advised to administer a statin (rosuvastatin 20 mg/d), an angiotensin-converting enzyme inhibitor or angiotensin II receptor blocker and a beta-blocker immediately after the ACS as tolerated by the patient.

Biochemical Analyses

Cardiac troponin T (reference value <0.1 μg/L) was measured by commercial ELISA on an ES300 analyzer (Enzymun Troponin T; Roche Diagnostics, Boehringer Mannheim, Indianapolis, Indiana) (22), The lower limit of detection of this assay is 0.02 μg/L. The Roche assay was performed with the use of the Elecsys system (05092744190 Troponin T hs Elecsy, Roche Diagnostics, Indianapolis, IN, USA) for cTnT (5th generation), with a LOD is 0.005 μg/L, the 99th percentile 0.014 μg/L, and the 10% CV is 0.013 μg/L. (23). Estimated glomerular filtration rate (eGFR; in mL/min per 1.73 m2) was calculated for each cohort using the modification of Diet in Renal Disease study equation (24). TML and TMAO were quantified using stable isotope dilution LC/MS/MS analyses as previously described using a Shimadzu Nexera Ultra High Performance Liquid Chromatograph (UHPLC) system interfaced with Shimadzu 8050 triple quadrupole mass spectrometer. (14).

isotope labeled internal standards d9-trimethyl-TMAO (Cambridge Isotope Laboratories, Inc. Tewksbury, MA) and d9-trimethyllysine (synthesized and characterized as described previously (6) dissolved in methanol were added to plasma, proteins methanolic precipitated at 0° C., and supernatants analyzed after injection onto a Luna Silica column (2.0×150 mm, 5 μm, Phenomenex, Torrance, CA) operated at a flow rate of 0.35 ml min-1 and eluted using a discontinuous gradient composed of solvent A, 0.1% propionic acid in water versus solvent B, 0.1% acetic acid in methanol, using a Shimadzu Nexera Ultra High Performance Liquid Chromatograph (UHPLC) system interfaced with Shimadzu 8050 triple quadrupole mass spectrometer.

Clinical Diagnosis

Elevated troponin was defined by reference values set by each institution. Unstable angina was characterized by the presence of angina at rest, a sudden increase in episodes of previously stable angina, ST-segment depression, or T-wave inversions, as previously described (2). EKG findings from both Cohorts were accessed and verified by personnel blinded to the patients' diagnoses. In both cohorts, diagnosis of STEMI, NSTEMI or unstable angina were adjudicated by medical record review by qualified investigators unaware of patients' diagnoses or analyte (TML, TMAO, cTnT) levels.

Definitions of Outcomes

All-cause mortality included cardiac, vascular and non-cardiovascular causes of death. Major adverse cardiovascular events (MACE) were defined as a composite of MI, stroke, revascularization, or all-cause mortality. Reviews of medical records and follow-up phone survey or clinical visit were documented for the 30-day, 6-month and 1 year outcomes by the blinded investigators. The Cleveland Cohort was followed annually for all-cause mortality. Repeat revascularization included any repeat coronary revascularization (target and non-target vessel); clinically indicated repeat revascularization included any clinically driven repeat coronary revascularization (target and non-target vessel).

Statistical Analysis

Wilcoxon-rank sum test or student's t-test for continuous variables and $X^2$ tests or Fisher Exact Test for categorical variables were used to determine significant difference between groups. The statistical analysis of MACE is different between the Cleveland Cohort and Swiss ACS cohorts. For the Cleveland cohort, due to the lack of time to event information excepting for mortality, MACE is a binary composite-"yes" or "no" to non-fatal MI, non-fatal stroke, the need for revascularization, or all-cause mortality. Odds ratio (OR) for binary MACE and corresponding 95% confidence interval (CI) were calculated using both univariable (unadjusted) and multivariable (adjusted) logistic regression models. For the Swiss cohort, MACE is a time-to-event outcome, and is defined as time to first occurrence of non-fatal MI, non-fatal stroke, need for revascularization, or all-cause mortality. Kaplan-Meier curves (unadjusted) along with Cox proportional hazards regression models was used for time-to-event analysis. Hazard ratio (HR) with 95% CI for incident MACE and all-cause mortality were calculated for both univariable (unadjusted) and multivariable (adjusted) Cox models. Both logistic regression models and Cox models were adjusted for traditional cardiac risk factors including age, sex, high density lipoprotein cholesterol (HDL-C), low density lipoprotein cholesterol (LDL-C), smoking, presence or absence of diabetes mellitus and hypertension, and indices of renal function (eGFR). Category-free net reclassification improvement (NRI) and area under the receiver-operating characteristic curves (AUC) were calculated to evaluate the incremental predictive ability of TML for predicting an adverse event, and adjusted the same covariates from the logistic regression model (binary endpoint) or Cox model (time to event data) with traditional risk factors and eGFR. 25 All analysis was performed on R 3.5.1. (Vienna, Austria), and P-value <0.05 was considered statistically significant.

Results

Baseline Characteristics of Patients in Both Cleveland and Swiss ACS Cohorts

Baseline characteristics of both the Cleveland Cohort and the Swiss ACS Cohort, both cumulative and stratified by tertiles of plasma TML, are shown in Tables 14 and 15, respectively. Elevated TML levels at presentation in each cohort was observed amongst subjects who were older, had a history of diabetes mellitus or hypertension, and were more likely to have lower HDL-C. The Cleveland Cohort consisted of 530 sequential patients presenting to the emergency department with complaint of chest pain, 88 patients (16.6%) had unstable angina and 199 patients (37.6%) had adjudicated ACS at presentation. 112 patients (21.1%) were noted to be cTnT positive (cTnT≥0.1 μg/L) during the initial evaluation period (baseline, 4, 8, or 16 h post presentation sample) and 418 patients remained persistently negative for cTnT testing. Furthermore, 5th generation high-sensitivity TnT (hs-TnT) was used to re-measure samples for all patients (N=530) using either baseline (N=415) or 4-hour (N=115) samples for those without remaining baseline sample. Of these, 247 patients (N=192/415 baseline, N=55/115 4 hours) had a hs-TnT level below the universal 99th percentile cut-off derived from healthy patients (hs-TnT <0.014 μg/L) (26, 27). Follow-up was completed for 30-day and 6-month periods. 30-day outcomes included myocardial infarction (MI) in 115 patients, stroke in 1 patient, revascularization in 160 patients, all-cause death in 7 patients, and the composite MACE in 202 patients (38.1%). Cumulative outcomes at 6 months included MI in 117 patients, stroke in 6 patients, revascularization in 163 patients, all-cause death in 29 patients, and the composite MACE in 220 patients (41.5%). All-cause mortality at 7 years was available in 89% (N=474) of the Cleveland Cohort patients. The Swiss ACS population included 1683 patients with adjudicated ACS and onset of symptoms within 72 hours. In the Swiss ACS Cohort, 881 patients (52.3%) had STEMI, 731 patients (43.4%) had NSTEMI, and 71 patients (4.2%) had UA at presentation. Outcomes at 1 year included MI in 52 patients, stroke in 21 patients, revascularization in 99 patients, all-cause death in 71 patients including cardiac death 56 patients (78.9%), and the composite MACE in 190 patients (11.3%).

Trimethyllysine Association with MACE and Long-Term Mortality in the Cleveland Cohort We examined the relationship between the levels of TML and incident cardiovascular events and long-term mortality within the Cleveland Cohort. Individuals with higher plasma TML levels at presentation were more likely to experience MACE over the initial 30-day and 6-month periods following enrollment (P<0.0001 each; FIG. 14A). Over 7-year follow-up, 136 deaths occurred in the study cohort. TML levels were also higher in individuals who died in the ensuing long-term (7-year) period (P<0.0001; FIG. 14A). Kaplan-Meier survival estimates showed enhanced mortality with increasing TML (log-rank, P<0.0001; FIG. 14B). Elevated TML levels were also associated with significant increased odds for MACE at 30 days (3rd vs 1st TML tertile: OR, 2.61, 95% CI, 1.67-4.08, P<0.001) and 6 months follow-up (3rd vs 1st TML tertile: OR, 2.81, 95% CI, 1.81-4.38, P<0.001) (FIG. 14C). And TML was also associated with increased risk of 7-year mortality (3rd vs 1st TML tertile: HR, 4.55, 95% CI, 2.84-7.30, P<0.001) (FIG. 14C). Following multivariable logistic-regression or Cox models adjusting for traditional risk factors (age, sex, smoking, hypertension and diabetes mellitus, low-density lipoprotein cholesterol (LDL-C), high-density lipoprotein cholesterol (HDL-C)) and indices of renal function, elevated (3rd vs 1st tertile) plasma TML remained independently associated with MACE over the ensuing 30-day (OR, 1.77, 95% CI, 1.04-3.01, P<0.05) and 6-month (OR, 1.95, 95% CI, 1.15-3.32, P<0.05) periods, as well as increased risk of all-cause mortality over the ensuing 7-year period (HR, 2.52, 95% CI, 1.50-4.24, P<0.001) (FIG. 14C). The inclusion of TML as a covariate resulted in a significant improvement in risk estimation to the fully adjusted model for MACE at 30 days as monitored by net reclassification improvement (NRI) (NRI=0.20, P<0.05), but no significant improvement in the AUC (AUC, 0.67 (0.63-0.72) (with TML) vs. 0.67 (0.62-0.71) (without TML), P=0.42). Similar results were observed for MACE at 6 months (NRI, 0.30, P<0.001; AUC, 0.69 (0.65-0.74) vs. 0.68 (0.64-0.73), P=0.21) and 7-year all-cause mortality (NRI, 0.40, P<0.001; AUC, 0.82 (0.77-0.86) vs. 0.81 (0.76-0.85), P=0.27) (Table 16).

TABLE 16

| Outcome | Model | Value with 95% CI | P value |
|---|---|---|---|
| Cleveland Cohort | AUC With TML | 0.67 [0.63, 0.72] | 0.42 |
| (N = 530) | AUC Without TML | 0.67 [0.62, 0.71] | |
| MACE at 30 days | Overall NRI | 0.20 | 0.02 |
| | Event NRI | 0.035 | |
| | Non-event NRI | 0.16 | |
| Cleveland Cohort | AUC With TML | 0.69 [0.65, 0.74] | 0.21 |
| (n = 530) | AUC Without TML | 0.68 [0.64, 0.73] | |
| MACE at 6 months | Overall NRI | 0.30 | <0.001 |
| | Event NRI | 0.12 | |
| | Non-event NRI | 0.18 | |
| Cleveland Cohort | AUC With TML | 0.82 [0.77, 0.86] | 0.27 |
| (n = 474) | AUC Without TML | 0.81 [0.76, 0.85] | |
| All-cause mortality | Overall NRI | 0.40 | <0.001 |
| at 7 years | Event NRI | 0.32 | |
| | Non-event NRI | 0.080 | |
| Cleveland Cohort | AUC With TML | 0.71 [0.66, 0.77] | 0.02 |
| Troponin negative | AUC Without TML | 0.65 [0.59, 0.72] | |
| (n = 418) | Overall NRI | 0.48 | <0.001 |
| MACE at 30 days | Event NRI | 0.32 | |
| | Non-event NRI | 0.16 | |
| Cleveland Cohort | AUC With TML | 0.73 [0.68, 0.79] | 0.009 |
| Troponin negative | AUC Without TML | 0.68 [0.62, 0.73] | |
| (n = 418) | Overall NRI | 0.49 | <0.001 |
| MACE at 6 months | Event NRI | 0.33 | |
| | Non-event NRI | 0.16 | |
| Swiss | AUC With TML | 0.65 [0.61, 0.7] | 0.18 |
| (n = 1683) | AUC Without TML | 0.64 [0.6, 0.69] | |
| | Overall NRI | 0.064 | 0.39 |

Area under the Receiver Operator Characteristic Curve (AUC) and Net Reclassification Improvement (NRI) comparison in both Cleveland and Swiss ACS cohorts. NRI estimates and AUC along with 95% CT were presents using unit-less numbers,[10] P values for pair-wise AUC comparison were calculated using the Delong method[11]. Overall NRI, event NRI, and non-event NRI were calculated and compared.[8, 12]

We explored sex specific association of TML levels with MACE at 30 days and 6 months (male, N=305; female N=225), and all-cause mortality at 7 years (male, N=278; female, N=196). Elevated TML levels (Tertile 3 vs Tertile 1) were associated with increased odds of MACE at 30 days and 6 months and increased risk of 7-year all-cause mortality in males and females alike. Moreover, the association remained significant for females independent of traditional risk factors and indices of renal function (FIG. 20) for both MACE (6 months) and mortality (7 years). Similar subcohort analyses showed elevated TML levels were associated with MACE and 7-year all-cause mortality amongst subjects with versus without history of coronary artery disease (CAD) (FIG. 20).

The Association of Trimethyllysine with Adverse Clinical Outcomes in Patients Persistently Negative for Troponin T at Presentation with Chest Pain We examined whether trimethyllysine levels may provide clinical utility among patients without evidence of myocardial necrosis (i.e., remain negative for troponin T throughout the monitoring period of baseline, 4, 8 and 16 hours after admission). Of the subjects that remained persistently negative for troponin T (cTnT<0.1 µg/L) during the initial evaluation period (N=418), TML was higher among those who subsequently experienced a MACE over the ensuing 30 days (median (IQR) 1.10 µM (0.85-1.60) vs 0.83 µM (0.65-1.18); P<0.0001) and 6 months (median (IQR) 1.07 µM (0.85-1.59) vs 0.82 µM (0.64-1.17); P<0.0001). Amongst patients initially negative for troponin T, the frequency of experiencing a MACE over the ensuing 30 days and 6 months increased with increasing TML tertiles (e.g., 8.9% and 11.1% in tertile (T) T1(<0.72 µM), 22.5% and 28.2% in T2(0.73-1.08 µM), and 32.6% and 37.6% in T3(1.09 µM), (P<0.05 for trend)). TML levels in relation to MACE among patients persistently negative for cTnT testing are shown in FIG. 15. As compared with patients in the first tertile of TML levels, patients in the highest tertile (T3) revealed a significantly increased (4.96-fold) odds of MACE at 30 days (OR 4.96, 95% CI, 2.49-9.89, P<0.001). Among patients persistently negative for cTnT, plasma TML levels remained significantly associated with MACE at both 30 days (T3 OR 4.49, 95% CI, 2.06-9.79, P<0.001) and 6 months (T3 OR 4.41, 95% CI, 2.11-9.23, P<0.001), even following adjustments for traditional risk factors and indices of renal function (P<0.001 each, FIG. 15). The inclusion of TML as a covariate resulted in a significant improvement in risk estimation over traditional risk factors and indices of renal function in both NRI and AUC for MACE at 30 days (NRI, 0.48, P<0.001; AUC, 0.71(0.68-0.77) (with TML) vs. 0.65 (0.59-0.72) (without TML), P=0.02) and 6 months (NRI, 0.49, P<0.001; AUC, 0.73(0.68-0.79) vs 0.68(0.62-0.73), P<0.01)) (Table 17)

TABLE 17

| Outcome | Model | Value with 95% CI | P value |
|---|---|---|---|
| Cleveland Cohort | AUC With TML | 0.67 [0.63, 0.72] | 0.42 |
| (N = 530) | AUC Without TML | 0.67 [0.62, 0.71] | |
| MACE at 30 days | Overall NRI | 0.20 | 0.02 |
| | Event NRI | 0.035 | |
| | Non-even NRI | 0.16 | |
| Cleveland Cohort | AUC with TML | 0.69 [0.65, 0.74] | 0.21 |
| (n = 530) | AUC Without TML | 0.68 [0.64, 0.73] | |
| MACE at 6 months | Overall NPI | 0.30 | <0.001 |
| | Event NRI | 0.12 | |
| | Non-event NRI | 0.18 | |
| Cleveland Cohort | AUC With TML | 0.82 [0.77, 0.86] | 0.27 |
| (n = 474) | AUC Without TML | 0.81 [0.76, 0.85] | |
| All-cause mortality | Overall NRI | 0.40 | <0.001 |
| at 7 years | Event NRI | 0.32 | |
| | Non-event NRI | 0.080 | |
| Cleveland Cohort | AUC With TML | 0.71 [0.66, 0.77] | 0.02 |
| Troponin negative | AUC Without TML | 0.65 [0.59, 0.72] | |
| (n = 418) | Overall NRI | 0.48 | <0.001 |
| MACE at 30 days | Event NRI | 0.32 | |
| | Non-event NRI | 0.16 | |
| Cleveland Cohart | AUC With TML | 0.73 [0.68, 0.79] | 0.009 |
| Troponin negative | AUC Without TML | 0.68 [0.62, 0.73] | |
| (n = 418) | Overall NRI | 0.49 | <0.001 |
| MACE at 6 months | Event NRI | 0.33 | |
| | Non-event NRI | 0.16 | |
| Swiss | AUC With TML | 0.65 [0.61, 0.7] | 0.18 |
| (n = 1683) | AUC Without TML | 0.64 [0.6, 0.69] | |
| | Overall NRI | 0.064 | 0.39 |

Area under the Receiver Operator Characteristic Curve (AUC) and Net Reclassification Improvement (NRI) comparison in both Cleveland and Swiss ACS cohorts. NRI estimates and AUC along with 95% CI were presents using unit-less numbers. (10) P values for pair-wise AUC comparison were calculated using the Delong method (11). Overall NRI, event NRI, and non-event NRI were calculated and compared. (8, 12)

Additive Clinical Value of TML and TMAO for Incident Cardiovascular Events, the Cleveland Cohort Isotope tracer studies reveal dietary TML can serve as a TMAO-producing nutrient precursor via gut microbiota, and in clinical studies, combining TML with TMAO provides additive long-term prognostic value among stable subjects undergoing cardiac evaluations. (14). We therefore hypothesized that concurrent assessment of TML and TMAO could enhance risk stratification among patients presenting with suspected ACS. Among subjects in the Cleveland Cohort at initial presentation (baseline), Spearman's correlation analyses showed a significant association between plasma TML and TMAO levels (r=0.50, P<0.0001; FIG. 16A). Kaplan-Meier survival plots stratifying TML and TMAO into low vs high levels (below versus above median value) shows that elevated TML and TMAO levels were each associated with a graded increase (Log rank P<0.001) in incident mortality risk, with highest cumulative mortality rate noted among those with both high TML and TMAO levels (FIG. 16B). When TMAO levels were included in the Cox regression models, elevated levels of both TML and TMAO retained significant prognostic value even after adjustments for multiple risk factors and indices of renal function (FIG. 16B). To further examine both the independence and potential additive significance of TML and TMAO, we stratified the whole cohort into tertile groups of both TML and TMAO. Patients having the lowest tertile of both TML and TMAO levels (reference group) experienced an absolute annual mortality rate of only 1.4%/year. In contrast, patients with combined highest tertiles of TML and TMAO levels experienced an 8.6%/year annual event rate, and a significant 8.52-fold relative risk of incident mortality in 7 years (unadjusted HR 8.52; 95% CI, 4.04-17.98; P<0.001) (FIG. 16C, Table 18).

middle line depicts the calculated Hazard Ratio (95% Confidence Interval) for risk of incident mortality relative to subjects with low levels of both TML and TMAO as reference group. And the bottom line provides the P value for comparison relative to subjects with low levels of both TML and TMAO as reference group.

Moreover, even among patients with low TMAO levels (T1) at presentation, increasing levels of TML were associated with significant increase in mortality risk (3.76-fold risk when TML is the highest tertile yet TMAO remains low; P<0.05) (FIG. 16C, Table 18). Similarly, among patients with the low TML levels, increasing TMAO levels dose dependently were associated with increased mortality risk (e.g., 4.59-fold risk when TMAO is high (T3) yet TML is low (T1); P<0.01. FIG. 16C).

High sensitivity troponin assays are enabling earlier diagnosis of MI and when negative, help identify subjects at reduced risk over the ensuing 30-days. (26, 28-30, herein incorporated by reference). We therefore next explored the potential clinical value of TML and TMAO levels for incident cardiovascular events in patients who were below the 99th percentile cut-off on the fifth-generation (Roche) high sensitivity Troponin T testing at baseline and 4 hours (≤0.014 μg/L, threshold used globally (26, 27) and lower than the 0.019 μg/L cutoff-the 99th percentile in the U.S.30). Subjects were again stratified based on tertiles of both TML and TMAO levels. Among these 247 patients (hs-cTnT<0.014 μg/L), the overall MACE rate over the ensuing 6 months period was 21.9% (n=54/247). Elevated TML and TMAO levels remained significantly associated with increased cardiovascular events (T3/T3, TML/TMAO vs T1/T1, TML/TMAO, unadjusted OR, 4.41, 95% CI, 1.34-14.56, P<0.05) (FIG. 16D, Table 19), and TML provided

TABLE 18

TMAO and TML provide independent additive clinical prognostic value for prediction of mortality risk at 7 years (Cleveland Cohort, N = 474)

| | | TMAO (μM) | | |
|---|---|---|---|---|
| | Range | <3.0 μM (low) | 3.0-6.29 μM (intermediate) | >6.29 μM (high) |
| TML (μM) | <0.7 μM (low) | 1.4%/yr 1.00 | 1.1%/yr 0.73(0.19-2.79) P = 0.86 | 5.6%/yr 4.59(1.66-12.67) P < 0.001 |
| | 0.7-1.09 μM (intermediate) | 3.0%/yr 2.16(0.90-5.18) P = 0.066 | 3.3%/yr 2.42(1.05-5.60) P = 0.017 | 3.8%/yr 2.85(1.18-6.86) P = 0.017 |
| | >1.09 μM (high) | 4.8%/yr 3.76(1.30-10.85) P = 0.012 | 4.9%/yr 4.13(1.74-9.83) P < 0.01 | 8.6%/yr 8.52(4.04-17.98) P < 0.001 |

This cohort (N=474) was stratified into low, intermediate and high level subgroups of TML and TMAO using the cutoffs indicated. Within each cell, the annual absolute incident event rate for mortality is shown at the top. The additive prognostic value in combination with TMAO for prediction of MACE odds, even in patients with "negative" hs-TnT levels (i.e. <99th % cut-off on Roche 5th generation assay).

TABLE 19

TMAO and TML provide independent additive clinical prognostic value
for prediction of 6-month MACE odds among patients who were below
the 99th percentile cut-off on hs-cTnT (Cleveland Cohort, N = 247)

| | | TMAO (μM) | | |
|---|---|---|---|---|
| Range | | <2.7 μM (low) | 2.7-4.61 μM (intermediate) | >4.62 μM (high) |
| TML | <0.7 μM | 9.1% | 4.6% | 21.4% |
| (μM) | (low) | 1.00 | 0.48(0.05-4.54) | 2.73(0.53-14.05) |
| | | | P = 0.52 | P = 0.23 |
| | 0.7-0.99 μM | 9.7% | 21.9% | 47.6% |
| | (intermediate) | 1.07(0.22-5.17) | 2.80(0.74-10.55) | 9.09(2.39-34.64) |
| | | P = 0.97 | P = 0.11 | P < 0.01 |
| | >0.99 μM | 16.7% | 35.7% | 30.6% |
| | (high) | 2.00(0.19-21.62) | 5.56(1.54-20.10) | 4.41(1.34-14.56) |
| | | P = 0.57 | P < 0.01 | P = 0.014 |

This sub-cohort among patients who were below the 99th percentile cut-off on hs-cTnT (N=247) was stratified into low, intermediate and high level subgroups of TML and TMAO using the cutoffs indicated. Within each cell, the absolute event rate at 6-month for MACE is shown at the top. The middle line depicts the calculated Odds Ratio (95% Confidence Interval) for risk of incident MACE relative to subjects with low levels of both TML and TMAO as reference group. And the bottom line provides the P value for comparison relative to subjects with low levels of both TML and TMAO as reference group.

Elevated Plasma TML Levels Predict Incident Cardiovascular Risks in an Independent Cohort of ACS Patients: The Multicenter Swiss ACS Cohort We examined the clinical prognostic value of TML in an independent cohort, the multicenter Swiss ACS Cohort, a prospective study of 1,683 patients with adjudicated ACS and one-year longitudinal follow-up (10, 21). TML levels were higher among patients who experienced a MACE (myocardial infarction, stroke, need for revascularization, or all-cause mortality) in the one-year follow-up period compared to those who did not experience MACE (Median, 0.72 vs 0.64 μM, P<0.001; FIG. 17A). TML levels were also higher among subjects who died within one year after presentation compared with those who did not (Median, 0.94 vs 0.64 μM, P<0.0001; FIG. 17A). Kaplan-Meier survival plots illustrate the dose-dependent association observed between increasing TML and reduced freedom from MACE (Log rank P<0.001; FIG. 17B). Within the multisite Swiss ACS Cohort, the 1-year risk of incident MACE or mortality increased in consecutive TML tertiles, with individuals in the top tertile (relative to bottom tertile) showing a 1.90-fold risk of MACE (HR 1.90, 95% CI 1.34-2.70, P<0.001) and a 5.23-fold risk of all-cause mortality (HR 5.23, 95% CI 2.56-10.67, P<0.001; FIG. 17C). After adjustment for traditional risk factors and indices of renal function, elevated TML levels remained an independent predictor of 1-year MACE (HR, 1.55, 95% CI 1.04-2.31, P<0.05) and mortality (HR, 2.74, 95% CI 1.28-5.85, P<0.01) risks (FIG. 17C). The inclusion of TML as a covariate resulted in a significant improvement in risk estimation to the fully adjusted model prediction of 1-year mortality, as monitored by NRI (NRI=0.32, P<0.01), and trended toward improvement in AUC for predicting incident mortality, albeit not at a statistically significant level (AUC, 0.79 (0.74-0.85) (with TML) vs. 0.78 (0.72-0.83) (without TML), P=0.071). Addition of TML to the fully adjusted model for predicting 1-year MACE did not show significant improvement in NRI and AUC (NRI, 0.064, P=0.39; AUC, 0.65 (0.61-0.70) vs. 0.64 (0.60-0.69), P=0.18). We also calculated cumulative risk with death not associated with MACE as a competing risk and comparison was made by Fine-Gray test. (31). For this analysis, MACE was redefined as time to first occurrence of non-fatal MI, non-fatal stroke, need for revascularization, or CVD mortality. Essentially similar results were observed, with 3rd tertile TML levels significantly associated with cumulative incidence of MACE (HR 1.77, 95% CI 1.24-2.55, P=0.002). Following adjustments with a fully loaded model (traditional risk factors and indices of renal function), however, a strong trend was observed that failed to reach significance (adjusted HR 1.44, 95% CI 0.96-2.16, P=0.081).

Similar to results observed with the Cleveland Cohort, a significant positive association was observed between plasma TML and TMAO levels in the multicenter Swiss ACS Cohort (Spearman r=0.42, P<0.001, N=1683; FIG. 18A). Moreover, in Kaplan-Meier plots stratifying both TML and TMAO levels above vs below median TML and TMAO levels, the highest cumulative MACE rate was observed in patients with high levels of both TML and TMAO, and lowest cumulative event rate in subjects possessing both low TML and TMAO levels. In Cox survival analyses including both TMAO and multivariate risk factor adjustment for traditional risks factors and indices of renal function, an elevated TML level was associated with a 2.1-fold risk for MACE (1-year) among those with concurrently high TMAO level (adjusted HR, 2.10, 95% CI 1.41-3.12, P<0.001; FIG. 18B). TML and TMAO also showed additive prognostic value when ranked as tertiles (FIG. 18C, Table 20).

TABLE 20

TMAO and TML provide independent additive clinical prognostic value
for prediction of MACE risk at 1 year (Swiss ACS Cohort, N = 1683)

| | | TMAO (µM) | | |
|---|---|---|---|---|
| | Range | <2.2 µM (low) | 2.2-4.27 µM (intermediate) | >4.27 µM (high) |
| TML (µM) | <0.56 µM (low) | 8.5%/yr 1.00 | 8.5%/yr 0.98(0.53-1.83) P = 0.95 | 9.4%/yr 1.12(0.50-2.51) P = 0.79 |
| | 0.56-0.88 µM (intermediate) | 8.6%/yr 1.02(0.56-1.85) P = 0.94 | 7.3%/yr 0.85(0.48-1.50) P = 0.57 | 16.1%/yr 1.93(1.13-3.28) P = 0.015 |
| | >0.88 µM (high) | 17.1%/yr 2.12(0.87-5.18) P = 0.10 | 12.2%/yr 1.45(0.67-3.15) P = 0.35 | 23.3%/yr 2.91(1.75-4.84) P < 0.001 |

The entire cohort (N=1683) was stratified into low, intermediate and high level subgroups of TML and TMAO using the cutoffs indicated. Within each cell, the annual absolute incident event rate for MACE is shown at the top. The middle line depicts the calculated Hazard Ratio (95% Confidence Interval) for risk of incident MACE relative to subjects with low levels of both TML and TMAO as reference group. And the bottom line provides the P value for comparison relative to subjects with low levels of both TML and TMAO as reference group.

Patients with ACS experience a wide range of adverse cardiac events. Risk stratification, based on clinical characteristics is challenging, yet risk evaluation is needed to guide triage, management decisions and preventive efforts. (32, 33). We show that, in patients who are presenting with either suspected or adjudicated ACS, TML serves as an independent and additive (with TMAO, traditional risk factors and indices of renal function) predictor of adverse outcomes in patients at risk for either near-term or long-term cardiovascular events. Remarkably, plasma TML levels served as an excellent predictor of MACE even in patients who were consistently negative for troponin T. Moreover, amongst subjects presenting with chest pain and yet were initially "negative" with hs-TnT levels (i.e. <99% cut-off on Roche 5th generation assay), elevated TML level (both alone and in combination with TMAO) were associated with near-term adverse outcomes. The present results indicate, for example, that the quantification of TML and TMAO at presentation provides added clinical utility for identify patients at risk for either near-term or long-term adverse events. TML thus helps identify those who might benefit from early intervention, and escalation in preventive risk reducing efforts who might not otherwise be recognized using traditional electrocardiographic or laboratory diagnostic testing.

REFERENCES FOR EXAMPLE 3 (ALL OF WHICH ARE HEREIN INCORPORATED BY REFERENCE)

1. Hollander et al., Circulation 2016; 134(7):547-564.
2. Zhelev et al., BMJ 2015; 350:h15.
3. Chapman et al., Circulation 2017; 135(17):1586-1596.
4. Chapman et al., JAMA 2017; 318(19):1913-1924.
5. Eagle et al., Circulation 2010; 121(12):1447-1454.
6. Wang et al., Nature 2011; 472(7341):57-63.
7. Seldin et al., J Am Heart Assoc 2016; 5(2):e002767.
8. Zhu et al., Cell 2016; 165(1):111-124.
9. Tang et al., N Engl J Med 2013; 368(17):1575-1584.
10. Li et al., Eur Heart J 2017; 38(11):814-824.
11. Suzuki et al., Clin Chem 2017; 63(1):420-428.
12. Schiattarella et al., Eur Heart J 2017; 38(39):2948-2956.
13. Qi et al., J Cell Mol Med 2018; 22(1):185-194.
14. Li et al., JCI Insight 2018; 3(6):e99096(6).
15. Hulse et al., J Biol Chem 1978; 253(5):1654-1659.
16. Hoppel et al., Biochem J 1980; 188(2):509-519.
17. Skagen et al., Atherosclerosis 2016; 247:64-69.
18. Strand et al., J Clin Endocrinol Metab 2018; 103(3):1033-1041.
19. McErlean et al., Am J Cardiol 2000; 85(4):421-426.
20. Brennan et al., N Engl J Med 2003; 349(17):1595-1604.
21. Klingenberg et al., Eur Heart J Acute Cardiovasc Care 2018; 7(2):129-138.
22. Muller-Bardorff et al., Clin Chem 1997; 43(3):458-466.
23. Aldous et al., Ann Clin Biochem 2011; 48(Pt 3):241-248.
24. Levey et al., Ann Intern Med 2009; 150(9):604-612.
25. Pencina et al., Stat Med 2008; 27(2):157-172; discussion 207-112.
26. Giannitsis et al., Clin Chem 2010; 56(2):254-261.
27. Body et al., Clin Chem 2017; 63(1):21-23.
28. Korley et al., J Am Coll Cardiol 2013; 61(17):1753-1758.
29. Thelin et al., Eur Heart J Acute Cardiovasc Care 2015; 4(5):403-409.
30. Peacock et al., JAMA Cardiol 2018; 3(2):104-111.
31. Austin et al., Circulation 2016; 133(6):601-609.
32. Roffi et al., Eur Heart J 2016; 37(3):267-315.
33. Van et al., Eur Heart J 2003; 24(1):28-66.
34. Wang et al., Eur Heart J 2014; 35(14):904-910.
35. Koeth et al., Nat Med 2013; 19(5):576-585.
36. Servillo et al., PLoS One 2014; 9(1):e84589.
37. Porras-Yakushi et al., J Biol Chem 2005; 280(41):34590-34598.
38. Davis et al., JNutr 1993; 123(6):1109-1116.
39. Fischer et al., Br J Nutr 2009; 101(2):190-196.
40. Handy et al., Circulation 2011; 123(19):2145-2156.
41. Greer et al., Nature 2010; 466(7304):383-387.
42. Rhein et al., J Biol Chem 2014; 289(35):24640-24651.
43. LaBadie et al., Biochem J 1976; 160(1):85-95.
44. Dunn et al., J Biol Chem 1981; 256(23):12437-12444.
45. Dunn et al., J Biol Chem 1984; 259(17):10764-10770.
46. Huszar et al., J Mol Biol 1975; 94(3):311-326.
47. Morse et al., Biochemistry 1975; 14(19):4316-4325.

ADDITIONAL REFERENCES (HEREIN
INCORPORATED BY REFERENCE)

1. McErlean et al., Am J Cardiol 2000; 85(4):421-426.
2. Brennan et al., N Engl J Med 2003; 349(17):1595-1604.
3. Muller-Bardorff et al., Clin Chem 1997; 43(3):458-466.
4. Aldous et al., Ann Clin Biochem 2011; 48(Pt 3):241-248.
5. Levey et al., Ann Intern Med 2009; 150(9):604-612.
6. Li et al., JCI Insight 2018; 3(6):e99096(6).
7. Wang et al., Anal Biochem 2014; 455:35-40.
8. Pencina et al., Stat Med 2008; 27(2):157-172; discussion 207-112.
9. Austin et al., Circulation 2016; 133(6):601-609.
10. Leening et al., Ann Intern Med 2014; 160(2):122-131.
11. DeLong et al., Biometrics 1988; 44(3):837-845.
12. Pencina et al., Stat Med 2011; 30(1):11-21.

Although only a few exemplary embodiments have been described in detail, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

What is claimed is:

1. A method of treating chronic kidney disease comprising:
   a) identifying a subject as having chronic kidney disease based on: i) having increased levels of N6-trimethyl-lysine (TML) compared to a control level, or having increased levels of TML and trimethylamine-n-oxide (TMAO) compared to control levels, and
   b) treating said subject with a first agent or first procedure that inhibits the TMA/FMO3/TMAO pathway.

2. The method of claim 1, wherein said first agent that inhibits the TMA/FMO3/TMAO pathway is selected from a compound comprising: a halomethyl betaine, a halomethyl betaine salt, a halomethyl betaine amide, and a halomethyl dimethyl amino alcohol.

3. The method of claim 1, wherein said first agent that inhibits the TMA/FMO3/TMAO pathway is a compound comprising a halomethyl choline.

* * * * *